US010546469B2

(12) United States Patent
Peterson et al.

(10) Patent No.: US 10,546,469 B2
(45) Date of Patent: Jan. 28, 2020

(54) SMART-HOME SYSTEM FACILITATING INSIGHT INTO DETECTED CARBON MONOXIDE LEVELS

(71) Applicant: Google LLC, Mountain View, CA (US)

(72) Inventors: Kevin Peterson, San Francisco, CA (US); David Sloo, Menlo Park, CA (US); Yoky Matsuoka, Palo Alto, CA (US); Nicholas Unger Webb, Menlo Park, CA (US)

(73) Assignee: Google LLC, Mountain View, CA (US)

( * ) Notice: Subject to any disclaimer, the term of this patent is extended or adjusted under 35 U.S.C. 154(b) by 516 days.

(21) Appl. No.: 14/508,777

(22) Filed: Oct. 7, 2014

(65) Prior Publication Data
US 2015/0096352 A1  Apr. 9, 2015

Related U.S. Application Data

(60) Provisional application No. 61/887,969, filed on Oct. 7, 2013, provisional application No. 61/887,963, filed on Oct. 7, 2013.

(51) Int. Cl.
  *G08B 5/36* (2006.01)
  *G08B 17/10* (2006.01)
  (Continued)

(52) U.S. Cl.
  CPC ............. *G08B 5/36* (2013.01); *F24F 11/30* (2018.01); *F24F 11/33* (2018.01); *F24F 11/34* (2018.01);
  (Continued)

(58) Field of Classification Search
  CPC ........ G08B 29/181; G08B 21/12; A62B 5/00; G07C 9/00182; F24F 11/0017;
  (Continued)

(56) References Cited

U.S. PATENT DOCUMENTS 4,254,414 A   3/1981  Street et al.
4,313,110 A   1/1982  Subulak et al.
(Continued)

FOREIGN PATENT DOCUMENTS

WO   2011-143273 A1   11/2011
WO   2012-092622 A2    7/2012
WO   2012-092627 A1    7/2012

OTHER PUBLICATIONS

Non-Final Office Action dated Feb. 1, 2016, for U.S. Appl. No. 14/508,555, 21 pages.
(Continued)

*Primary Examiner* — Regis J Betsch
*Assistant Examiner* — Kaleria Knox
(74) *Attorney, Agent, or Firm* — Kilpatrick Townsend & Stockton LLP

(57) ABSTRACT

In an embodiment, a method determines one or more sources of carbon monoxide (CO) in a smart-home environment that includes a plurality of smart devices that have at least measurement and communication capabilities. The method includes measuring a level of CO in the smart-home environment to generate a CO measurement, and providing the CO measurement and one or more current characteristics of the smart-home environment, from one or more of the smart devices to an analyzing device. The method further includes evaluating, by the analyzing device and with the CO measurement and the current characteristics of the smart-home environment, a set of CO correlation scenarios that attribute generation of CO to a corresponding one of a set of specific sources, and selecting one or more of the specific sources as the most likely source of the CO, by aggregating results of the correlation scenarios.

30 Claims, 31 Drawing Sheets

(51) Int. Cl.
| | |
|---|---|
| G01N 27/02 | (2006.01) |
| G01N 27/12 | (2006.01) |
| G01N 33/00 | (2006.01) |
| G08B 25/00 | (2006.01) |
| G08B 29/18 | (2006.01) |
| G08B 3/10 | (2006.01) |
| G08B 21/14 | (2006.01) |
| H04L 12/28 | (2006.01) |
| G08B 5/22 | (2006.01) |
| G08B 29/04 | (2006.01) |
| F24F 11/30 | (2018.01) |
| G08B 25/01 | (2006.01) |
| G08B 21/18 | (2006.01) |
| G08B 21/12 | (2006.01) |
| G08B 29/02 | (2006.01) |
| G08B 29/26 | (2006.01) |
| G08B 17/117 | (2006.01) |
| G08B 29/22 | (2006.01) |
| H04L 29/08 | (2006.01) |
| F24F 11/33 | (2018.01) |
| G01J 1/42 | (2006.01) |
| G01V 8/10 | (2006.01) |
| H05B 33/08 | (2006.01) |
| H05B 37/02 | (2006.01) |
| G06T 7/70 | (2017.01) |
| G06K 9/00 | (2006.01) |
| H04M 1/725 | (2006.01) |
| H04N 7/18 | (2006.01) |
| F24F 11/34 | (2018.01) |
| F24F 120/10 | (2018.01) |
| F24F 11/46 | (2018.01) |
| F24F 11/58 | (2018.01) |
| G08B 19/00 | (2006.01) |
| F24F 11/75 | (2018.01) |
| F24F 11/89 | (2018.01) |
| F24F 11/70 | (2018.01) |

(52) U.S. Cl.
CPC ............ *G01J 1/4204* (2013.01); *G01N 27/02* (2013.01); *G01N 33/004* (2013.01); *G01N 33/0031* (2013.01); *G01V 8/10* (2013.01); *G06K 9/00744* (2013.01); *G06T 7/70* (2017.01); *G08B 3/10* (2013.01); *G08B 5/22* (2013.01); *G08B 17/117* (2013.01); *G08B 21/12* (2013.01); *G08B 21/14* (2013.01); *G08B 21/18* (2013.01); *G08B 21/182* (2013.01); *G08B 25/002* (2013.01); *G08B 25/008* (2013.01); *G08B 25/012* (2013.01); *G08B 29/02* (2013.01); *G08B 29/04* (2013.01); *G08B 29/22* (2013.01); *G08B 29/26* (2013.01); *H04L 12/282* (2013.01); *H04L 12/2803* (2013.01); *H04L 12/2809* (2013.01); *H04L 12/2818* (2013.01); *H04L 67/10* (2013.01); *H04L 67/24* (2013.01); *H04M 1/72561* (2013.01); *H04N 7/183* (2013.01); *H05B 33/0854* (2013.01); *H05B 33/0872* (2013.01); *H05B 37/0218* (2013.01); *H05B 37/0272* (2013.01); *F24F 11/46* (2018.01); *F24F 11/58* (2018.01); *F24F 11/70* (2018.01); *F24F 11/75* (2018.01); *F24F 11/89* (2018.01); *F24F 2120/10* (2018.01); *G08B 19/005* (2013.01); *H04L 67/025* (2013.01); *Y02A 50/243* (2018.01)

(58) Field of Classification Search
CPC ......... F24F 11/33; G05B 13/048; G05B 9/02; G06Q 10/10; G06F 17/3061; G01N 33/065; G01N 33/004; G01S 19/48; G01S 5/18; C01B 13/10; B65B 67/04; G08C 19/16; H05L 67/12; G06T 7/70
USPC ..................... 340/438, 506, 501, 628, 573.1; 126/21 A; 318/282; 702/181; 707/754; 705/14.42; 700/34; 381/82; 165/200; 422/29; 248/99
See application file for complete search history.

(56) References Cited

U.S. PATENT DOCUMENTS

| | | | |
|---|---|---|---|
| 4,390,869 A | 6/1983 | Christen et al. | |
| 5,798,701 A | 8/1998 | Bernal et al. | |
| 5,969,600 A * | 10/1999 | Tanguay | G08B 29/181 340/438 |
| 6,323,780 B1 | 11/2001 | Morris | |
| 6,441,723 B1 | 8/2002 | Mansfield, Jr. et al. | |
| 6,445,292 B1 | 9/2002 | Jen et al. | |
| 6,624,750 B1 | 9/2003 | Marman et al. | |
| 6,920,874 B1 * | 7/2005 | Siegel | F24C 15/2021 126/21 A |
| 7,049,952 B2 * | 5/2006 | Kulesz | G08B 21/12 340/506 |
| 7,360,370 B2 | 4/2008 | Shah et al. | |
| 7,623,028 B2 * | 11/2009 | Kates | G01N 33/0065 340/501 |
| 8,032,254 B2 | 10/2011 | Amundson et al. | |
| 8,108,075 B2 * | 1/2012 | Bohan, Jr. | G05B 9/02 165/200 |
| D660,732 S | 5/2012 | Bould et al. | |
| 8,172,154 B1 | 5/2012 | Figley et al. | |
| 8,489,065 B2 | 7/2013 | Green et al. | |
| 8,494,897 B1 * | 7/2013 | Dawson | G06Q 10/10 705/14.42 |
| 8,539,567 B1 | 9/2013 | Logue et al. | |
| 8,543,649 B2 * | 9/2013 | Gilmour | G06F 17/3061 707/754 |
| 8,544,285 B2 | 10/2013 | Stefanski et al. | |
| 8,594,850 B1 | 11/2013 | Gourlay et al. | |
| 8,606,374 B2 | 12/2013 | Fadell et al. | |
| 8,620,841 B1 | 12/2013 | Filson et al. | |
| 8,643,467 B2 * | 2/2014 | Chutorash | G07C 9/00182 340/5.2 |
| 8,669,878 B1 * | 3/2014 | Vantilburg | A62B 5/00 318/282 |
| 8,727,611 B2 | 5/2014 | Huppi et al. | |
| 9,223,323 B2 | 12/2015 | Matas et al. | |
| 9,342,930 B1 | 5/2016 | Kraft et al. | |
| 9,626,858 B2 | 4/2017 | Sloo et al. | |
| 10,049,280 B2 | 8/2018 | Sloo et al. | |
| 2002/0011923 A1 | 1/2002 | Cunningham et al. | |
| 2002/0044061 A1 * | 4/2002 | Johnston | G01N 33/004 340/628 |
| 2002/0171552 A1 * | 11/2002 | Tate | G08B 27/005 340/573.1 |
| 2004/0135695 A1 | 7/2004 | Barton et al. | |
| 2004/0140892 A1 | 7/2004 | Hanood | |
| 2004/0249479 A1 * | 12/2004 | Shorrock | F24F 11/0017 340/506 |
| 2005/0011997 A1 * | 1/2005 | Kalal | B65B 67/04 248/99 |
| 2005/0105743 A1 * | 5/2005 | Faltesek | G01S 5/18 381/82 |
| 2005/0253709 A1 | 11/2005 | Baker | |
| 2006/0119477 A1 | 6/2006 | Tice | |
| 2007/0133840 A1 * | 6/2007 | Cilia | G06K 9/00369 382/103 |
| 2007/0255522 A1 | 11/2007 | Gordon et al. | |
| 2007/0279214 A1 | 12/2007 | Buehler | |
| 2008/0071395 A1 * | 3/2008 | Pachner | G05B 13/048 700/34 |

(56) References Cited

U.S. PATENT DOCUMENTS

| | | | |
|---|---|---|---|
| 2009/0077623 A1 | 3/2009 | Baum et al. | |
| 2009/0273470 A1 | 11/2009 | Sinkevicius et al. | |
| 2010/0052574 A1 | 3/2010 | Blakeley et al. | |
| 2010/0195810 A1 | 8/2010 | Mota et al. | |
| 2010/0325074 A1 | 12/2010 | Ng et al. | |
| 2012/0126975 A1 | 5/2012 | Gonzales | |
| 2012/0229285 A1 | 9/2012 | Rauworth et al. | |
| 2013/0024123 A1* | 1/2013 | Ochs | A61B 5/726 702/19 |
| 2013/0046710 A1* | 2/2013 | Kartoun | G06Q 40/06 705/36 R |
| 2013/0154823 A1 | 6/2013 | Ostrer et al. | |
| 2013/0271286 A1 | 10/2013 | Quan et al. | |
| 2013/0286238 A1 | 10/2013 | Tan et al. | |
| 2014/0023556 A1* | 1/2014 | Jiang | C01B 13/10 422/29 |
| 2014/0085093 A1 | 3/2014 | Mittleman et al. | |
| 2014/0167969 A1 | 6/2014 | Wedig et al. | |
| 2014/0172365 A1* | 6/2014 | Hannebutte | G01S 19/48 702/181 |
| 2015/0015390 A1 | 1/2015 | McIntyre et al. | |
| 2015/0077248 A1 | 3/2015 | Eck | |

OTHER PUBLICATIONS

Notice of Publication dated Mar. 17, 2016, for U.S. Appl. No. 14/878,884.

International Preliminary Report on Patentability dated Apr. 21, 2016, for International Patent Application No. PCT/US2014/059526, 9 pages.

International Preliminary Report on Patentability dated Apr. 21, 2016, for International Patent Application No. PCT/US2014/059538, 13 pages.

Non-Final Office Action dated Jul. 6, 2016, for U.S. Appl. No. 14/955,847, 22 pages.

Notice of Publication dated Jul. 20, 2016, for European Patent Application No. 14852527.2.

Notice of Allowance dated Jul. 21, 2016, for U.S. Appl. No. 14/878,884, 9 pages.

Supplemental Notice of Allowance dated Aug. 3, 2016, for U.S. Appl. No. 14/878,884, 2 pages.

Notice of Publication for U.S. Appl. No. 14/955,847 dated Aug. 11, 2016.

ISR/WO mailed on Jan. 12, 2015 for International Patent Application No. PCT/US2014/059498 filed on Oct. 7, 2014, all pages.

International Office Action dated Dec. 24, 2014 for International Patent Application PCT/US2014/059538 filed on Oct. 7, 2014, all pages.

ISR/WO mailed on Feb. 26, 2015 for International Patent Application PCT/US2014/059538 filed on Oct. 7, 2014, all pages.

ISR/WO mailed on Jan. 5, 2015 for International Patent Application PCT/US2014/059526 filed on Oct. 7, 2014, all pages.

U.S. Appl. No. 15/451,930, filed Mar. 7, 2017, Notice of Allowance dated Apr. 2, 2018, all pages.

Extended European Search Report dated Feb. 24, 2017 in European Patent Application No. 14852527.2, all pages.

Non-Final Office action dated Mar. 31, 2016 in U.S. Appl. No. 14/878,884, all pages.

U.S. Appl. No. 61/847,960, filed Jul. 18, 2013, 96 pages.

* cited by examiner

| Color | Meaning |
|---|---|
| ⊖ | Hello / confirmation / message |
| ⊕ | Everything's Ok |
| ⊘ | Something may be wrong |
| ⊙ | Something is definitely wrong |
| ⊚ | Let me help you |

| Animation | Meaning |
|---|---|
| ◎ | "Here's my status" |
| ↻ | "I need you attention" |
| ◐ | "Ok" |
| ❁ | "Hi" |

| Speed | Meaning |
|---|---|
| SLOW | Low urgency |
| FAST | Increased urgency |
| ALARM | Maximum urgency |

*FIG. 13*

| Color | | Pulse | Rotate | Wave | Shimmer | On/Off |
|---|---|---|---|---|---|---|
| | | Alarm or test | | | | |
| | | Pre-Alarm/Heads Up | Battery Very Low<br>Battery Critical | | | |
| | | Lights out (no problems) | Connected to client<br>Test completed (all OK)<br>Post-alarm (All Right) | | | |
| | | Choose Language<br>Button Pressed<br>Doorbell<br>Lights out (problems exist) | Ready for connections<br>Countdown to test<br>Reset<br>Shutdown begin<br>Shutdown countdown | Hush confirmation<br>Problem Description | Starting up | |
| | | | | | | Night Light<br>Safety Light |

FIG. 14

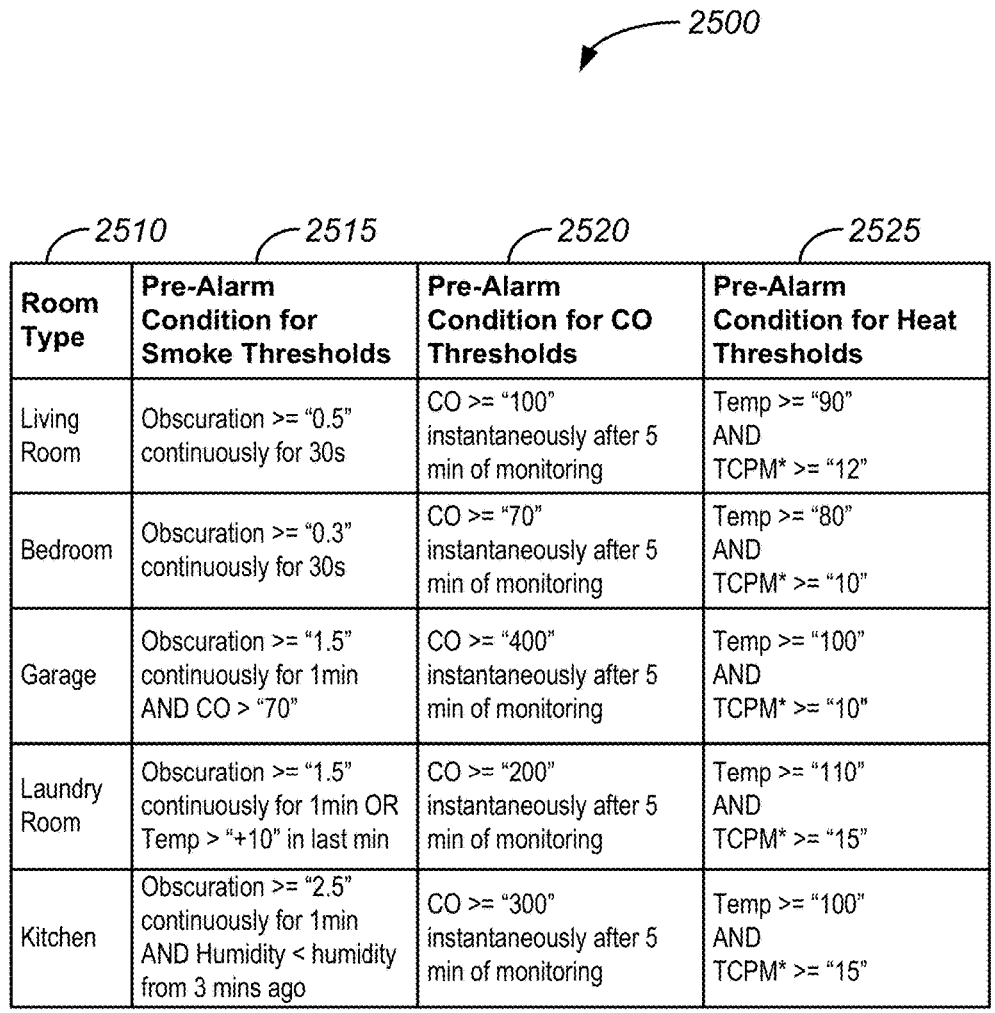

| Room Type | Pre-Alarm Condition for Smoke Thresholds | Pre-Alarm Condition for CO Thresholds | Pre-Alarm Condition for Heat Thresholds |
|---|---|---|---|
| Living Room | Obscuration >= "0.5" continuously for 30s | CO >= "100" instantaneously after 5 min of monitoring | Temp >= "90" AND TCPM* >= "12" |
| Bedroom | Obscuration >= "0.3" continuously for 30s | CO >= "70" instantaneously after 5 min of monitoring | Temp >= "80" AND TCPM* >= "10" |
| Garage | Obscuration >= "1.5" continuously for 1min AND CO > "70" | CO >= "400" instantaneously after 5 min of monitoring | Temp >= "100" AND TCPM* >= "10" |
| Laundry Room | Obscuration >= "1.5" continuously for 1min OR Temp > "+10" in last min | CO >= "200" instantaneously after 5 min of monitoring | Temp >= "110" AND TCPM* >= "15" |
| Kitchen | Obscuration >= "2.5" continuously for 1min AND Humidity < humidity from 3 mins ago | CO >= "300" instantaneously after 5 min of monitoring | Temp >= "100" AND TCPM* >= "15" |

*TCPM = Temperature Change over last minute

| CO measurement type | Smart-home characteristic(s) | Specific CO source | Confidence metric |
|---|---|---|---|
| Single point in or adjacent to garage | • None/random time | User car started/ warming up | 20% |
| Single point in or adjacent to garage | • Time of day | User car started/ warming up | 40% |
| Single point in or adjacent to garage | • Time of day and day of week | User car started/ warming up | 60% |
| Single point in or adjacent to garage | • Time of day, day of week, garage door activity | User car started/ warming up | 80% |
| Single point in or adjacent to garage, very small increase | • None | Unknown motor e.g., visitor car, lawn mower outside garage | 20% |
| Sharp upward trend in kitchen | • No CO trend in adjacent areas<br>• Temp increase in kitchen starting at/after beginning of CO trend<br>• Motion/noise detected in kitchen | Cooking with gas stove | 20% + 20-40% depending on temperature increase |
| Sharp upward trend in kitchen | • No CO trend in adjacent areas<br>• Temp increase in kitchen starting at/after beginning of CO trend<br>• Slight smoke in kitchen<br>• Motion/noise detected in kitchen | Cooking with gas stove | 40% + 20-30% depending on temperature increase |
| Substantial upward trend | • Similar trend at other detectors<br>• HVAC thermostat requesting heat, HVAC fan on | Malfunction in combustion based heat source of HVAC | 50% |
| Substantial upward trend | • Similar trend at other detectors<br>• Slight smoke<br>• HVAC thermostat not requesting heat | Wood stove or fireplace in use for heating | 20% |
| Substantial upward trend | • Similar trend at other detectors<br>• Slight smoke<br>• HVAC thermostat not requesting heat, HVAC fan manually set to on<br>• Outside temp low, inside temp stable or rising where CO is rising | Wood stove or fireplace in use for heating | 50% |
| Slight upward trend | • Users known present<br>• Nighttime<br>• Dim light | Candles | 35% |
| Upward trend in basement | • Humidity or steam detected in bathroom | Possible malfunction in water heater | 20% |

*FIG. 20C*

SMART-HOME SYSTEM FACILITATING INSIGHT INTO DETECTED CARBON MONOXIDE LEVELS

CROSS-REFERENCE TO RELATED APPLICATIONS

This application claims the benefit of priority to U.S. Provisional Patent Application Ser. No. 61/887,969, filed 7 Oct. 2013, entitled "User-Friendly Detection Unit," and U.S. Provisional Patent Application Ser. No. 61/887,963, filed 7 Oct. 2013, entitled "Hazard Detection in a Smart-Sensored Home." The above-identified patent applications are hereby incorporated by reference herein in their entireties for all purposes.

TECHNICAL FIELD

This patent specification relates to systems, devices, methods, and related computer program products for providing hazard-detection objectives. More particularly, this patent specification relates to a plurality of devices, including intelligent, multi-sensing, network-connected hazard detection units or smart hazard detectors (e.g., smoke detectors, carbon monoxide detectors, etc.), that communicate with each other and/or with a central server or a cloud-computing system to provide any of a variety of hazard-detection objectives that are useful in smart building and smart-home environments.

BACKGROUND OF THE INVENTION

Some homes today are equipped with smart-home networks to provide automated control of devices, appliances and systems, such as heating, ventilation, and air conditioning ("HVAC") systems, lighting systems, alarm systems, and home theater and entertainment systems. Smart-home networks may include control panels that a person may use to input settings, preferences, and scheduling information that the smart-home network uses to provide automated control the various devices, appliances and systems in the home. For example, a person may input a desired temperature and a schedule indicating when the person is away from home. The home automation system uses this information to control the HVAC system to heat or cool the home to the desired temperature when the person is home, and to conserve energy by turning off power-consuming components of the HVAC system when the person is away from the home. Also, for example, a person may input a preferred nighttime lighting scheme for watching television. In response, when the person turns on the television at nighttime, the home automation system automatically adjusts the lighting in the room to the preferred scheme.

Additionally, many homes today are equipped with hazard detectors, such as smoke detectors and carbon monoxide detectors. Some of these homes have multiple hazard detectors, where each hazard detector is configured to sound an alarm upon detecting a hazardous condition. Upon hearing an alarm, occupants of these homes may have to search the home to locate the detector that is sounding the alarm to determine whether the alarm is false or whether a hazardous condition actually exists. This can be time-consuming, stressful, and potentially dangerous. Oftentimes the alarm is false. For example, smoke detectors located near bathrooms may mistake shower steam as smoke. Similarly, smoke detectors located in or near kitchens may mistake steam from boiling water as smoke. Also, smoke detectors located in or near kitchens may provide a large number of false alarms due to their over sensitivity to moderate smoke levels common to kitchens.

To avoid the nuisance of false alarms, occupants may disable hazard detectors, such as by removing the batteries or disconnecting the power supply. Disabled or otherwise ineffective hazard detectors result in preventable accidental home deaths. For example, people die each year in home fires, such as fires caused by occupants who fall asleep while smoking cigarettes, because the hazard detectors in their homes were disabled, or because the hazard detectors malfunctioned or were improperly installed. Also, for example, carbon monoxide (CO) poisoning kills approximately one thousand people per year, a lot of whom are children. It is likely that properly functioning CO detectors would have prevented some of these deaths. Accordingly, there is a need for improved hazard detectors for homes and buildings.

BRIEF SUMMARY OF THE INVENTION

Embodiments of the invention provide methods and systems for facilitating the provisioning, set-up, configuration, control, and/or management of intelligent, network-connected, multi-sensing hazard detection units or smart hazard detectors. These smart hazard detectors may be used within a home, building, or structure to warn occupants of the home, building, or structure of potentially hazardous conditions.

In an embodiment, a method for controlling a climate control system of a smart-home environment that includes a plurality of smart devices is provided. The method includes detecting, with a hazard detector of the smart devices, a level of carbon monoxide (CO) at the hazard detector that exceeds a threshold CO level at a location of the hazard detector, determining, by one of the smart devices, that the climate control system includes a combustion based heat source, and in response to the detecting and the determination, transmitting, by a system controller of the climate control system, a first signal to turn off at least one aspect of the climate control system.

In an embodiment, a smart-home environment is provided, that includes a climate control system responsive to signals from a system controller and including a combustion based heat source, and a plurality of smart devices configured for wireless communication amongst themselves. The smart devices include at least a hazard detector that is configured to measure a level of carbon monoxide (CO) at a location of the hazard detector, and the system controller. The system controller is configured to transmit a signal to turn off at least one aspect of the climate control system responsive to the hazard detector detecting a level of CO at that exceeds a threshold CO level at a location of the hazard detector.

In an embodiment, a method for controlling a climate control system of a smart-home environment that includes a plurality of smart devices is provided. The method includes detecting, by a hazard detector of the smart devices, a level of carbon monoxide (CO) at the hazard detector that exceeds a threshold CO level at a location of the hazard detector, determining, by one of the smart devices, that the level of CO at the hazard detector may be associated with operation of the climate control system, and in response to the detecting and the determination, transmitting, by a controller of the smart devices, a first signal to turn off at least one aspect of the climate control system.

In an embodiment, a method determines one or more sources of carbon monoxide (CO) in a smart-home environment that includes a plurality of smart devices that have at least measurement and communication capabilities. The method includes measuring a level of CO in the smart-home environment, by one of the smart devices, to generate a CO measurement, and providing the CO measurement and one or more current characteristics of the smart-home environment, from one or more of the smart devices to an analyzing device. The method further includes evaluating, by the analyzing device and with the CO measurement and the current characteristics of the smart-home environment, a set of CO correlation scenarios that attribute generation of CO to a corresponding one of a set of specific sources, and selecting one or more of the specific sources as the most likely source of the CO, by aggregating results of the correlation scenarios.

To better understand the nature and advantages of the present invention, reference should be made to the following description and the accompanying figures. It is to be understood, however, that each of the figures is provided for the purpose of illustration only and is not intended as a definition of the limits of the scope of the present invention. Also, as a general rule, and unless it is evident to the contrary from the description, where elements in different figures use identical reference numbers, the elements are generally either identical or at least similar in function or purpose.

BRIEF DESCRIPTION OF THE DRAWINGS

FIG. 13 illustrates visual vocabulary for visual effects that may be used by a hazard detector, according to an embodiment;

FIG. 14 illustrates an animation/color matrix of visual effects that may be used by hazard detector, according to an embodiment;

FIG. 17 provides a data table of example thresholds used by hazard detector to determine whether pre-alarm conditions exist, according to an embodiment;

FIG. 20C shows a table illustrating possible correlation scenarios for identifying CO sources, according to an embodiment;

DETAILED DESCRIPTION OF THE INVENTION

Figure 1:
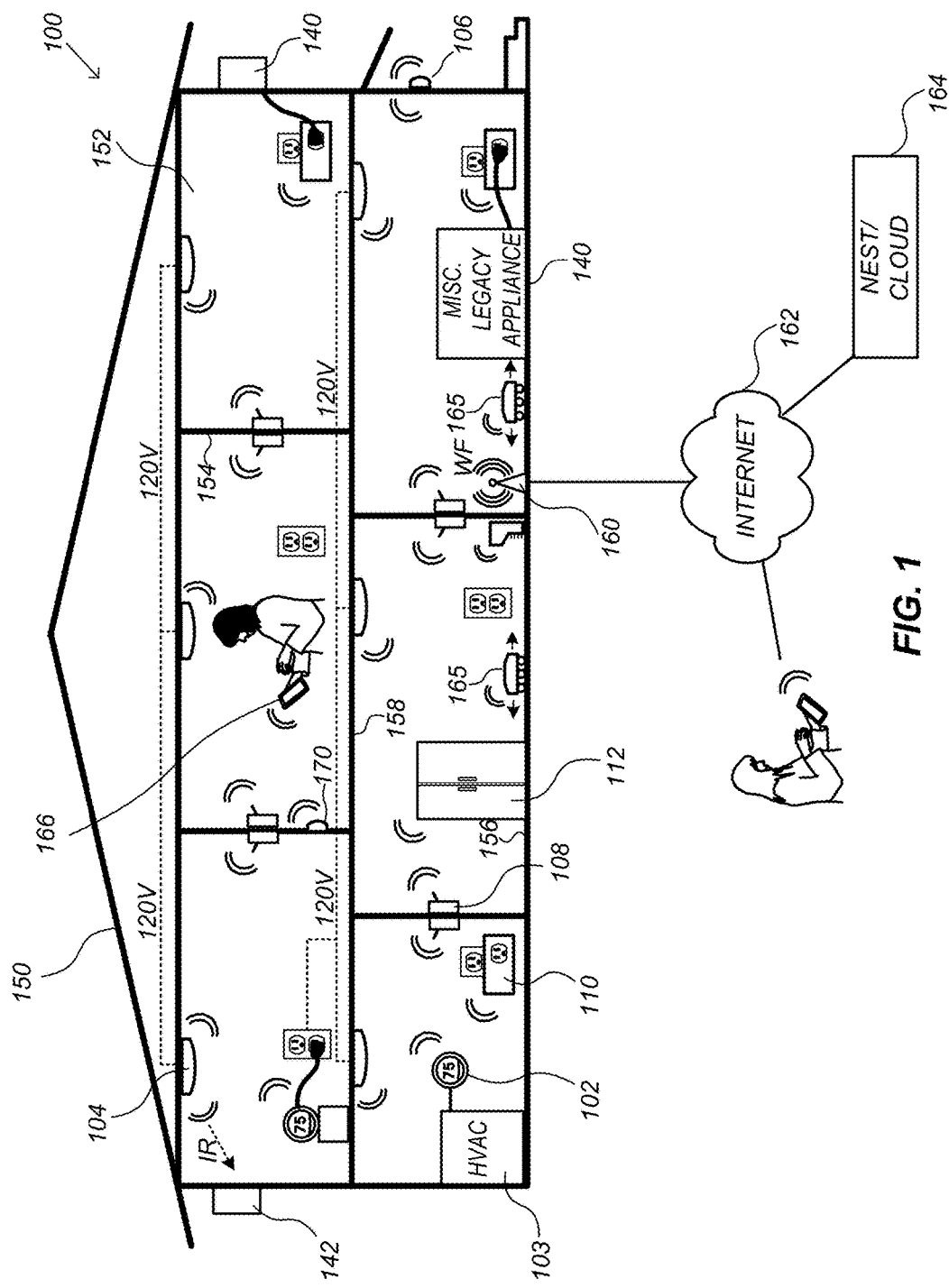
FIG. 1 is an example of a smart-home environment within which one or more of the devices, methods, systems, services, and/or computer program products described further herein will be applicable, according to an embodiment.

The present invention will now be described in detail with reference to certain embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known details have not been described in detail in order not to unnecessarily obscure the present invention.

Overview of the Smart-Home Environment

Provided according to one or more embodiments are methods and systems for setting up, controlling, and/or programming one or more of intelligent, network-connected, multi-sensing hazard detection units or smart hazard detectors. These smart hazard detectors may be configured and adapted to be implemented in a smart-home environment, seamlessly interacting with other devices in the smart-home environment. The term "smart hazard detector" is used herein to represent a particular type of device that can be used for detecting hazards occurring within a structure, e.g., a home, an office or another structure. However, this smart hazard detector may also be capable of controlling other devices, detecting non-hazard related events (e.g., security related events), and/or working in cooperation with other devices to provide additional features to the smart-home environment. Again, it is within the scope of the present teachings for embodiments of the smart hazard detectors of the present invention to detect measurable characteristics other than hazards (e.g., pressure, flow rate, height, position, velocity, acceleration, capacity, power, temperatures, loudness, and brightness) and monitor and/or respond to one or more measurable characteristics of one or more physical systems.

It is to be appreciated that "smart-home environments" may refer to smart environments for homes such as a single-family house, but the scope of the present teachings is not so limited, the present teachings being likewise applicable, without limitation, to duplexes, townhomes, multi-unit apartment buildings, hotels, retail stores, office buildings, industrial buildings, and more generally any living space or work space having one or more smart hazard detectors.

It is to be further appreciated that while the terms user, customer, installer, homeowner, occupant, guest, tenant, landlord, repair person, and the like may be used to refer to the person or persons who are interacting with the smart hazard detector or user interface in the context of some particularly advantageous situations described herein, these references are by no means to be considered as limiting the scope of the present teachings with respect to the person or persons who are performing such actions. Thus, for example, the terms user, customer, purchaser, installer, subscriber, and homeowner may often refer to the same person in the case of a single-family residential dwelling, because the head of the household is often the person who makes the purchasing decision, buys the unit, and installs and configures the unit, and is also one of the users of the unit. However, in other scenarios, such as a landlord-tenant environment, the customer may be the landlord with respect to purchasing the unit, the installer may be a local apartment supervisor, a first user may be the tenant, and a second user may again be the landlord with respect to remote control functionality. Importantly, while the identity of the person performing the action may be germane to a particular advantage provided by one or more of the embodiments—for example, the password-protected hazard detection functionality described further herein may be particularly advantageous where the landlord holds the sole password and can control hazard detection via the hazard detection device—such identity should not be construed in the descriptions that follow as necessarily limiting the scope of the present teachings to those particular individuals having those particular identities.

Turning to the figures, FIG. 1 illustrates an example of a smart-home environment 100 within which one or more of the devices, methods, systems, services, and/or computer program products described further herein can be applicable. The depicted smart-home environment 100 includes a structure 150, which can include, e.g., a house, office building, garage, or mobile home. It will be appreciated that devices can also be integrated into a smart-home environment 100 that does not include an entire structure 150, such as an apartment, condominium, or office space. Further, the smart-home environment can control and/or be coupled to devices outside of the actual structure 150. Indeed, several devices in the smart-home environment need not physically be within the structure 150 at all. For example, a device controlling a pool heater or irrigation system 116 can be located outside of the structure.

The depicted structure 150 includes a plurality of rooms 152, separated at least partly from each other via walls 154. The walls 154 can include interior walls or exterior walls. Each room can further include a floor 156 and a ceiling 158. Devices can be mounted on, integrated with and/or supported by a wall 154, floor 156 or ceiling 158.

In some embodiments, the smart-home environment 100 of FIG. 1 includes a plurality of devices, including intelligent, multi-sensing, network-connected devices (sometimes referred to herein as "smart devices") that can integrate seamlessly with each other and/or with a central server or a cloud-computing system to provide any of a variety of useful smart-home objectives, including hazard-detection objectives. The smart-home environment 100 may include one or more intelligent, multi-sensing, network-connected thermostats 102 (hereinafter referred to as "smart thermostats 102"), one or more intelligent, network-connected, multi-sensing hazard detection units 104 (hereinafter referred to as "smart hazard detectors 104"), and one or more intelligent, multi-sensing, network-connected entryway interface devices 106 (hereinafter referred to as "smart doorbells 106"). Thermostats 102, hazard detectors 104, doorbells 106 are all examples of smart devices.

According to embodiments, the smart thermostat 102 detects ambient climate characteristics (e.g., temperature and/or humidity) and controls a climate control system or HVAC system 103 accordingly, such as by turning on and/or off a fan and/or a heat source of the climate control system 103. (In the present disclosure, "climate control system" is used interchangeably with "HVAC system," to clarify that the disclosure applies equally to systems that do not necessarily include air conditioning. Use of the term "HVAC" herein does not exclude systems that lack air conditioning.)

When the fan of the HVAC or climate control system 103 is on, the fan operates to circulate air between the rooms 152 of the structure 150, and to exhaust air from the structure 150 and draw fresh, outside air into the structure 150. The smart hazard detector 104 may detect the presence of a hazardous condition or a substance indicative of a hazardous condition (e.g., smoke, fire, heat, carbon monoxide, etc.). The smart doorbell 106 may detect a person's approach to or departure from a location (e.g., an outer door), control doorbell functionality, announce a person's approach or departure via audio or visual means, or control settings on a security system (e.g., to activate or deactivate the security system when occupants go and come).

In some embodiments, the smart-home environment 100 of FIG. 1 further includes one or more intelligent, multi-sensing, network-connected wall switches 108 (hereinafter referred to as "smart wall switches 108"), along with one or more intelligent, multi-sensing, network-connected wall plug interfaces 110 (hereinafter referred to as "smart wall plugs 110"). The smart wall switches 108 may detect ambient lighting conditions, detect room-occupancy states, and control a power and/or dim state of one or more lights. In some instances, smart wall switches 108 may also control a power state or speed of a fan, such as a ceiling fan. The smart wall plugs 110 may detect occupancy of a room or enclosure and control supply of power to one or more wall plugs (e.g., such that power is not supplied to the plug if nobody is home).

Still further, in some embodiments, the smart-home environment 100 of FIG. 1 includes a plurality of intelligent, multi-sensing, network-connected appliances 112 (hereinafter referred to as "smart appliances 112"), such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. According to embodiments, the network-connected appliances 112 are made compatible with the smart-home environment by cooperating with the respective manufacturers of the appliances. For example, the appliances can be space heaters, window AC units, motorized duct vents, etc. When plugged in, an appliance can announce itself to the smart-home network, such as by indicating what type of appliance it is, and it can automatically integrate with the controls of the smart-home. Such communication by the appliance to the smart home can be facilitated by any wired or wireless communication protocols known by those having ordinary skill in the art. The smart home also can include a variety of non-communicating legacy appliances 140, such as old conventional washer/dryers, refrigerators, and the like which can be controlled, albeit coarsely (ON/OFF), by virtue of the smart wall plugs 110. The smart-home environment 100 can further include a variety of partially communicating legacy appliances 142, such as infrared ("IR") controlled wall air conditioners or other IR-controlled devices, which can be controlled by IR signals provided by the smart hazard detectors 104 or the smart wall switches 108.

Modularity of Smart Devices

According to embodiments, the smart thermostats 102, the smart hazard detectors 104, the smart doorbells 106, the smart wall switches 108, the smart wall plugs 110, and other devices of the smart-home environment 100 are modular and can be incorporated into older and new houses. For example, the devices are designed around a modular platform consisting of two basic components: a head unit and a back plate, which is also referred to as a docking station. Multiple configurations of the docking station are provided so as to be compatible with any home, such as older and newer homes. However, all of the docking stations include a standard head-connection arrangement, such that any head unit can be removably attached to any docking station. Thus, in some embodiments, the docking stations are interfaces that serve as physical connections to the structure and the voltage wiring of the homes, and the interchangeable head units contain all of the sensors, processors, user interfaces, the batteries, and other functional components of the devices.

Many different commercial and functional possibilities for provisioning, maintenance, and upgrade are possible. For example, after years of using any particular head unit, a user will be able to buy a new version of the head unit and simply plug it into the old docking station. There are also many different versions for the head units, such as low-cost versions with few features, and then a progression of increasingly-capable versions, up to and including extremely fancy head units with a large number of features. Thus, it should be appreciated that the various versions of the head units can all be interchangeable, with any of them working when placed into any docking station. This can advantageously encourage sharing and re-deployment of old head units—for example, when an important high-capability head unit, such as a hazard detector, is replaced by a new version of the head unit, then the old head unit can be re-deployed to a backroom or basement, etc. According to embodiments, when first plugged into a docking station, the head unit can ask the user (by 2D LCD display, 2D/3D holographic projection, voice interaction, etc.) a few simple questions such as, "Where am I" and the user can indicate "living room", "kitchen" and so forth.

Remote Control of Smart Devices

By virtue of network connectivity, one or more of the smart-home devices of FIG. 1 can further allow a user to interact with the device even if the user is not proximate to the device. For example, a user can communicate with a device using a computer (e.g., a desktop computer, laptop computer, or tablet) or other portable electronic device (e.g., a smartphone) 166. Herein, all such smartphones, tables, mobile and stationary computers are referred to as "computer" 166. A webpage or app can be configured to receive communications from the user and control the device based on the communications and/or to present information about the device's operation to the user. For example, the user can view a current setpoint temperature for a device and adjust it using a computer 166. The user can be in the structure during this remote communication, or outside the structure.

As discussed, users can control the smart thermostat and other smart devices in the smart-home environment 100 using a computer 166, which as noted above may be a network-connected computer or portable electronic device such as a smartphone or tablet. In some examples, some or all of the occupants (e.g., individuals who live in the home) can register their computer 166 with the smart-home environment 100. Such registration can be made at a central server to authenticate the occupant and/or the device as being associated with the home and to give permission to the occupant to use the device to control the smart devices in the home. An occupant can use their registered computer 166 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that instead of or in addition to registering computers 166, the smart-home environment 100 makes inferences about which individuals live in the home and are therefore occupants and which computers 166 are associated with those individuals. As such, the smart-home environment "learns" who is an occupant and permits the computers 166 associated with those individuals to control the smart devices of the home.

Guest Mode for Thermostat Controls

In some instances, guests desire to control the smart devices. For example, the smart-home environment may receive communication from an unregistered mobile device of an individual inside of the home, where said individual is not recognized as an occupant of the home. Further, for example, a smart-home environment may receive communication from a mobile device of an individual who is known to be or who is registered as a guest.

According to embodiments, a guest-layer of controls can be provided to guests of the smart-home environment 100. The guest-layer of controls gives guests access to basic controls (e.g., a judicially selected subset of features of the smart devices), such as temperature adjustments, but it locks out other functionalities. The guest layer of controls can be thought of as a "safe sandbox" in which guests have limited controls, but they do not have access to more advanced controls that could fundamentally alter, undermine, damage, or otherwise impair the occupant-desired operation of the smart devices. For example, the guest layer of controls may not permit the guest to adjust a heat-pump lockout temperature. In some embodiments, guests also receive alerts, alarms, and other notifications. For example, in the event that a smart hazard detector 104 detects a hazardous condition, such as a dangerous amount of smoke or carbon monoxide, an alert is sent to devices associated with guests, as well as to devices of the registered occupants.

A use case example of this is when a guest is in a smart home, the guest could walk up to the thermostat and turn the dial manually, but the guest may not want to walk around the house "hunting" the thermostat, especially at night while the home is dark and others are sleeping. Further, the guest may not want to go through the hassle of downloading the necessary application to their device for remotely controlling the thermostat. In fact, the guest may not have the home owner's login credentials, etc., and therefore cannot remotely control the thermostat via such an application. Accordingly, according to embodiments of the invention, the guest can open a mobile browser on their mobile device, type a keyword, such as "NEST" into the URL field and tap "Go" or "Search", etc. In response, the device presents the guest with a user interface, such as Thermozilla UI, which allows the guest to move the target temperature between a limited range, such as "65" and "80". As discussed, the user interface provides a guest layer of controls that are limited to basic functions. The guest cannot change the target humidity, modes, or view energy history.

According to embodiments, to enable guests to access the user interface that provides the guest layer of controls, a local webserver is provided that is accessible in the local area network (LAN). It does not require a password, because physical presence inside the home is established reliably enough by the guest's presence on the LAN. In some embodiments, during installation of the smart device, such as the smart thermostat, the home owner is asked if they want to enable a Local Web App (LWA) on the smart device. Business owners will likely say no; home owners will likely say yes. When the LWA option is selected, the smart device broadcasts to the LAN that the above referenced keyword, such as "NEST", is now a host alias for its local web server. Thus, no matter whose home a guest goes to, that same keyword (e.g., "NEST") is always the URL you use to access the LWA, provided the smart device is purchased from the same manufacturer. Further, according to embodiments, if there is more than one smart device on the LAN, the second and subsequent smart devices do not offer to set up another LWA. Instead, they register themselves as target candidates with the master LWA. And in this case the LWA user would be asked which smart device they want to change the temperature on before getting the simplified user interface, such as Thermozilla UI, for the particular smart device they choose.

According to embodiments, a guest layer of controls may also be provided to users by means other than a computer 166. For example, the smart device, such as the smart thermostat, may be equipped with walkup-identification technology (e.g., face recognition, RFID, ultrasonic sensors) that "fingerprints" or creates a "signature" for the occupants of the home. The walkup-identification technology can be the same as or similar to the fingerprinting and signature creating techniques descripted in other sections of this application. In operation, when a person who does not live in the home or is otherwise not registered with the smart home or whose fingerprint or signature is not recognized by the smart home "walks up" to a smart device, the smart device provides the guest with the guest layer of controls, rather than full controls.

As described below, the smart thermostat and other smart devices "learn" by observing occupant behavior. For example, the smart thermostat learns occupants' preferred temperature set-points for mornings and evenings, and it learns when the occupants are asleep or awake, as well as when the occupants are typically away or at home, for example. According to embodiments, when a guest controls the smart devices, such as the smart thermostat, the smart devices do not "learn" from the guest. This prevents the guest's adjustments and controls from affecting the learned preferences of the occupants.

Smart Tv Remote Control

According to some embodiments, a smart television remote control is provided. The smart remote control recognizes occupants by thumbprint, visual identification, RFID, etc., and it recognizes a user as a guest or as someone belonging to a particular class having limited control and access (e.g., child). Upon recognizing the user as a guest or someone belonging to a limited class, the smart remote control only permits that user to view a subset of channels and to make limited adjustments to the settings of the television and other devices. For example, a guest cannot adjust the digital video recorder (DVR) settings, and a child is limited to viewing child-appropriate programming.

According to some embodiments, similar controls are provided for other instruments, utilities, and devices in the house. For example, sinks, bathtubs, and showers may be controlled by smart spigots that recognize users as guests or as children, and therefore prevent water from exceeding a designated temperature.

Mesh Network of Spokesman and Low-Powered Nodes

In some embodiments, in addition to containing processing and sensing capabilities, each of the devices 102, 104, 106, 108, 110, 112, 114, and 116 (and other devices with such capabilities, which may be collectively referred to herein as "smart devices") is capable of data communications and information sharing with any other of the smart devices, as well as to any central server or cloud-computing system or any other device that is network-connected anywhere in the world. The required data communications can be carried out using any of a variety of custom or standard wireless protocols (Wi-Fi, ZigBee, 6LoWPAN, etc.) and/or any of a variety of custom or standard wired protocols (CAT6 Ethernet, HomePlug, etc.)

According to embodiments, all or some of the smart devices can serve as wireless or wired repeaters. For example, a first one of the smart devices can communicate with a second one of the smart device via a wireless router 160. The smart devices can further communicate with each other via a connection to a network, such as the Internet 162. Through the Internet 162, the smart devices can communicate with a central server or a cloud-computing system 164. The central server or cloud-computing system 164 can be associated with a manufacturer, support entity, or service provider associated with the device. For one embodiment, a user may be able to contact customer support using a device itself rather than needing to use other communication means such as a telephone or Internet-connected computer. Certain embodiments can transmit data such as measurements of temperature, light, smoke, CO, sound, motion, control settings, alarm status, actions performed by the smart devices, and the like to cloud-computing system 164 for offline analysis. Further, software updates can be automatically sent from the central server or cloud-computing system 164 to devices (e.g., when available, when purchased, or at routine intervals).

According to embodiments, the smart devices combine to create a mesh network of spokesman and low-power nodes in the smart-home environment 100, where some of the smart devices are "spokesman" nodes and others are "low-powered" nodes. Some of the smart devices in the smart-home environment 100 are battery powered, while others have a regular and reliable power source, such as by connecting to wiring (e.g., to 120V line voltage wires) behind the walls 154 of the smart-home environment. The smart devices that have a regular and reliable power source are referred to as "spokesman" nodes. These nodes are equipped with the capability of using any wireless protocol or manner to facilitate bidirectional communication with any of a variety of other devices in the smart-home environment 100 as well as with the central server or cloud-computing system 164. On the other hand, the devices that are battery powered are referred to as "low-power" nodes. These nodes tend to be smaller than spokesman nodes and can only communicate using wireless protocols that requires very little power, such as Zigbee, 6LoWPAN, etc. Further, some, but not all, low-power nodes are incapable of bidirectional communication. These low-power nodes send messages, but they are unable to "listen". Thus, other devices in the smart-home environment 100, such as the spokesman nodes, cannot send information to these low-power nodes.

As described, the smart devices serve as low-power and spokesman nodes to create a mesh network in the smart-home environment 100. Individual low-power nodes in the smart-home environment regularly send out messages regarding what they are sensing, and the other low-powered nodes in the smart-home environment—in addition to sending out their own messages—repeat the messages, thereby causing the messages to travel from node to node (i.e., device to device) throughout the smart-home environment 100. The spokesman nodes in the smart-home environment 100 are able to "drop down" to low-powered communication protocols to receive these messages, translate the messages to other communication protocols, and send the translated messages to other spokesman nodes and/or the central server or cloud-computing system 164. Thus, the low-powered nodes using low-power communication protocols are able send messages across the entire smart-home environment 100 as well as over the Internet 162 to the central server or cloud-computing system 164. According to embodiments, the mesh network enables the central server or cloud-computing system 164 regularly receive data from all of the smart devices in the home, make inferences based on the data, and send commands back to one of the smart devices to accomplish some of the smart-home objectives descried herein.

As described, the spokesman nodes and some of the low-powered nodes are capable of "listening". Accordingly, users, other devices, and the central server or cloud-computing system 164 can communicate controls to the low-powered nodes. For example, a user can use a computer 166 (e.g., a smartphone or other portable electronic device) to send commands over the Internet to the central server or cloud-computing system 164, which then relays the commands to the spokesman nodes in the smart-home environment 100. The spokesman nodes drop down to a low-power protocol to communicate the commands to the low-power nodes throughout the smart-home environment, as well as to other spokesman nodes that did not receive the commands directly from the central server or cloud-computing system 164.

Smart Nightlight

An example of a low-power node is a smart nightlight 170. In addition to housing a light source, the smart nightlight 170 houses an occupancy sensor, such as an ultrasonic or passive IR sensor, and an ambient light sensor, such as a photoresistor or a single-pixel sensor that measures light in the room. In some embodiments, the smart nightlight 170 is configured to activate the light source when its ambient light sensor detects that the room is dark and when its occupancy sensor detects that someone is in the room. In other embodiments, the smart nightlight 170 is simply configured to activate the light source when its ambient light sensor detects that the room is dark. Further, according to embodiments, the smart nightlight 170 includes a low-power wireless communication chip (e.g., ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly, using the mesh network, from node to node (i.e., smart device to smart device) within the smart-home environment 100 as well as over the Internet 162 to the central server or cloud-computing system 164.

Example Spokesman and Low-Powered Nodes and Uses of Those Nodes in the Mesh Network Other examples of low-powered nodes include battery-powered versions of the smart hazard detectors 104. These smart hazard detectors 104 are often located in an area without access to constant and reliable power and, as discussed in detail below, may include any number and type of sensors, such as smoke/fire/heat sensors, carbon monoxide/dioxide sensors, occupancy/motion sensors, ambient light sensors, temperature sensors, humidity sensors, and the like. Furthermore, smart hazard detectors 104 can send messages that correspond to each of the respective sensors to the other devices and the central server or cloud-computing system 164, such as by using the mesh network as described above.

Examples of spokesman nodes include smart doorbells 106, smart thermostats 102, wired versions of smart hazard detectors 104, smart wall switches 108, and smart wall plugs 110. These devices 102, 104, 106, 108, and 110 are often located near and connected to a reliable power source, and therefore can include more power-consuming components, such as one or more communication chips capable of bidirectional communication in any variety of protocols.

Alarm Repeaters

In some embodiments, these low-powered and spokesman nodes (e.g., devices 102, 104, 106, 108, 110, 112, and 170) can function as "alarm broadcasters" for a hazard-detection system in the smart-home environment. For example, in the even a smart hazard detector 104 detects a hazardous condition, such dangerous amounts of smoke or carbon monoxide, the smart hazard detector 104 sends an alarm message to the central server or cloud-computing system 164, which instructs the other smart devices in the smart-home environment 100 to provide an alarm, alerting occupants to the dangerous condition. Thus, the hazard-detection system could be enhanced by various low-powered and spokesman nodes located throughout the smart-home environment 100, all capable of providing audible or visual alerts. In this example, a user could enhance the safety of the smart-home environment 100 by buying and installing extra smart devices capable of alerting occupants of additional rooms to dangerous conditions.

Lights "Follow" User Through House

In some embodiments, the mesh network can be used to automatically turn on and off lights as a person transitions from room to room. For example, the low-powered and spokesman nodes (e.g., devices 102, 104, 106, 108, 110, 112, and 170) detect the person's movement through the smart-home environment and communicate corresponding messages through the mesh network. Using the messages that indicate which rooms are occupied, the central server or cloud-computing system 164 or some other device activates and deactivates the smart wall switches 108 to automatically provide light as the person moves from room to room in the smart-home environment 100. Further, users may provide pre-configuration information that indicates which smart wall plugs 110 provide power to lamps and other light sources, such as the smart nightlight 170. Alternatively, this mapping of light sources to wall plugs 110 can be done automatically (e.g., the smart wall plugs 110 detect when a light source is plugged into it, and it sends a corresponding message to the central server or cloud-computing system 164). Using this mapping information in combination with messages that indicate which rooms are occupied, the central server or cloud-computing system 164 or some other device activates and deactivates the smart wall plugs 110 that provide power to lamps and other light sources so as to track the person's movement and provide light as the person moves from room to room.

Emergency Exit Lighting

In some embodiments, the mesh network of low-powered and spokesman nodes can be used to provide exit lighting in the event of an emergency. In some instances, to facilitate this, users provide pre-configuration information that indicates exit routes in the smart-home environment 100. For example, for each room in the house, the user provides a map of the best exit route. It should be appreciated that instead of a user providing this information, the central server or cloud-computing system 164 or some other device could automatically determine the routes using uploaded maps, diagrams, architectural drawings of the smart-home house, as well as using a map generated based on positional information obtained from the nodes of the mesh network (e.g., positional information from the devices is used to construct a map of the house). In operation, when an alarm is activated (e.g., when one or more of the smart hazard detector 104 detects smoke and activates an alarm), the central server or cloud-computing system 164 or some other device uses occupancy information obtained from the low-powered and spokesman nodes to determine which rooms are occupied and then turns on lights (e.g., nightlights 170, wall switches 108, wall plugs 110 that power lamps, etc.) along the exit routes from the occupied rooms so as to provide emergency exit lighting.

HVAC Control Algorithms that Follow Occupants and Adjust Accordingly

In many homes, the HVAC or climate control system heats and/or cools some rooms or zones more efficiently than others, thereby causing temperature variations throughout the home. For example, during a heating cycle, the more efficient rooms and zones are heated to warmer temperature than the less efficient rooms or zones. To compensate for disparate temperatures across rooms and zones, users commonly have to manually adjust the temperature setting of the thermostat differently depending on which room or zone in the home the user is currently occupying. For example, in a home where the upstairs is more efficiently heated than the downstairs and where the thermostat is located upstairs, the user has to set the temperature of the upstairs thermostat higher than the desired temperature in order to heat the downstairs to the desired temperature. In this example, to achieve a downstairs temperature of 70° F., the user may have to set the upstairs thermostat to 73° F.

Rather than the user having to manually adjust the thermostat as described above, embodiments of the smart thermostats 102 are further enhanced by logical integration with other low-powered and spokesman nodes in the home according to rules-based inferencing techniques or artificial intelligence techniques for automatically detecting user location in the home and adjusting the thermostat settings accordingly. With reference to the example above, embodiments of the invention detect that the users are downstairs and automatically adjust the upstairs thermostat so as to achieve the desired temperature of 70° F. downstairs.

To accomplish this, according to embodiments, the occupancy- and temperature-sensing capabilities of the smart thermostats 102 are used to track occupant location as well as room and zone temperatures. In these embodiments, the temperature readings from the smart thermostat 102 closest to the occupants' current locations are weighted heaviest. Thus, the smart thermostats 102 will control the HVAC system to heat or cool the locations nearest the occupants to the user-selected temperature, even if this causes other locations in the home to be heated or cooled to temperatures above or below the user-selected temperature. However, embodiments where smart thermostats 102 alone are used to determine occupant location and room and zone temperatures have limited effectiveness in homes that have only a few smart thermostats 102. For example, these embodiments may not be effective in a two-story home with only one smart thermostat 102 because the smart thermostat 102 can only determine occupancy and temperature in the room or zone in which it is installed.

As such, according to some embodiments, occupancy and temperature data obtained from other low-powered and spokesman nodes (e.g., devices 104, 106, 108, 110, 112, and 170), which are often located in many rooms throughout many homes, is used to supplement the occupancy and temperature data obtained by the limited number of smart thermostats 102 often found in home. This enables the smart-home environment 100 to more accurately determine which rooms of the smart home are occupied and to accurately determine the temperature of those rooms at any given time. Upon determining which rooms are occupied, the temperature readings from those rooms are more heavily weighted than the temperature readings from unoccupied rooms when controlling the HVAC system.

An example will now be provided for illustrative purposes. In this example, the smart-home environment 100 includes only one smart thermostat 102 but it also includes multiple smart hazard detectors 104. In this example, no other types of low-powered or spokesman nodes (e.g., devices 106, 108, 110, 112, and 170) are provided in the house. If an occupant is in a room that includes the smart thermostat 102 as well as one of the smart hazard detectors 104, then the temperature reading of the thermostat 102 is weighted the most when determining the temperature of the room. This is in part because the smart thermostat 102 is mounted about five feet from floor, whereas the smart hazard detectors 104 are often mounted on or close to the ceiling, where temperature is different than what occupants actually experience. On the other hand, if the occupant is located in a room that does not have the smart thermostat 102 but it does have one of the smart hazard detectors 104, then the temperature reading of the smart hazard detector 104 is weighted the most. It should be appreciated that instead of or in addition to the smart hazard detectors 104, the home can include other types of low-powered and spokesman nodes (e.g., devices 106, 108, 110, 112, and 170) for gathering occupancy and temperature data for the various rooms of the home.

Using occupancy and temperature data obtained through the mesh network from multiple low-powered and spokesman nodes to adjust HVAC settings can reduce cost and environmental impact, while enhancing occupant comfort. For example, temperature readings from devices located in rooms of the home that are rarely occupied, such as guest rooms, can be largely ignored when the rooms are unoccupied, thereby avoiding the costs and environmental impact of heating and cooling and unoccupied room. However, when the room is occupied, the smart-home environment 100 will account for the temperature readings from the room when controlling the HVAC system, so as to make the occupant of the room comfortable.

In operation, responsive to receiving a desired temperature setting from a user, the smart thermostat 102 controls the HVAC or climate control system so as to achieve the desired temperature in the occupied rooms. To do so, the smart thermostat 102 heats or cools the home so that a weighted average temperature of the home equals the desired temperature. The weighted average temperature is the average temperature of the rooms of the home, where temperature data from occupied rooms is more heavily weighted than temperature data from unoccupied rooms. The more heavily weighted the temperature data from occupied rooms, the more likely the temperature in those rooms matches the desired temperature.

Quiet Time

In many homes, the HVAC system (e.g., hot water, steam, forced air, AC, humidifiers, etc.) are noisy, especially during "transitions", such as shifting from off to on. This noisiness is particularly noticeable when the home is quiet, such as at night when the occupants are sleeping. Accordingly, the smart thermostats 102, according to some embodiments, are configured to minimize HVAC "transitions" when the home is quiet, and especially when occupants are determined to be sleeping. The idea here is that when the home is quiet (e.g., everyone is sleeping), the HVAC system is also quiet. This feature is sometimes referred to herein as "Quiet Time".

According to embodiments, upon sensing that the home is quiet, smart thermostat 102 controls the HVAC system so as to make as little noise as possible. To sense when the home is quiet, according to embodiments, the smart thermostats 102 leverage noise data received from noise sensors of the other smart devices located in the mesh network of the smart-home environment. When the noise level is low, such as below a predetermined noise threshold, the smart thermostat 102 enters a "quiet time" mode, where it "relaxes" the deadband range around the set temperature. Deadband range is the temperature range where the HVAC system is off because the temperature is close enough to the set temperature. For example, if the set temperature is 70 F and the deadband range is 68-72 F, then the heat turns on if temperature drops below 68 F, the AC turns on if temperature rises above 72 F, but neither are on when the temperature is in the deadband range of 68-72 F. "Relaxing" the deadband range makes the range bigger. For example, during "quiet time", the deadband range of 68-72 F could be relaxed to 65-75 F. Thus, the HVAC system will not turn on and off as often.

It should also be appreciated that, in addition to or instead of using noise sensor to determine when the home is "quiet", the smart thermostat 102 can also leverage the motion detection capabilities of the smart devices in the home. For example, motion tends to be associated with noise. Accordingly, when no motion is detected in the home for a period, the smart thermostat 102 can infer that there is no noise in the home and evoke "quiet time".

Further, according to embodiments, the smart thermostats 102 enter "quiet time" mode upon determining that an occupant of the home are sleeping. According to embodiments, to determine that occupants are sleeping, smart-home environment 100 leverages the sensors of the smart devices located in the mesh network of the smart-home environment in combination with rules-based inference engines or artificial intelligence provided at the central server or cloud-computing system 164. According to embodiments, the smart devices in the smart-home environment 100 that happens to be closest to an occupant when that occupant falls asleep transmit a message indicating that the occupant has stopped moving and appears to be sleeping. The message will be transmitted through the mesh network to the smart thermostats 102, which will then enter "quiet time" mode.

Further, according to embodiments, the smart thermostat 102 enters "quiet time" mode according to a schedule, such as between 11:00 PM and 6:00 AM. According to other embodiments, if an occupant wakes in the middle of the night to visit the restroom, the smart thermostat 102 receives information that there is movement in the home and, if the temperature is near the outer limits of the deadband range, the thermostat 102 transitions the HVAC cycle while the occupant is likely still awake.

Enhancing Auto-Away

According to embodiments, occupancy data obtained from the various low-powered and spokesman nodes located throughout the smart-home environment 100 is used to determine when the house is unoccupied and, upon determining that the house is unoccupied, the smart-home environment 100 automatically turns off or reduces operation of the HVAC system to conserve energy and lessen environmental impact. This feature is sometimes referred to herein as "auto away". In some examples, the smart-home environment 100 determines that the home is unoccupied upon receiving no occupancy data from the low-powered and spokesman nodes in the home for the duration of a period of time, such as one hour. In other words, if none of the low-powered or spokesman nodes detects any movement in the home during daytime hours for the duration of the period, then the smart-home environment 100 makes an inference that the home is unoccupied and invokes "auto away" to turn off or reduce operation of the HVAC system. User dissatisfaction may occur in instances where the smart-home environment 100 incorrectly infers that the home is unoccupied and improperly invokes "auto away", thereby turning of the HVAC system and allowing the home to rise or fall to uncomfortable temperatures. Accordingly, it is desirable to have algorithms for preventing the smart-home environment 100 from improperly invoking "auto away".

One such algorithm involves learning which routes an occupant takes when exiting the home, and not invoking "auto away" unless the occupant takes one of the learned routes. For example, the smart-home environment 100 can learn that the occupant walks through a particular hallway each time they leave the home. Thus, in an example case, when it is daytime during a weekday when the occupant is typically at work, and even though there is no movement in the house which makes it seem like the house is unoccupied, the smart-home environment 100 nonetheless make an inference that the house is occupied because the occupant did not walk through the particular hallway. In such an example, the occupant could be sick and still in bed. Accordingly, the smart-home environment 100 does not invoke "auto away" and it permits the HVAC system to function normally.

Robots

Further included and illustrated in the exemplary smart-home environment 100 of FIG. 1 are service robots 165 each configured to carry out, in an autonomous manner, any of a variety of household tasks. For some embodiments, the service robots 165 can be respectively configured to perform floor sweeping, floor washing, etc. in a manner similar to that of known commercially available devices such as the ROOMBA™ and SCOOBA™ products sold by iRobot, Inc. of Bedford, Mass. Tasks such as floor sweeping and floor washing can be considered as "away" or "while-away" tasks for purposes of the instant description, as it is generally more desirable for these tasks to be performed when the occupants are not present. For other embodiments, one or more of the service robots 165 are configured to perform tasks such as playing music for an occupant, serving as a localized thermostat for an occupant, serving as a localized air monitor/purifier for an occupant, serving as a localized baby monitor, serving as a localized hazard detector for an occupant, and so forth, it being generally more desirable for such tasks to be carried out in the immediate presence of the human occupant. For purposes of the instant description, such tasks can be considered as "human-facing" or "human-centric" tasks.

When serving as a localized thermostat for an occupant, a particular one of the service robots 165 can be considered to be facilitating what can be called a "personal comfort-area network" for the occupant, with the objective being to keep the occupant's immediate space at a comfortable temperature wherever that occupant may be located in the home. This can be contrasted with conventional wall-mounted room thermostats, which have the more attenuated objective of keeping a statically-defined structural space at a comfortable temperature. According to one embodiment, the localized-thermostat service robot 165 is configured to move itself into the immediate presence (e.g., within five feet) of a particular occupant who has settled into a particular location in the home (e.g. in the dining room to eat their breakfast and read the news). The localized-thermostat service robot 165 includes a temperature sensor, a processor, and wireless communication components configured such that control communications with the HVAC system, either directly or through a wall-mounted wirelessly communicating thermostat coupled to the HVAC system, are maintained and such that the temperature in the immediate vicinity of the occupant is maintained at their desired level. If the occupant then moves and settles into another location (e.g. to the living room couch to watch television), the localized-thermostat service robot 165 proceeds to move and park itself next to the couch and keep that particular immediate space at a comfortable temperature.

Technologies by which the localized-thermostat service robot 165 (and/or the larger smart-home system of FIG. 1) can identify and locate the occupant whose personal-area space is to be kept at a comfortable temperature can include, but are not limited to, RFID sensing (e.g., person having an RFID bracelet, RFID necklace, or RFID key fob), synthetic vision techniques (e.g., video cameras and face recognition processors), audio techniques (e.g., voice, sound pattern, vibration pattern recognition), ultrasound sensing/imaging techniques, and infrared or near-field communication (NFC) techniques (e.g., person wearing an infrared or NFC-capable smartphone), along with rules-based inference engines or artificial intelligence techniques that draw useful conclusions from the sensed information (e.g., if there is only a single occupant present in the home, then that is the person whose immediate space should be kept at a comfortable temperature, and the selection of the desired comfortable temperature should correspond to that occupant's particular stored profile).

When serving as a localized air monitor/purifier for an occupant, a particular service robot 165 can be considered to be facilitating what can be called a "personal health-area network" for the occupant, with the objective being to keep the air quality in the occupant's immediate space at healthy levels. Alternatively or in conjunction therewith, other health-related functions can be provided, such as monitoring the temperature or heart rate of the occupant (e.g., using finely remote sensors, near-field communication with on-person monitors, etc.). When serving as a localized hazard detector for an occupant, a particular service robot 165 can be considered to be facilitate what can be called a "personal safety-area network" for the occupant, with the objective being to ensure there is no excessive carbon monoxide, smoke, fire, etc., in the immediate space of the occupant. Methods analogous to those described above for personal comfort-area networks in terms of occupant identifying and tracking are likewise applicable for personal health-area network and personal safety-area network embodiments.

According to some embodiments, the above-referenced facilitation of personal comfort-area networks, personal health-area networks, personal safety-area networks, and/or other such human-facing functionalities of the service robots 165, are further enhanced by logical integration with other smart sensors in the home according to rules-based inferencing techniques or artificial intelligence techniques for achieving better performance of those human-facing functionalities and/or for achieving those goals in energy-conserving or other resource-conserving ways. Thus, for one embodiment relating to personal health-area networks, the air monitor/purifier service robot 165 can be configured to detect whether a household pet is moving toward the currently settled location of the occupant (e.g., using on-board sensors and/or by data communications with other smart-home sensors along with rules-based inferencing/artificial intelligence techniques), and if so, the air purifying rate is immediately increased in preparation for the arrival of more airborne pet dander. For another embodiment relating to personal safety-area networks, the hazard detector service robot 165 can be advised by other smart-home sensors that temperature and humidity levels are rising in the kitchen, which is nearby to the occupant's current dining room location, and responsive to this advisory the hazard detector service robot 165 may temporarily raise a pre-hazard detection threshold, such as a smoke detection pre-hazard threshold, under an inference that any small increases in ambient smoke levels will most likely be due to cooking activity and not due to a genuinely hazardous condition.

The above-described "human-facing" and "away" functionalities can be provided, without limitation, by multiple distinct service robots 165 having respective dedicated ones of such functionalities, by a single service robot 165 having an integration of two or more different ones of such functionalities, and/or any combinations thereof (including the ability for a single service robot 165 to have both "away" and "human facing" functionalities) without departing from the scope of the present teachings. Electrical power can be provided by virtue of rechargeable batteries or other rechargeable methods, with FIG. 1 illustrating an exemplary out-of-the-way docking station 164 to which the service robots 165 will automatically dock and recharge its batteries (if needed) during periods of inactivity. Each service robot 165 may include wireless communication components that facilitate data communications with one or more of the other wirelessly communicating smart-home sensors of FIG. 1 and/or with one or more other service robots 165 (e.g., using Wi-Fi, Zigbee, Z-Wave, 6LoWPAN, etc.), and one or more of the smart-home devices of FIG. 1 can be in communication with a remote server over the Internet. Alternatively or in conjunction therewith, each service robot 165 can be configured to communicate directly with a remote server by virtue of cellular telephone communications, satellite communications, 3G/4G network data communications, or other direct communication method.

Provided according to some embodiments are systems and methods relating to the integration of the service robot(s) 165 with home security sensors and related functionalities of the smart-home system. The embodiments are particularly applicable and advantageous when applied for those service robots 165 that perform "away" functionalities or that otherwise are desirable to be active when the home is unoccupied (hereinafter "away-service robots"). Included in the embodiments are methods and systems for ensuring that home security systems, intrusion detection systems, and/or occupancy-sensitive environmental control systems (for example, occupancy-sensitive automated setback thermostats that enter into a lower-energy-using condition when the home is unoccupied) are not erroneously triggered by the away-service robots.

Provided according to one embodiment is a home automation and security system (e.g., as shown in FIG. 1) that is remotely monitored by a monitoring service by virtue of automated systems (e.g., cloud-based servers or other central servers, hereinafter "central server") that are in data communications with one or more network-connected elements of the home automation and security system. The away-service robots are configured to be in operative data communication with the central server, and are configured such that they remain in a non-away-service state (e.g., a dormant state at their docking station) unless permission is granted from the central server (e.g., by virtue of an "away-service-OK" message from the central server) to commence their away-service activities. An away-state determination made by the system, which can be arrived at (i) exclusively by local on-premises smart device(s) based on occupancy sensor data, (ii) exclusively by the central server based on received occupancy sensor data and/or based on received proximity-related information such as GPS coordinates from user smartphones or automobiles, or (iii) any combination of (i) and (ii) can then trigger the granting of away-service permission to the away-service robots by the central server. During the course of the away-service robot activity, during which the away-service robots may continuously detect and send their in-home location coordinates to the central server, the central server can readily filter signals from the occupancy sensing devices to distinguish between the away-service robot activity versus any unexpected intrusion activity, thereby avoiding a false intrusion alarm condition while also ensuring that the home is secure. Alternatively or in conjunction therewith, the central server may provide filtering data (such as an expected occupancy-sensing profile triggered by the away-service robots) to the occupancy sensing nodes or associated processing nodes of the smart home, such that the filtering is performed at the local level. Although somewhat less secure, it would also be within the scope of the present teachings for the central server to temporarily disable the occupancy sensing equipment for the duration of the away-service robot activity.

According to another embodiment, functionality similar to that of the central server in the above example can be performed by an on-site computing device such as a dedicated server computer, a "master" home automation console or panel, or as an adjunct function of one or more of the smart-home devices of FIG. 1. In such an embodiment, there would be no dependency on a remote service provider to provide the "away-service-OK" permission to the away-service robots and the false-alarm-avoidance filtering service or filter information for the sensed intrusion detection signals.

According to other embodiments, there are provided methods and systems for implementing away-service robot functionality while avoiding false home security alarms and false occupancy-sensitive environmental controls without the requirement of a single overall event orchestrator. For purposes of the simplicity in the present disclosure, the home security systems and/or occupancy-sensitive environmental controls that would be triggered by the motion, noise, vibrations, or other disturbances of the away-service robot activity are referenced simply as "activity sensing systems," and when so triggered will yield a "disturbance-detected" outcome representative of the false trigger (for example, an alarm message to a security service, or an "arrival" determination for an automated setback thermostat that causes the home to be heated or cooled to a more comfortable "occupied" setpoint temperature). According to one embodiment, the away-service robots are configured to emit a standard ultrasonic sound throughout the course of their away-service activity, the activity sensing systems are configured to detect that standard ultrasonic sound, and the activity sensing systems are further configured such that no disturbance-detected outcome will occur for as long as that standard ultrasonic sound is detected. For other embodiments, the away-service robots are configured to emit a standard notification signal throughout the course of their away-service activity, the activity sensing systems are configured to detect that standard notification signal, and the activity sensing systems are further configured such that no disturbance-detected outcome will occur for as long as that standard notification signal is detected, wherein the standard notification signal comprises one or more of: an optical notifying signal; an audible notifying signal; an infrared notifying signal; an infrasonic notifying signal; a wirelessly transmitted data notification signal (e.g., an IP broadcast, multicast, or unicast notification signal, or a notification message sent in an TCP/IP two-way communication session).

According to some embodiments, the notification signals sent by the away-service robots to the activity sensing systems are authenticated and encrypted such that the notifications cannot be learned and replicated by a potential burglar. Any of a variety of known encryption/authentication schemes can be used to ensure such data security including, but not limited to, methods involving third party data security services or certificate authorities. For some embodiments, a permission request-response model can be used, wherein any particular away-service robot requests permission from each activity sensing system in the home when it is ready to perform its away-service tasks, and does not initiate such activity until receiving a "yes" or "permission granted" message from each activity sensing system (or from a single activity sensing system serving as a "spokesman" for all of the activity sensing systems). One advantage of the described embodiments that do not require a central event orchestrator is that there can (optionally) be more of an arms-length relationship between the supplier(s) of the home security/environmental control equipment, on the one hand, and the supplier(s) of the away-service robot(s), on the other hand, as it is only required that there is the described standard one-way notification protocol or the described standard two-way request/permission protocol to be agreed upon by the respective suppliers.

According to still other embodiments, the activity sensing systems are configured to detect sounds, vibrations, RF emissions, or other detectable environmental signals or "signatures" that are intrinsically associated with the away-service activity of each away-service robot, and are further configured such that no disturbance-detected outcome will occur for as long as that particular detectable signal or environmental "signature" is detected. By way of example, a particular kind of vacuum-cleaning away-service robot may emit a specific sound or RF signature. For one embodiment, the away-service environmental signatures for each of a plurality of known away-service robots are stored in the memory of the activity sensing systems based on empirically collected data, the environmental signatures being supplied with the activity sensing systems and periodically updated by a remote update server. For another embodiment, the activity sensing systems can be placed into a "training mode" for the particular home in which they are installed, wherein they "listen" and "learn" the particular environmental signatures of the away-service robots for that home during that training session, and thereafter will suppress disturbance-detected outcomes for intervals in which those environmental signatures are heard.

For still another embodiment, which is particularly useful when the activity sensing system is associated with occupancy-sensitive environmental control equipment rather than a home security system, the activity sensing system is configured to automatically learn the environmental signatures for the away-service robots by virtue of automatically performing correlations over time between detected environmental signatures and detected occupancy activity. By way of example, for one embodiment an intelligent automated nonoccupancy-triggered setback thermostat such as the Nest Learning Thermostat can be configured to constantly monitor for audible and RF activity as well as to perform infrared-based occupancy detection. In particular view of the fact that the environmental signature of the away-service robot will remain relatively constant from event to event, and in view of the fact that the away-service events will likely either (a) themselves be triggered by some sort of nonoccupancy condition as measured by the away-service robots themselves, or (b) occur at regular times of day, there will be patterns in the collected data by which the events themselves will become apparent and for which the environmental signatures can be readily learned. Generally speaking, for this automatic-learning embodiment in which the environmental signatures of the away-service robots are automatically learned without requiring user interaction, it may be useful for a certain number of false triggers to be tolerable over the course of the learning process. Accordingly, this automatic-learning embodiment may be advantageously applied in occupancy-sensitive environmental control equipment (such as an automated setback thermostat) rather than home security systems for the reason that a few false occupancy determinations may cause a few instances of unnecessary heating or cooling, but will not otherwise have any serious consequences, whereas false home security alarms may have more serious consequences.

Smart Alarm Clock—Detecting when Occupant Falls Asleep

According to embodiments, technologies including the sensors of the smart devices located in the mesh network of the smart-home environment in combination with rules-based inference engines or artificial intelligence provided at the central server or cloud-computing system 164 are used to provide a personal "smart alarm clock" for individual occupants of the home. For example, user-occupants can communicate with the central server or cloud-computing system 164 via their computers 166 to access an interface for the smart alarm clock. There, occupants can turn on their "smart alarm clock" and input a wake time for the next day and/or for additional days. In some embodiments, the occupant may have the option of setting a specific wake time for each day of the week, as well as the option of setting some or all of the inputted wake times to "repeat". Artificial intelligence will be used to consider the occupant's response to these alarms when they go off and make inferences about the user's preferred sleep patterns over time.

According to embodiments, the smart device in the smart-home environment 100 that happens to be closest to the occupant when the occupant falls asleep will be the device that transmits messages regarding when the occupant stopped moving, from which the central server or cloud-computing system 164 will make inferences about where and when the occupant prefers to sleep. This closest smart device will as be the device that sounds the alarm to wake the occupant. In this manner, the "smart alarm clock" will follow the occupant throughout the house, by tracking the individual occupants based on their "unique signature", which is determined based on data obtained from sensors located in the smart devices. For example, the sensors include ultrasonic sensors, passive IR sensors, and the like. The unique signature is based on a combination of walking gate, patterns of movement, voice, height, size, etc. It should be appreciated that facial recognition may also be used.

According to an embodiment, the wake times associated with the "smart alarm clock" are used by the smart thermostat 102 to control the HVAC in an efficient manner so as to pre-heat or cool the house to the occupant's desired "sleeping" and "awake" temperature settings. The preferred settings can be learned over time, such as by observing which temperature the occupant sets the thermostat to before going to sleep and which temperature the occupant sets the thermostat to upon waking up.

According to an embodiment, a device is positioned proximate to the occupant's bed, such as on an adjacent nightstand, and collects data as the occupant sleeps using noise sensors, motion sensors (e.g., ultrasonic, IR, and optical), etc. Data may be obtained by the other smart devices in the room as well. Such data may include the occupant's breathing patterns, heart rate, movement, etc. Inferences are made based on this data in combination with data that indicates when the occupant actually wakes up. For example, if—on a regular basis—the occupant's heart rate, breathing, and moving all increase by 5% to 10%, twenty to thirty minutes before the occupant wakes up each morning, then predictions can be made regarding when the occupant is going to wake. Other devices in the home can use these predictions to provide other smart-home objectives, such as adjusting the smart thermostat 102 so as to pre-heat or cool the home to the occupant's desired setting before the occupant wakes up. Further, these predictions can be used to set the "smart alarm clock" for the occupant, to turn on lights, etc.

Alzheimer's Disease—Monitor Occupant Movement in Home

According to embodiments, technologies including the sensors of the smart devices located throughout the smart-home environment in combination with rules-based inference engines or artificial intelligence provided at the central server or cloud-computing system 164 are used to detect or monitor the progress of Alzheimer's Disease. For example, the unique signatures of the occupants are used to track the individual occupants' movement throughout the smart-home environment 100. This data can be aggregated and analyzed to identify patterns indicative of Alzheimer's. Oftentimes, individuals with Alzheimer's have distinctive patterns of migration in their homes. For example, a person will walk to the kitchen and stand there for a while, then to the living room and stand there for a while, and then back to the kitchen. This pattern will take about thirty minutes, and then the person will repeat the pattern. According to embodiments, the remote servers or cloud computing architectures 164 analyze the person's migration data collected by the mesh network of the smart-home environment to identify such patterns.

Extensible Devices and Services Platform

Figure 2:
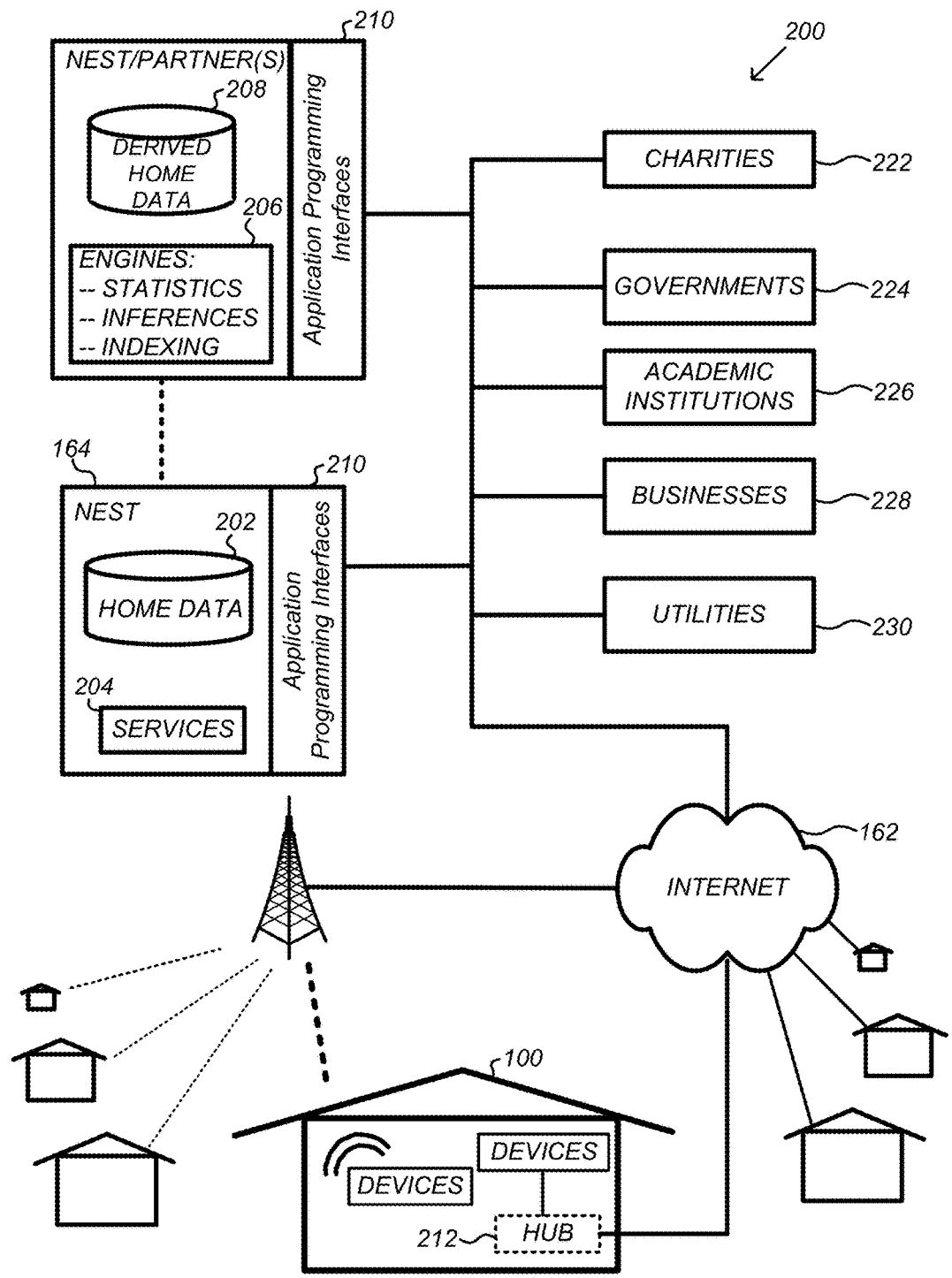
FIG. 2 illustrates a network-level view of an extensible devices and services platform with which the smart-home environment of FIG. 1 can be integrated, according to an embodiment.

FIG. 2 illustrates a network-level view of an extensible devices and services platform 200 with which a plurality of smart-home environments, such as the smart-home environment 100 of FIG. 1, can be integrated. The extensible devices and services platform 200 includes remote servers or cloud computing architectures 164. Each of the intelligent, network-connected devices 102, 104, 106, 108, 110, 112, 114, and 116 from FIG. 1 (identified simply as "smart devices" herein) can communicate with the remote servers or cloud computing architectures 164. For example, a connection to the Internet 162 can be established either directly (for example, using 3G/4G connectivity to a wireless carrier), through a hubbed network 212 (which can be a scheme ranging from a simple wireless router, for example, up to and including an intelligent, dedicated whole-home control node), or through any combination thereof.

Although in some examples provided herein, the devices and services platform 200 communicates with and collects data from the smart devices of smart-home environment 100 of FIG. 1, it should be appreciated that the devices and services platform 200 communicates with and collects data from a plurality of smart-home environments across the world. For example, the central server or cloud-computing system 164 can collect home data 202 from the devices of one or more smart-home environments, where the devices can routinely transmit home data or can transmit home data in specific instances (e.g., when a device queries the home data 202). Thus, the devices and services platform 200 routinely collects data from homes across the world. As described, the collected home data 202 includes, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

According to embodiments, devices in the home increase their logging frequency as they approach a threshold. For example, hazard detector 104 increases the frequency at which it samples air and sends corresponding data to the server 164 as the condition in the home approaches an alarm condition. For example, upon detecting more than a threshold level of smoke, hazard detector 104 samples air at a higher rate and sends corresponding data to the server 164. In another example, hazard detector 104 increases the frequency it samples the air for CO upon detecting a threshold level increase in the amount of CO in the home. Further for example, the devices increase logging and sampling frequency during "transitions". For example, upon detecting increased levels of noise, light, etc. in a location, a device may switch into a "listening" state where sensors such as passive infrared (hereinafter, "PIR") sensors, ultrasonic sensors, etc. sample and log (e.g., send data to server 164) at an increased rate. The increased levels of noise, light, etc. in the location indicates the presence of humans in the room, and thereby indicates that there may be data worth observing in the room. For example, according to embodiments, it may be desirable that the smart devices be quiet most of the time so as to reduce "chatter" on the network (e.g., reduce frequent updates at the server 164). Thus, if no one is in the room, a smart device may be configured to sample once a minute or once an hour. However, if the smart device senses a "transition" indicating that a person is in the room, then it will sample more often. For example, when the room is occupied, the smart device may send to the server 164 temperature data, occupancy data, etc. The server stores this data in home data 202 and runs trend detecting algorithms against the data. For example, the home data 202 may include logs and maps of user in-home movements from room to room, time spent in each room, intra-home occupancy/density maps, etc.

According to embodiments, the home data 202 can be made available to users so that they can review a log of historical events in the home. For example, they can review the historical CO, smoke, temperature, etc. levels of the various rooms of the home. For example, an example historical log indicates: pre-alarm smoke level detected at 10:14 AM; smoke alarm level detected at 10:26 AM; alarm hushed at 10:31; and smoke diminished "everything okay" at 10:50. This enables the user to see that an alarm condition occurred in the home and how it was resolved. The historical log can also include a history of self-checks executed by the smart device. For example, it may show a history of time hazard detectors 104 tested their CO sensors. An example self-check log may indicated that all hazard detectors in the home self-checked between 1 AM and 2 AM, and they are all working properly, including their WiFi connection is good, their battery level is acceptable, their CO sensor is working properly, etc.

The central server or cloud-computing architecture 164 can further provide one or more services 204. The services 204 can include, e.g., software updates, customer support, sensor data collection/logging, remote access, remote or distributed control, or use suggestions (e.g., based on collected home data 202 to improve performance, reduce utility cost, etc.). Data associated with the services 204 can be stored at the central server or cloud-computing system 164 and the central server or the cloud-computing system 164 can retrieve and transmit the data at an appropriate time (e.g., at regular intervals, upon receiving a request from a user, etc.).

As illustrated in FIG. 2, an embodiment of the extensible devices and services platform 200 includes a processing engine 206, which can be concentrated at a single server or distributed among several different computing entities without limitation. The processing engine 206 can include engines configured to receive data from devices of smart-home environments (e.g., via the Internet or a hubbed network), to index the data, to analyze the data and/or to generate statistics based on the analysis or as part of the analysis. The analyzed data can be stored as derived home data 208.

Results of the analysis or statistics can thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings can be generated by the processing engine 206 and transmitted. The results or statistics can be provided via the Internet 162. In this manner, the processing engine 206 can be configured and programmed to derive a variety of useful information from the home data 202. A single server can include one or more engines.

The derived data can be highly beneficial at a variety of different granularities for a variety of useful purposes, ranging from explicit programmed control of the devices on a per-home, per-neighborhood, or per-region basis (for example, demand-response programs for electrical utilities), to the generation of inferential abstractions that can assist on a per-home basis (for example, an inference can be drawn that the homeowner has left for vacation and so security detection equipment can be put on heightened sensitivity), to the generation of statistics and associated inferential abstractions that can be used for government or charitable purposes. For example, processing engine 206 can generate statistics about device usage across a population of devices and send the statistics to device users, service providers or other entities (e.g., that have requested or may have provided monetary compensation for the statistics).

Detection of Sound, Vibration, and/or Motion Created by Running Water

According to some embodiments, sound, vibration, and/or motion sensing components of the smart devices are used to detect sound, vibration, and/or motion created by running water. Based on the detected sound, vibration, and/or motion, the central server or cloud-computing architecture 164 makes inferences about water usage in the home and provides related services. For example, the central server or cloud-computing architecture 164 can run programs/algorithms that recognize what water sounds like and when it is running in the home. According to one embodiment, to map the various water sources of the home, upon detecting running water, the central server or cloud-computing architecture 164 sends a message an occupant's mobile device asking if water is currently running or if water has been recently run in the home and, if so, which room and which water-consumption appliance (e.g., sink, shower, toilet, etc.) was the source of the water. This enables the central server or cloud-computing architecture 164 to determine the "signature" or "fingerprint" of each water source in the home. This is sometimes referred to herein as "audio fingerprinting water usage."

In one illustrative example, the central server or cloud-computing architecture 164 creates a signature for the toilet in the master bathroom, and whenever that toilet is flushed, the central server or cloud-computing architecture 164 will know that the water usage at that time is associated with that toilet. Thus, the central server or cloud-computing architecture 164 can track the water usage of that toilet as well as each water-consumption application in the home. This information can be correlated to water bills or smart water meters so as to provide users with a breakdown of their water usage.

Detection of Sound, Vibration, and/or Motion Created by Mice

According to some embodiments, sound, vibration, and/or motion sensing components of the smart devices are used to detect sound, vibration, and/or motion created by mice and other rodents as well as by termites, cockroaches, and other insects (collectively referred to as "pests"). Based on the detected sound, vibration, and/or motion, the central server or cloud-computing architecture 164 makes inferences about pest-detection in the home and provides related services. For example, the central server or cloud-computing architecture 164 can run programs/algorithms that recognize what certain pests sound like, how they move, and/or the vibration they create, individually and/or collectively. According to one embodiment, the central server or cloud-computing architecture 164 can determine the "signatures" of particular types of pests.

For example, in the event the central server or cloud-computing architecture 164 detects sounds that may be associated with pests, it notifies the occupants of such sounds and suggests hiring a pest control company. If it is confirmed that pests are indeed present, the occupants input to the central server or cloud-computing architecture 164 confirms that its detection was correct, along with details regarding the identified pests, such as name, type, description, location, quantity, etc. This enables the central server or cloud-computing architecture 164 to "tune" itself for better detection and create "signatures" or "fingerprints" for specific types of pests. For example, the central server or cloud-computing architecture 164 can use the tuning as well as the signatures and fingerprints to detect pests in other homes, such as nearby homes that may be experiencing problems with the same pests. Further, for example, in the event that two or more homes in a "neighborhood" are experiencing problems with the same or similar types of pests, the central server or cloud-computing architecture 164 can make inferences that nearby homes may also have such problems or may be susceptible to having such problems, and it can send warning messages to those homes to help facilitate early detection and prevention.

APIs

In some embodiments, to encourage innovation and research and to increase products and services available to users, the devices and services platform 200 expose a range of application programming interfaces (APIs) 210 to third parties, such as charities 222, governmental entities 224 (e.g., the Food and Drug Administration or the Environmental Protection Agency), academic institutions 226 (e.g., university researchers), businesses 228 (e.g., providing device warranties or service to related equipment, targeting advertisements based on home data), utility companies 230, and other third parties. The APIs 210 are coupled to and permit third-party systems to communicate with the central server or the cloud-computing system 164, including the services 204, the processing engine 206, the home data 202, and the derived home data 208. For example, the APIs 210 allow applications executed by the third parties to initiate specific data processing tasks that are executed by the central server or the cloud-computing system 164, as well as to receive dynamic updates to the home data 202 and the derived home data 208.

For example, third parties can develop programs and/or applications, such as web or mobile apps, that integrate with the central server or the cloud-computing system 164 to provide services and information to users. Such programs and application may be, for example, designed to help users reduce energy consumption, to preemptively service faulty equipment, to prepare for high service demands, to track past service performance, etc., or to perform any of a variety of beneficial functions or tasks now known or hereinafter developed.

According to some embodiments, third-party applications make inferences from the home data 202 and the derived home data 208, such inferences may include when are occupants home, when are they sleeping, when are they cooking, when are they in the den watching television, and when do they shower. The answers to these questions may help third-parties benefit consumers by providing them with interesting information, products and services as well as with providing them with targeted advertisements.

In one example, a shipping company creates an application that makes inferences regarding when people are at home. The application uses the inferences to schedule deliveries for times when people will most likely be at home. The application can also build delivery routes around these scheduled times. This reduces the number of instances where the shipping company has to make multiple attempts to deliver packages, and it reduces the number of times consumers have to pick up their packages from the shipping company.

Abstracted Functional View of the Extensible Devices and Services Platform of FIG. 2

Figure 3:
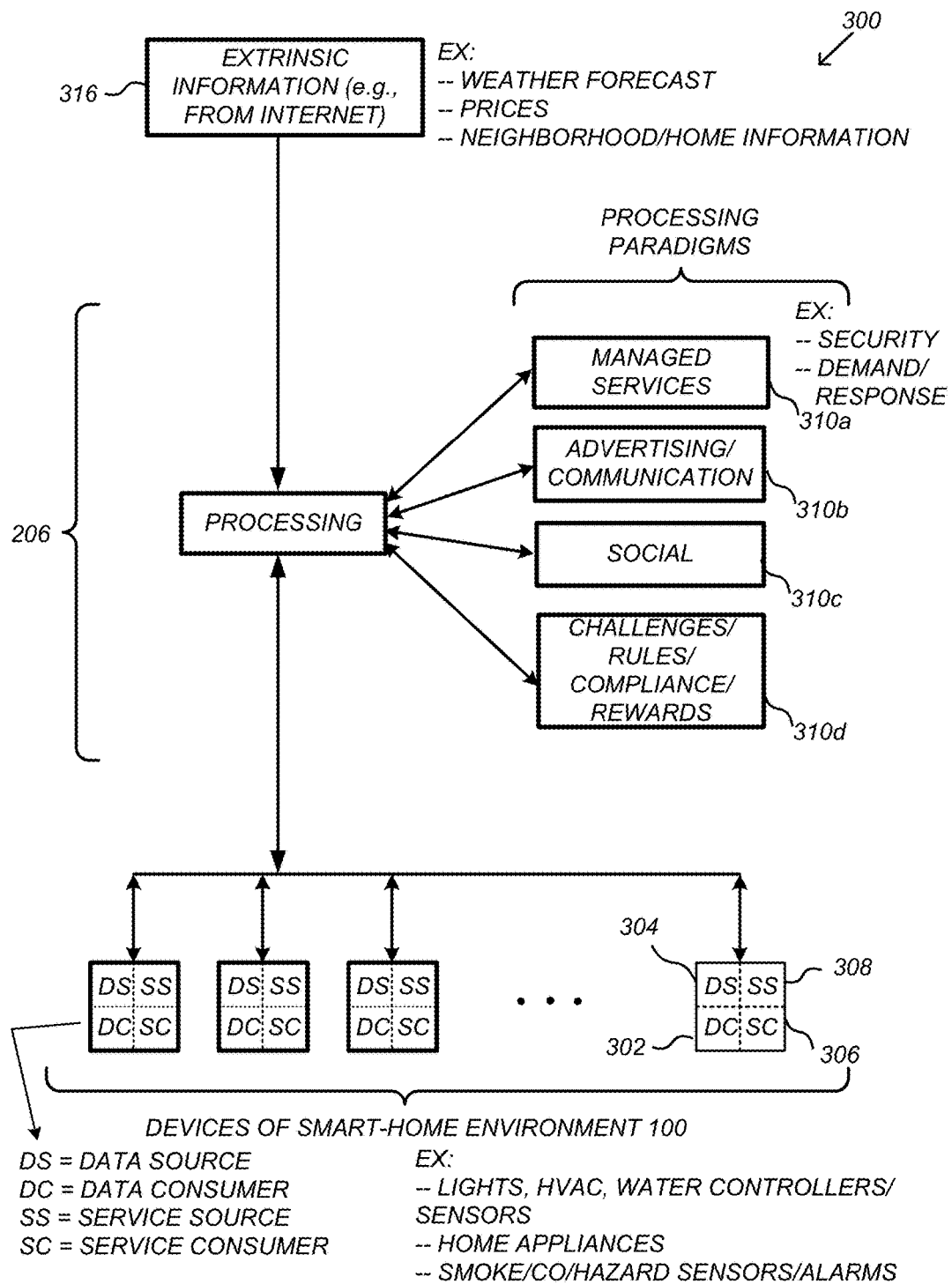
FIG. 3 illustrates an abstracted functional view of the extensible devices and services platform of FIG. 2, with reference to a processing engine as well as devices of the smart-home environment, according to an embodiment.

FIG. 3 illustrates an abstracted functional view of the extensible devices and services platform 200 of FIG. 2, with particular reference to the processing engine 206 as well as devices, such as those of the smart-home environment 100 of FIG. 1. Even though devices situated in smart-home environments will have an endless variety of different individual capabilities and limitations, they can all be thought of as sharing common characteristics in that each of them is a data consumer 302 (DC), a data source 304 (DS), a services consumer 306 (SC), and a services source 308 (SS). Advantageously, in addition to providing the essential control information needed for the devices to achieve their local and immediate objectives, the extensible devices and services platform 200 can also be configured to harness the large amount of data that is flowing out of these devices. In addition to enhancing or optimizing the actual operation of the devices themselves with respect to their immediate functions, the extensible devices and services platform 200 can be directed to "repurposing" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

For example, FIG. 3 shows processing engine 206 as including a number of paradigms 310. Processing engine 206 can include a managed services paradigm 310a that monitors and manages primary or secondary device functions. The device functions can include ensuring proper operation of a device given user inputs, estimating that (e.g., and responding to an instance in which) an intruder is or is attempting to be in a dwelling, detecting a failure of equipment coupled to the device (e.g., a light bulb having burned out), implementing or otherwise responding to energy demand response events, or alerting a user of a current or predicted future event or characteristic. Processing engine 206 can further include an advertising/communication paradigm 310b that estimates characteristics (e.g., demographic information), desires and/or products of interest of a user based on device usage. Services, promotions, products or upgrades can then be offered or automatically provided to the user. Processing engine 206 can further include a social paradigm 310c that uses information from a social network, provides information to a social network (for example, based on device usage), and/or processes data associated with user and/or device interactions with the social network platform. For example, a user's status as reported to their trusted contacts on the social network could be updated to indicate when they are home based on light detection, security system inactivation or device usage detectors. As another example, a user may be able to share device-usage statistics with other users. In yet another example, a user may share HVAC settings that result in low power bills and other users may download the HVAC settings to their smart thermostat 102 to reduce their power bills.

The processing engine 206 can include a challenges/rules/compliance/rewards paradigm 310d that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to promote health (e.g., by reducing exposure to toxins or carcinogens), to conserve money and/or equipment life, etc. For example, one challenge may involve participants turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

The processing engine 206 can integrate or otherwise utilize extrinsic information 316 from extrinsic sources to improve the functioning of one or more processing paradigms. Extrinsic information 316 can be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, etc., to identify statistical or environmental conditions, trends or other information associated with a home or neighborhood, and so forth.

An extraordinary range and variety of benefits can be brought about by, and fit within the scope of, the described extensible devices and services platform 200. Thus, in one example, each bedroom of the smart-home environment 100 can be provided with a smart wall switch 108, a smart wall plug 110, and/or smart hazard detectors 104, all or some of which include an occupancy sensor, wherein the occupancy sensor is also capable of inferring (e.g., by virtue of motion detection, facial recognition, audible sound patterns, etc.) whether the occupant is asleep or awake. If a serious fire event is sensed, the remote security/monitoring service or fire department is advised of how many occupants there are in each bedroom, and whether those occupants are still asleep (or immobile) or whether they have properly evacuated the bedroom.

Hazard Detector Hardware

Figure 4:
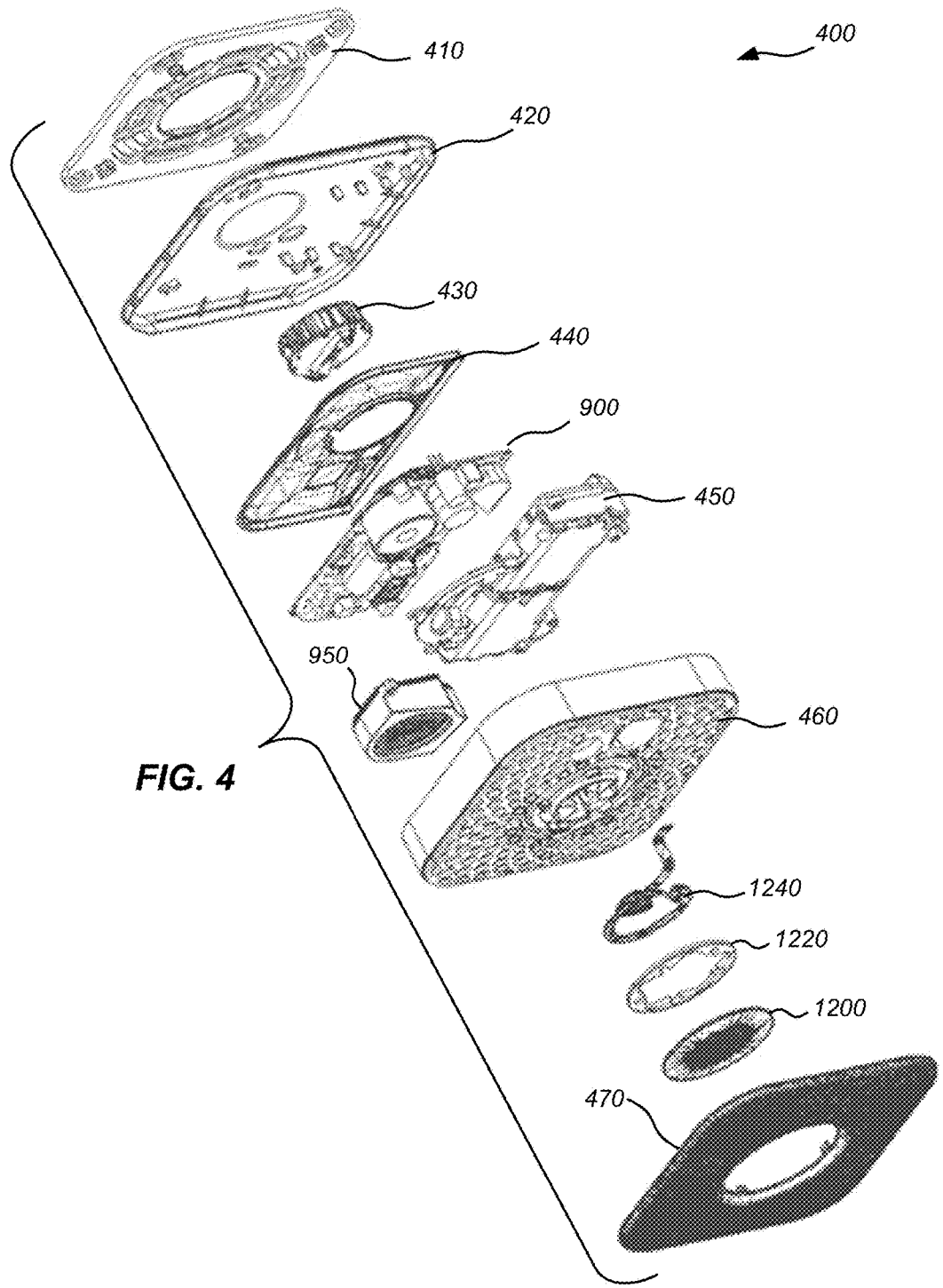
FIG. 4 illustrates a perspective exploded view of an intelligent, multi-sensing, network-connected hazard detector, according to an embodiment.

Referring now to FIG. 4, illustrates an exploded perspective view of a smart hazard detector 104 that may be used as part of a smart-home environment 100 as previously described. According to embodiments, the smart hazard detector 104 corresponds to the smart hazard detector 104 described in other sections of this disclosure, such as in FIG. 1. In one embodiment, hazard detector 104 is a smoke detector that is configured to detect the presence of smoke and sound an alarm to audibly warn an occupant or occupants of the home or structure of a potential fire or other danger. In other embodiments, hazard detector 104 may be a carbon monoxide detector, heat detector, and the like. In one embodiment, hazard detector 104 is a multi-sensing detector that includes a smoke detector, carbon monoxide detector, heat detector, motion detector, and the like. Many of the present teachings are particularly advantageous for embodiments in which the hazard detector 104 is a multi-sensing detector, particularly since combining the various sensing modes together into a single device can pose substantial challenges with respect to one or more of device compactness, component powering, and overall component governance and coordination.

For convenience in describing the embodiments herein, the device 104 will be referred to hereinbelow as smart hazard detector or hazard detector 104, although it should be realized that hazard detector 104 may include various other devices and that the scope of the present teachings is not necessarily limited to hazard detectors in which smoke is required as one of the anomalies to be detected. Thus, for example, depending on the particular context as would be apparent to a person skilled in the art upon reading the instant disclosure, one or more of the advantageous features and embodiments described herein may be readily applicable to a multifunctional hazard sensor that detects carbon monoxide and motion only, or pollen and motion only, or noise pollution and pollen only, and so forth. Nevertheless, the combining of smoke detection functionality with other sensing functions does bring about one or more particularly problematic issues that are addressed by one or more of the present teachings.

In one embodiment, hazard detector 104 is a roughly square or rectangular shaped object having a width of approximately 120 to 134 mm and a thickness of approximately 38 mm. Stated differently, hazard detector 104 is a multi-sensing unit having a fairly compact shape and size that may be easily attached to a wall or ceiling of a home or structure so as to be able, among other functionalities, to detect the presence of smoke and alert an occupant therein of the potential fire danger. As shown in FIG. 4, hazard detector 104 includes a mounting plate 410 that may be attached to a wall of the building or structure to secure the hazard detector 104 thereto. Hazard detector 104 also includes a back plate 420 that may be mounted to the mounting plate 410 and a front casing 460 that may be coupled with or otherwise secured to back plate 420 to define a housing having an interior region within which components of the hazard detector 104 are contained. A circuit board 900 may be coupled with or attached to back plate 420. Various components may be mounted on circuit board 900. For example, a smoke chamber 430 may be coupled with or mounted on circuit board 900 and configured to detect the presence of smoke. In one embodiment, smoke chamber 430 may be mid-mounted relative to circuit board 900 so that air may flow into smoke chamber 430 from a position above circuit board 900 and below circuit board 900.

A speaker 950 and alarm device (not numbered) may also be mounted on circuit board 900 to audibly warn an occupant of a potential fire danger when the presence of smoke is detected via smoke chamber 430. Speaker 950 includes a speaker body and one or more mounting flanges that allow the speaker 950 to be coupled with or mounted on front casing 460. Speaker 950 also includes a plug or other mounting component that allows the speaker 950 to be electrically coupled with circuit board 900. As previously described, speaker 950 may be used to audibly alert an occupant of a room within which hazard detector 104 is positioned, or to provide other messages to the occupant of the room. For example, speaker 950 may be used to alert a firefighter or other rescuer regarding the occupants remaining in the home or structure after a fire or other danger is detected or may be used to inform an occupant of a route out of the home or structure. Other components, such as a motion sensor (e.g., ultrasonic, passive IR, etc.), carbon monoxide sensor, temperature sensor, heat sensor, ambient light sensor, noise sensor, microprocessor, and the like may likewise be mounted on circuit board 900 as described herein.

In one embodiment, a protective plate 440 may be attached to or otherwise coupled with circuit board 900 to provide a visually pleasing appearance to the inner components of hazard detector 104 and/or to funnel or direct airflow to smoke chamber 430. For example, when a user views the internal components of hazard detector 104, such as through vents in back plate 420, protective plate 440 may provide the appearance of a relatively smooth surface and otherwise hide the components or circuitry of circuit board 900. Protective plate 440 may likewise function to direct a flow of air from the vents of back plate 420 toward smoke chamber 430 so as to facilitate air flow into and out of smoke chamber 430.

Hazard detector 104 may also include a battery pack 450 that is configured to provide power to the various components of hazard detector 104 when hazard detector 104 is not coupled with an external power source, such as a 120 V power source of the home or structure. In some embodiments, a cover plate 470 may be coupled with the front casing 460 to provide a visually pleasing appearance to hazard detector 104 and/or for other functional purposes. In a specific embodiment, cover plate 470 may include a plurality of holes or openings that allow one or more sensors coupled with circuit board 900 to view or see through a surface of cover plate 470 so as to sense objects external to hazard detector 104. The plurality of openings of cover plate 470 may be arranged to provide a visually pleasing appearance when viewed by occupants of the home or structure. In one embodiment, the plurality of openings of cover plate 470 may be arranged according to a repeating pattern, such as a Fibonacci or other sequence.

Transparent Lens Button, PIR, Light Ring, Etc.

A lens button 1200 may be coupled with or otherwise mounted to cover plate 470. Lens button 1200 may be attached to the hazard detector 104 so as to be centrally positioned with respect to cover plate 470. Lens button 1200 includes a front surface that faces a room in which the hazard detector 104 is positioned and a rear surface that is opposite the front surface. Lens button 1200 provides a visually appealing surface that may be pressed by a user to provide input to hazard detector 104 and/or for various other purposes, such as quieting an alarm device. Lens button 1200 may also be transparent to one or more sensors positioned behind lens button 1200, to allow the one or more sensors to view through the lens button 1200 for various purposes. For example, in one embodiment a passive IR sensor (not shown) is positioned behind the lens button 1200 and configured to view external objects through lens button 1200 to detect the presence of an occupant or occupants within the home or structure. In some embodiments, lens button 1200 may also function as a button that is pressable by a user to input various commands to hazard detector 104, such as to shut off an alarm that is triggered in response to a false or otherwise harmless condition.

The rear surface of lens button 1200 may have a Fresnel lensing component or element integrally formed thereon that allows one or more PIR sensors, or another sensor (e.g., CCD camera), positioned behind lens button 1200 to view far into the room in which hazard detector 104 is positioned. Lens button 1200 is typically positioned axially in front of the PIR or other sensor(s) to direct infrared radiation onto the sensor device. The PIR sensor(s) may be communicatively coupled with circuit board 900 to provide information thereto and/or receive information therefrom. Further, the Fresnel lens element is formed on the rear surface of lens button 1200 so as to be hidden from external view. Lens button 1200 provides a visually pleasing contour that may match a contour of an exterior of cover plate so that when coupled with cover plate, lens button 1200 and cover plate have a visually continuous contour. Similarly, the Fresnel lens element may be contour-matched to a contour of the rear surface of lens button 1200. The Fresnel lens element may be made from a high-density polyethylene (HDPE) that has an infrared transmission range appropriate for sensitivity to human bodies.

In one embodiment, the Fresnel lens element may include a plurality of concentrically arranged rings that each include a plurality of lenslets and that each provide a slightly different viewing cone. Each concentrically arranged ring may provide a progressively larger viewing area or cone than a concentrically arranged located radially closer to a central axis of lens button 1200. In one embodiment, an internal angle of the viewing cones provided by the Fresnel lens element may vary from between about 15° and about 150° so as to provide a viewing radius on a floor or wall positioned directly in front of the hazard detector 104 at a distance of approximately 10 feet of between about 0.5 m and about 8.8 m. In this manner, the PIR sensor, or other sensor, positioned behind lens button 1200 may easily detect the presence of an occupant within a room in which hazard detector 104 is positioned.

Positioned distally behind lens button 1200 may be a light ring 1220 that is configured to receive light, such as from an LED or another light emitting element, and disperse the light within ring 1220 to provide a desired visual appearance, such as a halo appearance around and behind lens button 1200. Positioned distally behind light ring 1220 may be a flexible circuit board 1240 that includes one or more electrical components, such as a PIR sensor, LEDs, and the like. Flexible circuit board 1240 (hereinafter flex ring 1240) may be electrically coupled with circuit board 900 to communicate and/or receive instructions from one or more microprocessors mounted on a circuit board (not shown) during operation of hazard detector 104. The assembled hazard detector 104 provides a compact yet multifunctional device.

Light Ring Indicates if Everything is Okay or if Attention is Needed

In still another embodiment, the light ring 1220 can provide an indication regarding whether everything is okay or whether something requires the user's attention. For example, the ambient light sensor is used to determine when an occupant turns off the lights in a room, and light ring 1220 glows a particular color or in a particular pattern to indicate that everything is okay or that something needs the occupant's attention. For example, if everything is okay, the light ring 1220 glows green for two seconds. However, if something needs to be addressed, the light ring 1220 glows yellow, for example. This could indicate that hazard detector 104 is improperly placed, the battery is low, there is a properly with the WiFi connection, etc. This yellow glow is not an alarm, but instead is just a warning that something needs to be addressed.

In some embodiments, the PIR sensor may be replaced with an optical CCD sensor. In such embodiments, the Fresnel lens may be a true optical imaging lens for light in the visible spectrum. The CCD sensor may provide optical pictures and/or video of individuals and/or objects within the room and within a field of view of the CCD sensor. The lens may also serve as a user-pressable button. In other embodiments, the PIR sensor, Fresnel lens, and/or CCD sensor may be incorporated in any of a variety of different smart-home devices, such as security cameras, doorbells, garage door openers, entertainment devices, and so forth. Essentially, these components may be incorporated into any device where an occupancy detecting function of a PIR sensor and/or CCD sensor might be useful and where there is a need for a front selectable button. Further, according to embodiments, an ultrasonic occupancy sensor can be used instead of or in addition to the PIR sensor. Still further, according to embodiments, near-field range detection (e.g., BLUETOOTH, NFC, etc.) and/or audio detection using noise sensors can also be used for occupancy detection.

In embodiments, the color of the light ring 1220 of the hazard detector 104 may be adjusted for user enjoyment and/or information based on variables such as time of year and/or hazard status. For example, the produced halo light may glow orange around the Thanksgiving holiday and may glow white each time snow fall occurs in the area. In another embodiment, the color of the light ring 1220 may be adjusted to indicate potential issues within the home, such as a malfunctioning appliance or other component. For example, a smart thermostat may detect an abnormality with the heating system of the home and relay this information to the hazard detector 104. The hazard detector 104 may flash red to indicate to the occupant that a potential issue has been detected and/or to warn the occupant to investigate the potential issue. An email or message may be sent to the occupant by one of the smart-home devices (e.g., smart hazard detector 104, smart thermostat, and the like) to notify the occupant of the detected issue. In some embodiments, the light ring 1220 may flash a number of times, or change color, to indicate the room in which the potential abnormality was detected. For example, the hazard detector 104 could flash once for a first room (e.g., kitchen), twice for a second room (e.g., master bedroom), and the like.

In some embodiments, components in addition to or instead of the PIR sensor may be positioned behind the lens button 1200. For example, in one embodiment a microphone (not shown) may be positioned behind the lens button 1200 or elsewhere on the hazard detector 104. The microphone can be operated to listen to noises that occur within the room in which the hazard detector 104 is positioned. In a specific embodiment, the microphone can be activated and the noise transmitted to another room for various purposes, such as monitoring the activity level of a newborn child or determining if an intruder has entered the home.

Figure 5A:
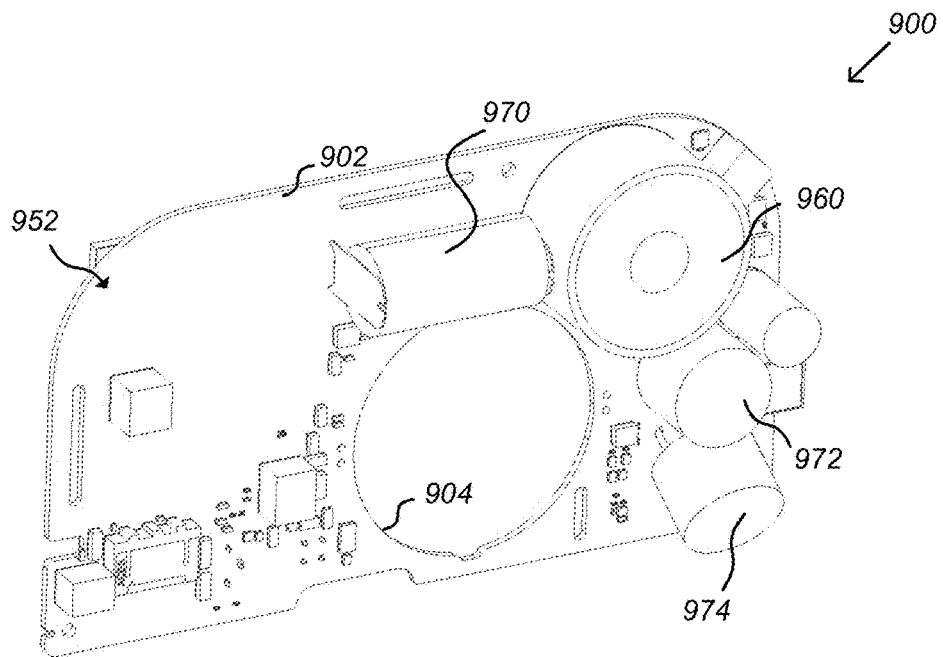
FIGS. 5A and 5B illustrate front and rear perspective views of a circuit board of the hazard detector of FIG. 4, according to an embodiment.
Figure 5B:
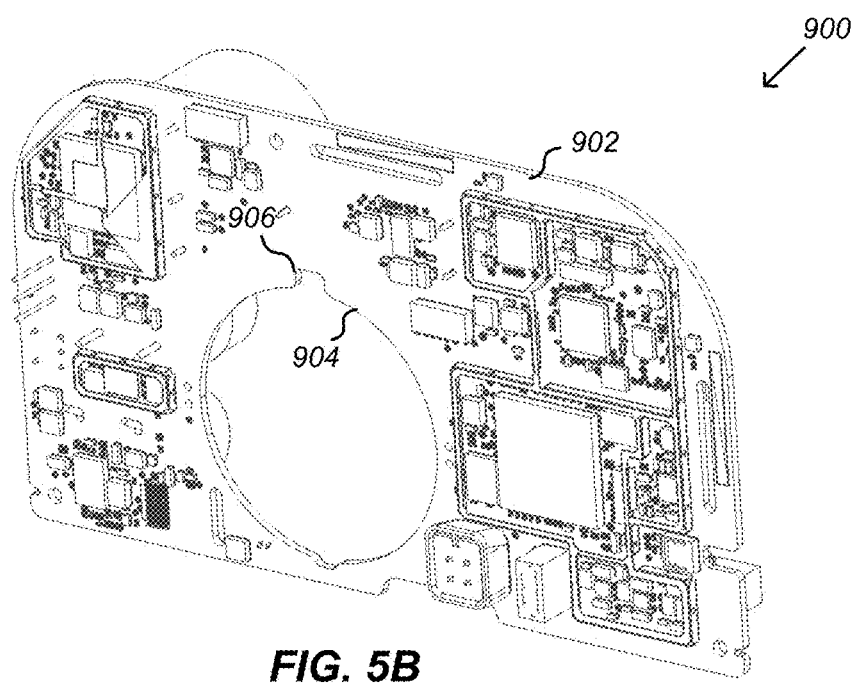

Referring now to FIGS. 5A and 5B, illustrated are front and rear perspective views of circuit board 900. Circuit board 900 includes a main body 902 having a front side or surface and a rear side or surface. As described herein, various electrical components are mounted on circuit board 900. In some embodiments, these components may be mounted on the front surface of circuit board 900, on the rear surface of circuit board 900 opposite the front surface, or on both surfaces of the circuit board 900. For example, in a specific embodiment one or more microprocessors and/or other processor related components may be mounted on the rear surface of circuit board 900 facing protective plate 440 while one or more functional components (e.g. an alarm device, CO detector, speaker, motion sensors, Wi-Fi device, Zigbee device, and the like) are mounted on a front surface of circuit board 900 facing a room of the home or structure in which the hazard detector 104 is positioned. Other components may be mid-mounted relative to circuit board 900 so that opposing surfaces are positioned on opposing sides of the circuit board 900 as described herein.

As shown in FIG. 5A, in a specific embodiment the front surface of circuit board 900 may include a CO detector 970 that is configured to detect the presence of carbon monoxide gas and trigger an alarm device 960 if the carbon monoxide gas levels are determined to be too high. The alarm device 960 (which can be a piezoelectric buzzer having an intentionally shrill or jarring sound) may likewise be mounted on the front surface of circuit board 900 so as to face an occupant of the room in which the hazard detector 104 is positioned to alarm the occupant of a potential danger. Alarm device 960 may be configured to produce one or more sounds or signals to alert the occupant of the potential danger. The front surface may further include an area 952 in which a speaker 950 is positioned. Speaker 950 may be configured to provide audible warnings or messages to the occupant of the room. For example, speaker 950 may alert the occupant of a potential danger and instruct the occupant to exit the room. In some embodiments, speaker 950 may provide specific instructions to the occupant, such as an exit route to use when exiting the room and/or home or structure. Other messages may likewise be communicated to the occupant, such as to alert the occupant that the batteries are low, that CO levels are relatively high in the room, that hazard detector 104 needs periodic cleaning, or alert the occupant of any other abnormalities or issues related to hazard detector 104 or components thereof.

Circuit board 900 may also include one or more motion sensors mounted on the front surface thereof. The motion sensors may be used to determine the presence of an individual within a room or surrounding area of hazard detector 104. This information may be used to change the functionality of hazard detector 104 and/or one or more other devices connected in a common network as described previously. For example, this information may be relayed to a smart thermostat to inform the thermostat that occupants of the home or structure are present so that the smart thermostat may condition the home or structure according to one or more learned or programmed settings. Hazard detector 104 may likewise use this information for one or more purposes, such as to quiet the alarm device (e.g. gesture hush) as described herein or for various other reasons.

In one embodiment, a first ultrasonic sensor 972 and a second ultrasonic sensor 974 may be mounted on the front surface of circuit board 900. The two ultrasonic sensors, 972 and 974, may be offset axially so as to point in slightly different directions. In this orientation, each ultrasonic sensor may be used to detect the motion of an individual based on an orientation of the hazard detector 104 relative to the room and/or occupant. Detecting the motion of the individual may be used to quiet the alarm device as described herein (i.e., gesture hush) or for any other reason. In one embodiment, an axis of the first ultrasonic sensor 972 may be oriented substantially outward relative to hazard detector 104 while an axis of the second ultrasonic sensor 974 is oriented at an angle relative to the axis of first ultrasonic sensor 972. The first ultrasonic sensor 972 may sense motion of an individual when the hazard detector 104 is mounted on a ceiling of the home or structure. Because the first ultrasonic sensor 972 is oriented substantially outward relative to hazard detector 104, the first ultrasonic sensor 972 essentially looks straight down on individuals beneath hazard detector 104. The second ultrasonic sensor 974 may similarly sense motion of the individual when the hazard detector 104 is mounted on a wall of the home or structure. Because the second ultrasonic sensor 974 is oriented at an angle relative to the first ultrasonic sensor 972 and hazard detector 104, the second ultrasonic sensor essentially looks downward toward the floor when the hazard detector 104 is mounted on a wall of the home or structure, rather than looking directly outward as first ultrasonic sensor 972. In one embodiment, the angular offset of the two ultrasonic sensors may be approximately 30° or any other desired value.

In another embodiment, the two ultrasonic sensors, 972 and 974, may be replaced by a single ultrasonic sensor that is configured to rotate within hazard detector 104 so that the single ultrasonic sensor is capable of looking straight outward similar to first ultrasonic sensor 972 or capable of looking downward similar to second ultrasonic sensor 974. The single ultrasonic sensor may be coupled to circuit board 900 via a hinge that allows the ultrasonic sensor to rotate based on the orientation of hazard detector 104. For example, when hazard detector 104 is mounted to a ceiling of the home or structure, gravity may orient the ultrasonic sensor so as to look straight downward; whereas when hazard detector 104 is coupled to a wall of the home or structure, gravity may cause the ultrasonic sensor to rotate via the hinge and look downward toward a floor and relative to hazard detector 104. In another embodiment, a motor may be coupled with the single ultrasonic sensor so as to rotate the ultrasonic sensor based on the orientation of hazard detector 104. In this manner, the ultrasonic sensor may always point in a direction that is likely to detect motion of an individual within the room or space surrounding the hazard detector 104. In yet another embodiment, the single ultrasonic sensor may have a wide field of view that is able to substantially accommodate both mounting positions of the two ultrasonic sensors 972 and 974.

As shown in FIGS. 5A and 5B, body 902 of circuit board 900 also includes a substantially centrally located aperture 904 through which smoke chamber 430 is inserted so as to mid-mount the smoke chamber 430 relative to circuit board 900. Aperture 904 may also include a pair of notches 906 through which wires are inserted to electrically couple the smoke chamber 430 with circuit board 900. As previously described, mid-mounting of the smoke chamber 430 through an aperture 904 allows smoke and air to enter smoke chamber 430 from both the front surface or side of circuit board 900 and the rear surface or side of circuit board 900. Various aspects of the electrical components on the circuit board 900 are now described, the positions thereon of many of which will be apparent to the skilled reader in view of the descriptions herein and FIGS. 5A-5B. Included on the circuit board 900 can be several components, including a system processor, relatively high-power wireless communications circuitry and antenna, relatively low-power wireless communications circuitry and antenna, non-volatile memory, audio speaker 950, one or more interface sensors, a safety processor, safety sensors, alarm device 960, a power source, and powering circuitry. The components are operative to provide safety detection features and user interface features using circuit topology and power budgeting methods that minimize power consumption. According to one preferred embodiment, a bifurcated or hybrid processor circuit topology is used for handling the various features of the hazard detector 104, wherein the safety processor is a relatively small, relatively lean processor that is dedicated to core safety sensor governance and core alarming functionality as would be provided on a conventional smoke/CO alarm, and wherein the system processor is a relatively larger, relatively higher-powered processor that is dedicated to more advanced features such as cloud communications, user interface features, occupancy and other advanced environmental tracking features, and more generally any other task that would not be considered a "core" or "conventional" safety sensing and alarming task.

By way of example and not by way of limitation, the safety processor may be a Freescale KL15 microcontroller, while the system processor may be a Freescale K60 microcontroller. Advantageously, the safety processor is programmed and configured such that it is capable of operating and performing its core safety-related duties regardless of the status or state of the system processor. Thus, for example, even if the system processor is not available or is otherwise incapable of performing any functions, the safety processor will attempt to perform its core tasks such that the hazard detector 104 still meets all industry and/or government safety standards that are required for smoke, CO, and/or other safety-related monitoring for which the hazard detector 104 is offered (provided, of course, that there is sufficient electrical power available for the safety processor to operate). The system processor, on the other hand, performs what might be called "optional" or "advanced" functions that are overlaid onto the functionality of the safety processor, where "optional" or "advanced" refers to tasks that are not specifically required for compliance with industry and/or governmental safety standards. Thus, although the system processor is designed to interoperate with the safety processor to improve the overall performance, feature set, and/or functionality of the hazard detector 104, its operation may not be required in order for the hazard detector 104 to meet industry and/or government safety standards. Being generally a larger and more capable processor than the safety processor, the system processor may consume more power than the safety processor when both are active.

Similarly, when both processors are inactive, the system processor may still consume more power than the safety processor. The system processor can be operative to process user interface features and monitor interface sensors (such as occupancy sensors, audio sensors, cameras, etc., which are not directly related to core safety sensing). For example, the system processor can direct wireless data traffic on both high and low power wireless communications circuitry, access non-volatile memory, communicate with the safety processor, and cause audio to be emitted from speaker 950. As another example, the system processor can monitor interface sensors to determine whether any actions need to be taken (e.g., shut off a blaring alarm in response to a user detected action to hush the alarm). The safety processor may be operative to handle core safety related tasks of the hazard detector 104. The safety processor may poll safety sensors (e.g., smoke, CO) and activate alarm device 960 when one or more of its safety sensors indicate a hazard event is detected, or if another hazard detector 104 broadcasts information of an alarm status requiring an audible alarm (see FIG. 18B). The safety processor may operate independently of the system processor and may activate alarm device 960 regardless of what state the system processor is in. For example, if the system processor is performing an active function (e.g., performing a Wi-Fi update) or is shut down due to power constraints, the safety processor may still activate alarm device 960 when a hazard event is detected.

In some embodiments, the software running on the safety processor may be permanently fixed and may not be updated via a software or firmware update after the hazard detector 104 leaves the factory. Compared to the system processor, the safety processor is a less power consuming processor. Using the safety processor to monitor the safety sensors, as opposed to using the system processor to do this, can yield power savings because safety processor may be constantly monitoring the safety sensors. If the system processor were to constantly monitor the safety sensors, power savings may not be realized. In addition to the power savings realized by using safety processor for monitoring the safety sensors, bifurcating the processors can also ensure that the safety features of the hazard detector 104 always work, regardless of whether the higher level user interface works. The relatively high power wireless communications circuitry can be, for example, a Wi-Fi module capable of communicating according to any of the 802.11 protocols.

By way of example, the relatively high power wireless communications circuitry may be implemented using a Broadcom BCM43362 Wi-Fi module. The relatively low power wireless communications circuitry can be a low power Wireless Personal Area Network (6LoWPAN) module or a ZigBee module capable of communicating according to a 802.15.4 protocol. For example, in one embodiment, the relatively low power wireless communications circuitry may be implemented using an Ember EM357 6LoWPAN module. The non-volatile memory can be any suitable permanent memory storage such as, for example, NAND Flash, a hard disk drive, NOR, ROM, or phase change memory. In one embodiment, the non-volatile memory can store audio clips that can be played back using the speaker 950. The audio clips can include installation instructions or warnings in one or more languages. The interface sensors can includes sensors that are monitored by the system processor, while the safety sensors can include sensors that are monitored by the safety processor.

The interface sensors can include, for example, an ambient light sensor (ALS) (such as can be implemented using a discrete photodiode), a noise sensor, a passive infrared (PIR) motion sensor (such as can be implemented using an Excelitas PYQ1348 module), and one or more ultrasonic sensors (such as can be implemented using one or more Manorshi MS-P1640H12TR modules). The safety sensors can include, for example, the smoke detection chamber 430 (which can employ, for example, an Excelitas IR module), the CO detection module 970 (which can employ, for example, a Figaro TGS5342 sensor), and a temperature and humidity sensor (which can employ, for example, a Sensirion SHT20 module). The power source can supply power to enable operation of the hazard detector and can include any suitable source of energy. Embodiments discussed herein can include AC line power, battery power, a combination of AC line power with a battery backup, and externally supplied DC power (e.g., USB supplied power). Embodiments that use AC line power, AC line power with battery backup, or externally supplied DC power may be subject to different power conservation constraints than battery only embodiments.

Advantageously, battery-only powered embodiments are designed to manage power consumption of a finite energy supply such that hazard detector 104 operates for a minimum period of time of at least seven (7), eight (8), nine (9), or ten (10) years. Line powered embodiments are not as constrained. Line powered with battery backup embodiments may employ power conservation methods to prolong the life of the backup battery. In battery-only embodiments, the power source can include one or more batteries, such as the battery pack 450. The batteries can be constructed from different compositions (e.g., alkaline or lithium iron disulfide) and different end-user configurations (e.g., permanent, user replaceable, or non-user replaceable) can be used. In one embodiment, six cells of Li—$FeS_2$ can be arranged in two stacks of three. Such an arrangement can yield about 27000 mWh of total available power for the hazard detector 104.

Speaker of Hazard Detector as Doorbell

According to embodiments, hazard detector 104 functions as a doorbell charm. For example, hazard detector 104 may communicate via the mesh network with the smart doorbell 106, and receive messages from the smart doorbell 106 regarding when to output a doorbell sound via speaker 950. For example, upon a visitor approaching an exterior door of the smart-home environment 100 and touching, pressing, or otherwise activating the smart doorbell 106, the smart doorbell 106 sends a corresponding message to the hazard detector 104. Upon receiving the message from the smart doorbell 106, the hazard detector 104 determines an appropriate response, which may include outputting the doorbell sound. For example, upon receiving the message the hazard detector 104 may first use its occupancy sensing capabilities to determine if the room or area in which it is located is occupied and, possibly, it may also determine which occupants are in the room using facial recognition techniques as well as other techniques used to identify an individual's "signature".

In some cases, if the room or area is unoccupied, the hazard detector 104 will not output the doorbell sound and it will instead remain silent. In still other cases, hazard detector 104 will not output the doorbell sound if it determines that an occupant is a child, pet, or an adult or child sleeping in the room or area. For example, to determine if an occupant is sleeping in the room, hazard detector 104 may note when an occupant enters the room or area and infer that the occupant is sleeping if the occupant does not leave the room and if there is no movement in the room for a period. As discussed below with reference to FIGS. 13 & 14, according to embodiments, a user can program hazard detector 104 so that it knows its location within the home. For example, hazard detector 104 can know if it is in a kitchen, a bedroom, a living room, etc. In these embodiments, the feature of not outputting the doorbell sound if hazard detector 104 determines that an occupant is in the room sleeping will only be active if the hazard detector knows that it is located in a bedroom. Thus, if hazard detector 104 is located in the living room or the kitchen, it will not first assess if an occupant is asleep in the room before outputting the doorbell sound.

In other embodiments, if hazard detector 104 knows that it is located in a bedroom, it will not output the doorbell sound if the room is occupied. According to these embodiments, hazard detector 104 will not attempt to determine whether the occupant is awake or asleep. This reduces processing burden and saves power, as well as reduces the likelihood of making an error by incorrectly inferring that an occupant is asleep or awake. In still other embodiments, if hazard detector 104 knows that it is in a kid's bedroom, as indicated by the user during set up, it will never output the doorbell sound.

As mentioned above, embodiments of the present invention, e.g., hazard detectors 104, may be paired with an online management account. This pairing may be accomplished during the setup process for a smart hazard detector. Examples of this setup process according to the present invention are discussed in the next section.

Setting Up the Hazard Detector

FIGS. 1-5B above outline numerous features and benefits of intelligent, network-connected, multi-sensing hazard detection units or hazard detectors of the present invention. In order to achieve some of these benefits, smart hazard detectors may need to be set up and/or "paired" with an online management account. Similarly, although not illustrated here, smart thermostats 102 may also be paired with the online management account, as part of a smart thermostat 102 installation process. In particular, when smart thermostat 102 is installed, an installer of smart thermostat 102 may be queried as to a type of heating system is being controlled. In embodiments, smart thermostat stores the answer in memory therein. This is relevant to embodiments herein that control fossil fuel-based heating systems, which may generate CO as a combustion byproduct.

Figure 6:
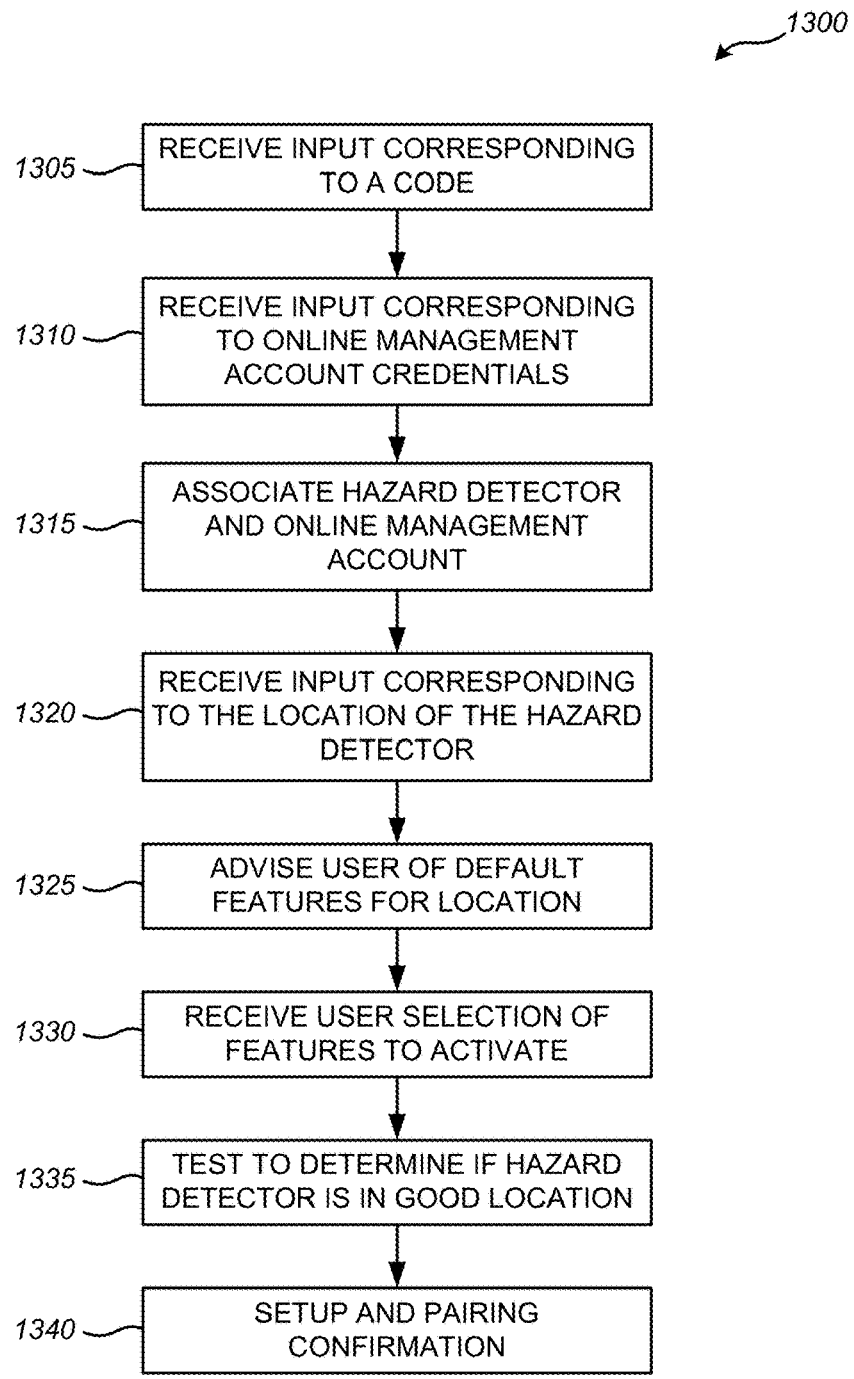
FIG. 6 illustrates a method 1300 for setting up a hazard detector and pairing the hazard detector and an online management account, according to an embodiment.

FIG. 6 illustrates a method 1300 for setting up a hazard detector and establishing a pairing between the hazard detector and an online management account, according to an embodiment. Certain steps of method 1300 are discussed in detail below, and some steps are discussed with reference to additional figures that may provide physical illustrations related to the steps of method 1300. It should be appreciated that method 1300 is an exemplary method of setting up and pairing a hazard detector and that some illustrated steps may not be necessary or applicable, and other, additional steps may be appropriate.

Sending Unique Code for Hazard Detector to Server

At step 1305 of method 1300, a central server or a cloud-computing system, e.g., server 164, may receive input corresponding to a code. This code may be the unique ID of a hazard detector. The code may also be associated with additional information stored on a server, e.g., the hazard detector's manufacture date, the software version that was initially installed on the hazard detector and/or other information about the hazard detector. Before the server can receive this code in step 1305, a user first may need to obtain the code from a hazard detector, e.g., hazard detector 104. The code may be contained in the product packaging of the hazard detector or displayed on the hazard detector and provided to server 164 via an app or a webpage configured to provide communication to server 164.

Receiving User's Account Credentials

At step 1310 of method 1300, a central server or a cloud-computing system, e.g., server 164, may receive input corresponding to credentials for accessing an online management account.

Link Hazard Detector to Online Account

At step 1315, a central server or a cloud-computing system, e.g., server 164, may associate hazard detector 104 and an online management account using a code and credentials for the online management account. This may also allow data, e.g., home data 202, to be collected, stored and linked to and/or accessible at a user's online management account. Additionally, this association may allow for remote access and/or remote or distributed control of hazard detector 104 via a user's online management account. However, in order for data collected from and/or remote control of hazard detector 104 to be possible, hazard detector 104 may need to have a network connection.

Tell Hazard Detector where in the Home it is Located

At step 1320 of method 1300, hazard detector 104 receives user input corresponding to its location within a home or building (e.g., user inputs information that tells hazard detector where it is located). In some embodiments, hazard detector 104 transmits the location information to a central server or a cloud-computing system. The user input could be location information, such as indication of a room type or room name where hazard detector 104 is being installed. The location information could be stored locally on hazard detector and/or at the user's online management account and used to enhance the features of services 204 provided by and to hazard detector 104.

The location information may be used to further configure hazard detector 104. For example, the location of hazard detector 104 may be used to alter the way alerts are provided to users and/or how hazard detector 104 interprets characteristics measured by its sensors. More specifically, for example, hazard detector 104 may account for the environmental characteristics of a kitchen by adjusting alarm threshold to make the hazard detector less sensitive to smoke and heat commonly observed in kitchens. Also for example, hazard detector 104 may account for increased amounts of humidity since higher levels of humidity is a characteristic of kitchens (e.g., higher humidity in kitchen when something is boiling on the stovetop). Further for example, hazard detector 104 may alter the alert or alarm sequence, such as by providing a user more opportunities to preemptively "hush" an alarm for a known, low level smoke condition. In another example, hazard detector 104 may be located in a bedroom. To account for the environmental characteristics of a bedroom, hazard detector 104 may become more sensitive to smoke and CO and/or it may increase its alarm volumes for the purpose of waking up sleeping individuals upon detection of a potentially dangerous condition.

Figure 7:
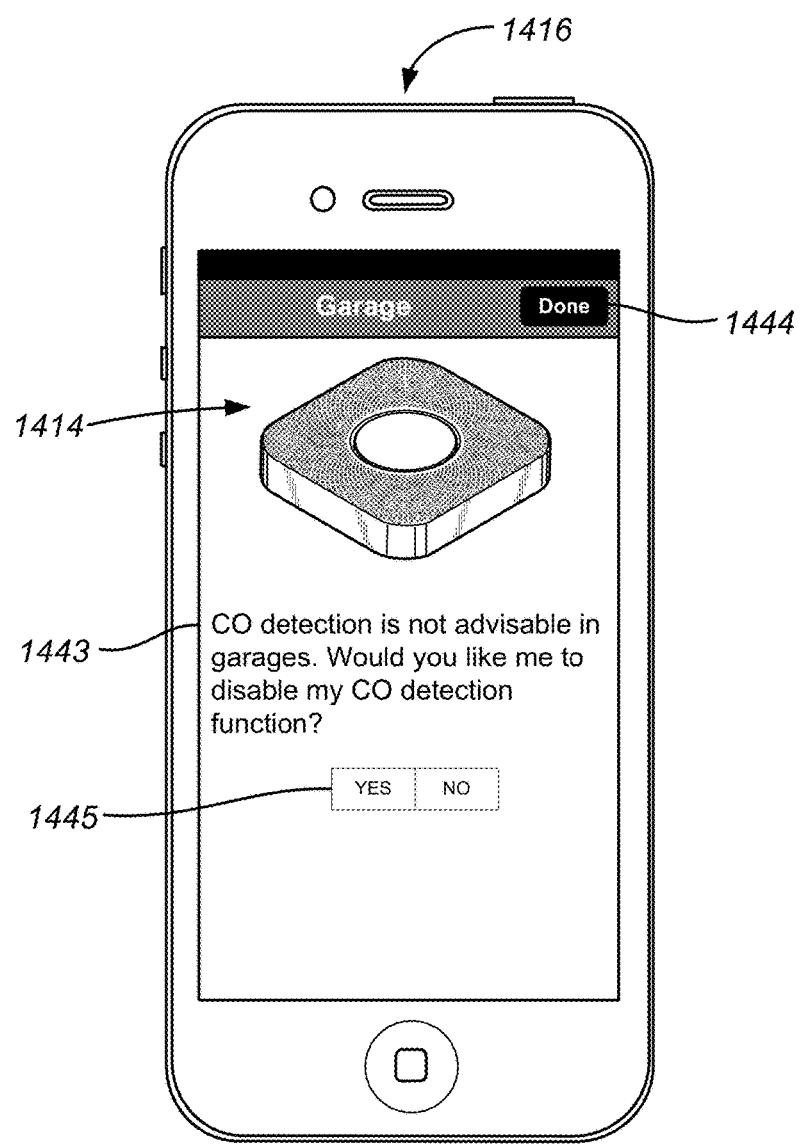
FIGS. 7-11 illustrate examples of the physical process associated with the method of FIG. 6, according to an embodiment.
Figure 8:
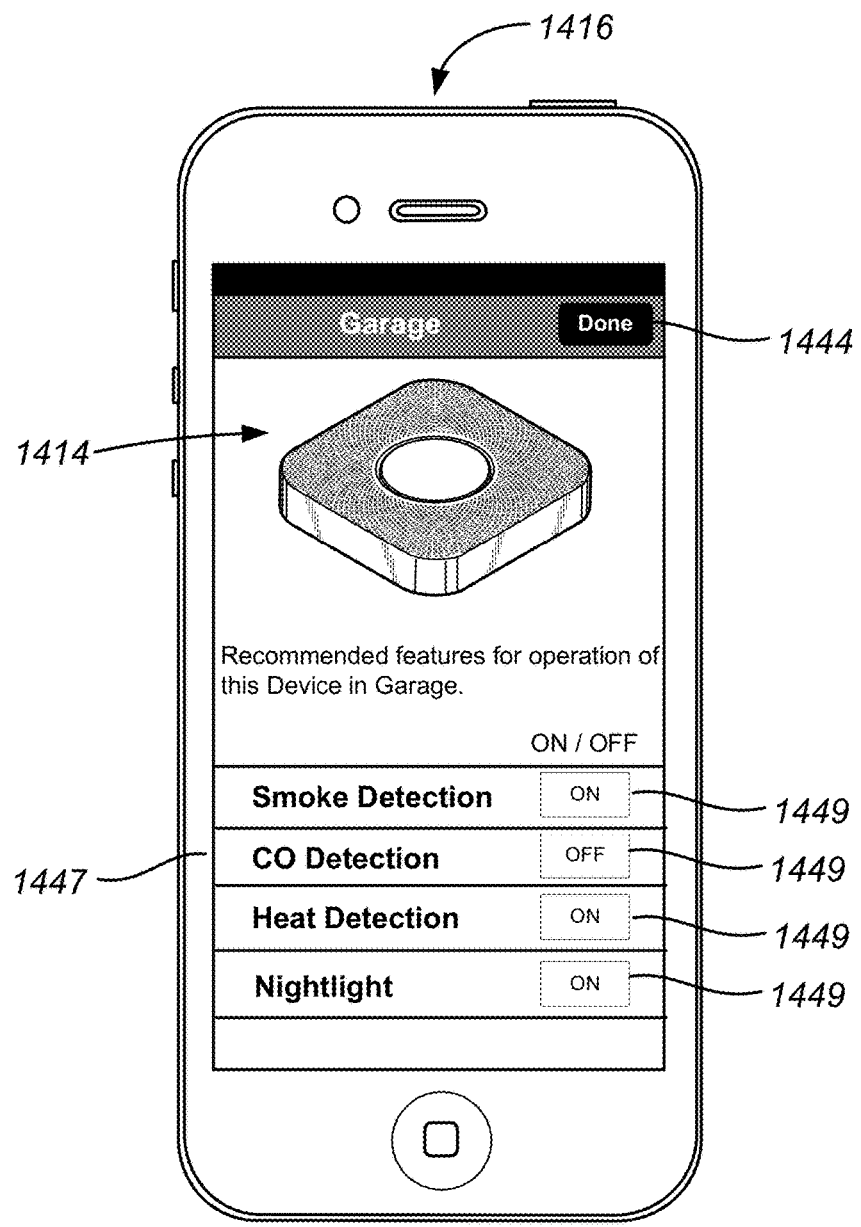

Hazard Detector Advises which Features are Appropriate for its Particular Location At step 1325 of method 1300, a user is advised of recommended settings for hazard detector 104 based on the location of the hazard detector. Some features of hazard detector 104 may not be desirable for some locations and, when installed in those locations, hazard detector 104 can be placed in a limited operation mode in which one or more of those features are disabled. For example, it has been found that garages are inadvisable locations in which to place a CO detector. However, it has also been found that garages are advisable locations in which to place heat detectors. Accordingly, as illustrated in FIG. 7, if the user inputs "Garage" as the location at step 1320, then according to step 1325, application 1414 provides user with a message 1443, informing the user that CO detection is not advisable in garages and giving the user the option of turning off the CO detection function. FIG. 8 illustrates another example of application 1414 providing recommended setting based on the location of the hazard detector. Here, application 1414 provides a list 1447 of recommended settings for the location of the hazard detector 104. As illustrated, application 1414 recommends turning on the smoke detection, heat detection, and nightlight functions, but disabling the CO detection for this hazard detector that is located in a Garage. The user can accept these recommended setting by pressing button 1444, or the user can change the recommended settings by pressing button 1449 next to each of the listed settings to toggle between "off" and "on", and then press button 1449 when the settings are to the user's liking.

Figure 9:
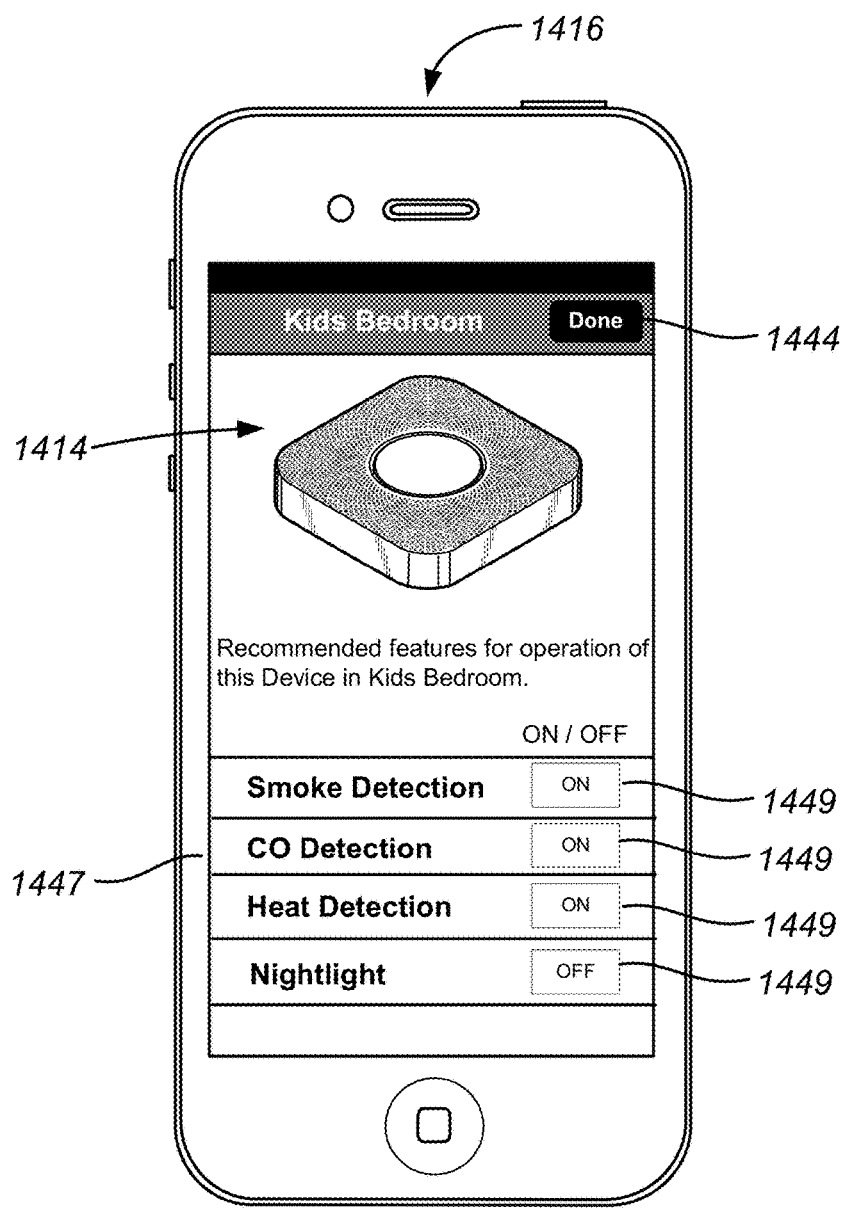

Another example is illustrated in FIG. 9. In this example, the hazard detector 104 is being installed in a Kid's Bedroom. According to the illustrated recommended feature list 1447 for a kid's bedroom, the default setting for the nightlight function is "off", and "on" is the default setting for smoke detection, CO detection, and heat detection. The nightlight is set to "off" so that the light will not disturb people while they are sleeping. However, for other rooms, such as living rooms and kitchens, it should be appreciated that the default setting for the nightlight function is "on".

At step 1330 of method 1300, responsive to being advised of recommended settings for hazard detector 104 based on the location of the hazard detector, the user inputs their selections of which features to turn on and off. As illustrated in FIG. 7, responsive to being advised that CO detection is not recommended in Garages, the user can press button 1445 to answer yes or no to the question of whether to turn off the CO detection function. After selecting user or no the user can press button 1444 to submit the selection. In FIG. 8, responsive to being presented with a list 1447 of recommended functions for a location, user can press buttons 1449 to select which features the user wants turned off or on. The user can then press button 1444 to input the selections.

Hazard Detector Auto-Tests to 'See' if it is in a Bad Location

At step 1335 of method 1300, a test is performed to make sure hazard detector 104 is not installed in a bad location, such as where its sensor are obstructed. According to an embodiment, hazard detector 104 executes a self-test where it uses its ultrasonic sensor(s) to determine its position relative to walls, ceilings, floors, and/or other objects located in the room. For example, hazard detector uses its ultrasound sensor to 'see' if it is located too deep in a corner or behind an obstruction, where it does not have unobstructed access to monitor the conditions of the room, including detecting occupancy of the room. In one embodiment, hazard detector 104 tests to determine whether it is too far in a corner by using its ultrasound sensor to detect whether the perpendicular walls are within a predetermined distance.

Figure 10:
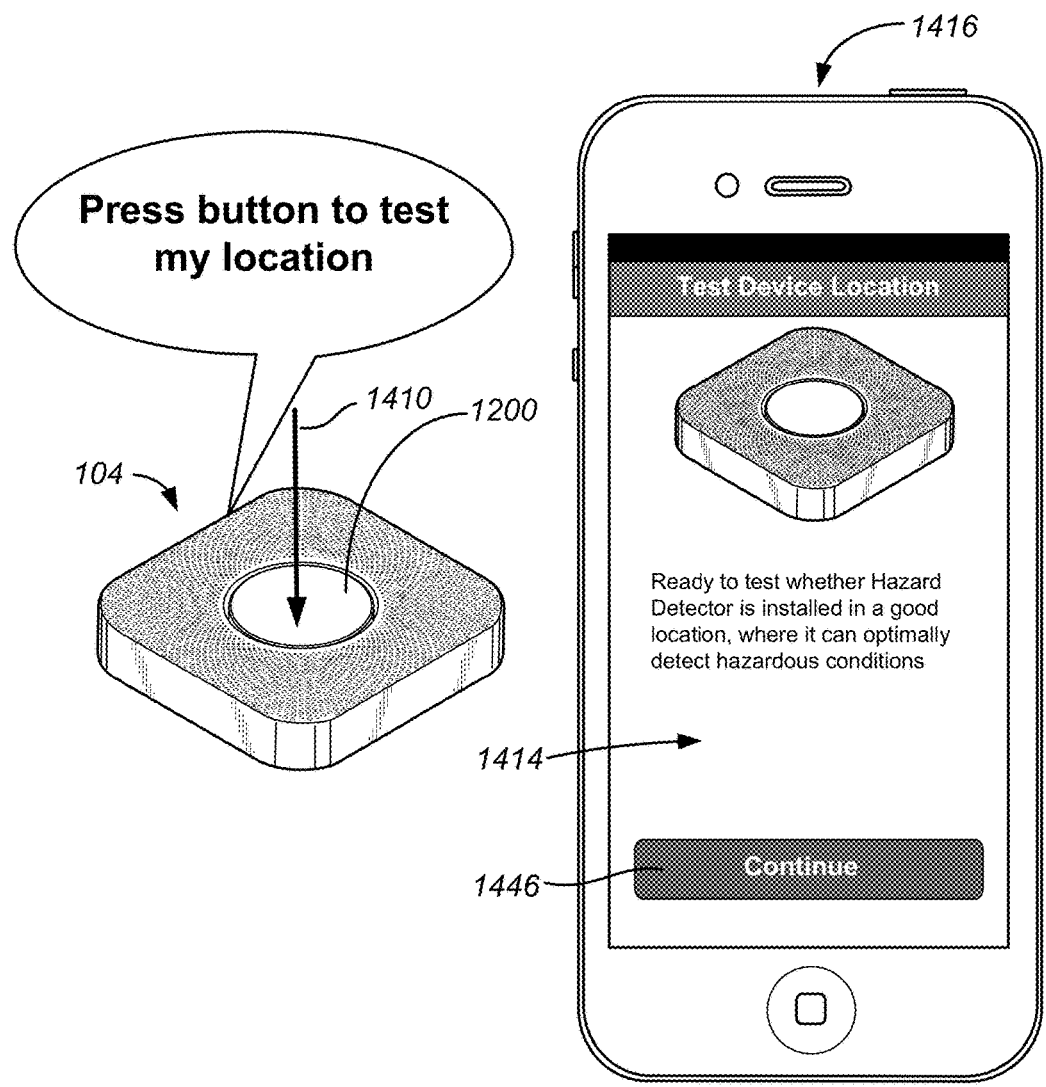

FIG. 10 illustrates an example of the physical process associated with step 1335. An interface may be provided at application 1414 on mobile computing device 1416 to explain that the hazard detect is ready to test whether it is installed in a good location, where it can optimally detect hazardous conditions. In the illustrated example, the user can press button 1446 to begin the test. Also, as illustrated in FIG. 10, hazard detector 104 can output an audible message saying, "Press button to test my location". In response, users can press button 1200 in direction 1410 to begin the test. If the test fails due to hazard detector 104 being position too close to an object, such as a wall, application 1414 will display message, or hazard detector 104 will output a voice message, indicating that hazard detector 104 appears to be too close to an object, such as a wall, and recommending relocation of hazard detector 104 to another position.

Figure 11:
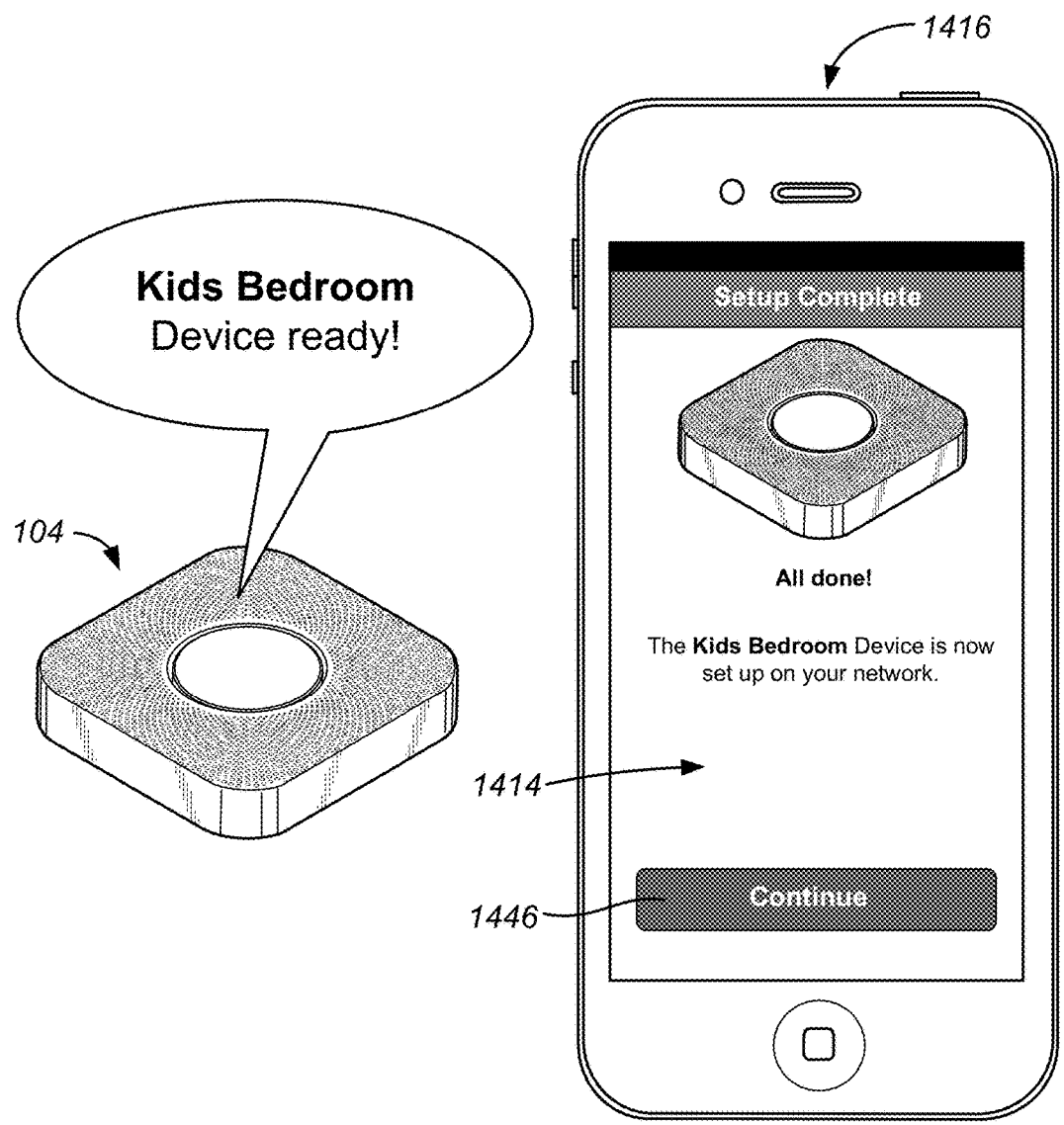

At step 1340 of method 1300, a central server or a cloud-computing system may confirm setup and pairing of hazard detector 104. For example, at step 1340, the application 1414 provides a confirmation message that confirms the pairing association created at step 1310 and the setup selections made at steps 1320 and 1330. FIG. 14R illustrates an example of the physical process associated with step 1340. Application 1414 may display the screen shown in FIG. 11 in order to provide confirmation that the setup for hazard detector 104 is complete. Hazard detector 104 may also generate a corresponding audio and/or visual indicator. For example, as shown in FIG. 11, the hazard detector may generate the following speech when "Kids Bedroom" is the location selected at step 1320: "Kids Bedroom Device ready". Alternatively, hazard detector 104 may generate other audio and/or visual confirmation of the successful association. These confirmations signify that hazard detector 104 has been associated with the selected location at the online management account on sever 164. The user may tap a continue button 1446 to confirm that the confirmation screen has been viewed. Although additional steps may not be required in order to complete the setup of hazard detector 104, the user may still proceed with additional steps to verify hazard detector 104 is functioning properly. An example of this verification process is illustrated in the following figures.

In some embodiments, the input provided at application 1414 during method 1300 may be accomplished using speech recognition, air gestures, eye tracking and blink detection and/or other input means. Again, as mentioned above, the method 1300 may also occur at a webpage of computing device. Furthermore, although the communication between hazard detector 104 and a portable computing device 1416 is described above as occurring over Wi-Fi, other wireless protocols supported by both hazard detector 104 and portable computing device 1416 may be used in the alternative. Also, while a limited number of visual and audio indicators generated by hazard detector 104 were described above, other indicators may also be generated by hazard detector 104 during method 1300.

Setting Up and Pairing Multiple Hazard Detectors in a Single Home

In some situations, a user may wish to add more than one hazard detector to a smart-home environment. In some embodiments, method 1300 may be repeated for each additional hazard detector in order to pair it with the online management account. Alternatively, the method for adding additional hazard detectors may vary from method 1300 in a manner that reduces or minimizes an amount of user effort involved. An example of a method that uses method 1300 to add a first hazard detector, and a modified version of method 1300 to add an additional hazard detector, is shown in FIG. 12.

Figure 12:
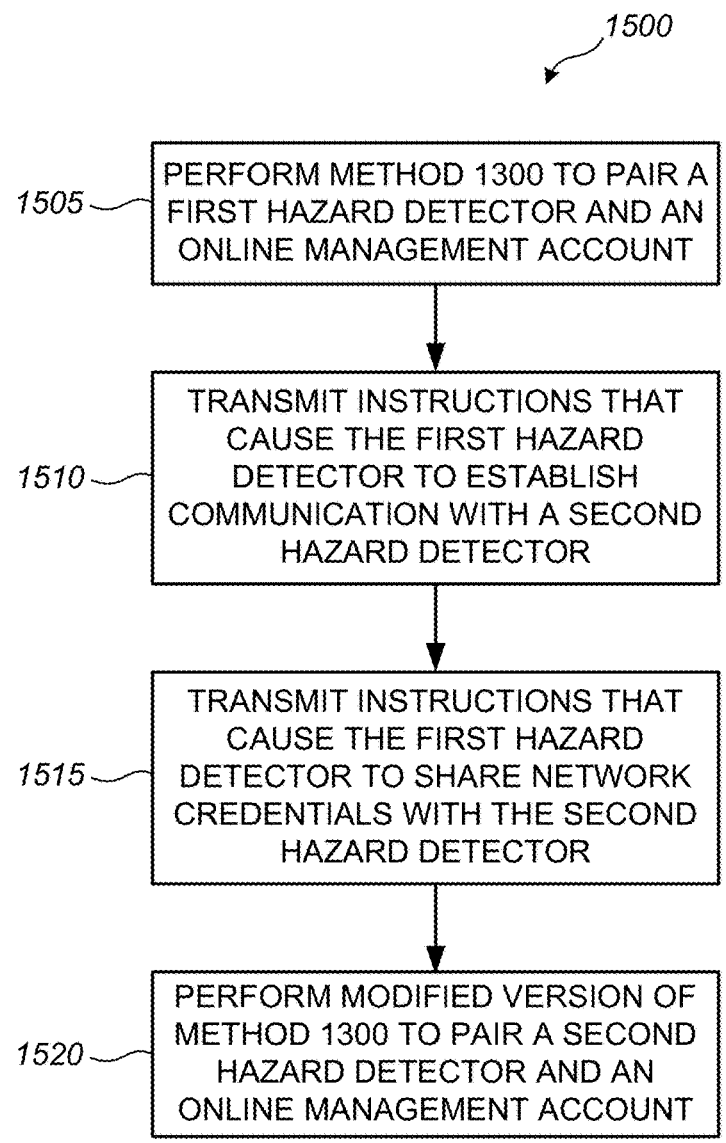
FIG. 12 illustrates a method for pairing two or more hazard detectors and an online management account, according to an embodiment.

FIG. 12 illustrates a method for pairing two or more hazard detectors and an online management account, according to an embodiment. At step 1505 of method 1500, an embodiment of method 1300 may be performed in order to pair a first hazard detector and an online management account.

At step 1510, instructions are transmitted that cause the first hazard detector to establish wireless communication between the first hazard detector and a second hazard detector. To accomplish step 1510, user may open or install and open an app, e.g., application 1414, on a computing device, e.g., computing device 1416. Alternatively, a webpage configured to communicate with the online management account may be used in performing step 1510. Upon opening the app, an option to add another hazard detector, a second hazard detector, may be selected at the app interface. Using a wireless protocol such as Wi-Fi the app may then transmit instructions via a server, e.g., server 164, and internet 162 to the first hazard detector. For example, the first hazard detector may be instructed to broadcast across a 6LoWPAN network, or another wireless protocol that requires very little power, such as Zigbee.

The 6LoWPAN wireless network broadcasted by the first hazard may use a unique network name that may be recognized by other hazard detectors and/or assign itself one or more IPv6 addresses that include a rendezvous prefix. The rendezvous prefix may help hazard detectors to identify the networks it should join. Alternatively, the 6LoWPAN network may be broadcasted in another manner that allows a second hazard detector to recognize it as a network that should be joined. The second hazard detector may also broadcast a 6LoWPAN network in a similar manner. When one hazard detector discovers another hazard detector's 6LoWPAN network, it may terminate its joining network and connect to the network broadcasted by the other hazard detector. Thus, the first hazard detector may join the second hazard detector's network and vice versa. Either way, a wireless communication may be established in this manner between the first hazard detector and the second hazard detector over the 6LoWPAN or another low power wireless protocol.

At step 1515, instructions are transmitted that cause the first hazard detector to share network credentials with the second hazard detector. The instructions may originate from an app and may be routed to the first hazard detector via server 164. Thereafter, the first hazard detector may leverage the wireless communication established between it and the second hazard detector over the second wireless protocol in order to share network credentials. The network credentials may include a network router name and password for connecting to internet 162. This network router may also be the network router that the first hazard detector is using to transmit the instructions of step 1510. The second hazard detector may use the network credentials to connect to the internet 162. Thereafter, the first and second hazard detectors may disable their 6LoWPAN networks and use Wi-Fi to connect to the internet via a network router in order to communicate with the app and/or an online management account located at server 164.

At step 1520, a modified version of method 1300 may be performed in order to establish a new pairing between the second hazard detector and the online management account using the first wireless protocol. The modified version of method 1300 of step 1520 may include all the steps of embodiments and variations of method 1300 with a few exceptions. For example, at the modified step of 1310, step 1520 may automatically use the online management account credentials already stored at the app to associate the second hazard detector with the online management account instead of creating or entering online management account credentials. In addition, step 1520 would clearly not require connecting the second hazard detector to internet 162, because that connection was already accomplished at step 1515 above.

Accordingly, method 1500 may allow for adding additional hazard detectors in a manner that requires less user effort than method 1300. Steps 1510-1525 may be repeated to add a third or additional hazard detectors to a smart-home environment.

As mentioned above, a hazard detector according to the present invention may provide audio and/or visual indicators during the setup process to guide and provide feedback to the user. Similar audio and/or visual feedback may be provided during method 1500. Again, while a limited number of visual and audio indicators generated by hazard detector 104 were described above, other indicators may also be generated by hazard detector 104 during method 1300 and/or 1500. Additional examples may be found in the "Smart Hazard Detector Alerts and Indicators" section below.

In various embodiments, visual effects provided by hazard detector 104 could be varied in a number of different ways. For example, various features may be activated to change faster or slower, brighter or dimmer, for a specific number of animation cycles, with only some of the light participating, and using different colors, e.g., white, blue, green, yellow and red.

These visual effects may be generated by hazard detector 104 for a variety of specified purposes. For example, a specific color, animation, animation speed, etc. or combinations thereof may represent one or more of the following alerts or notifications provided a hazard detector: booting up, selecting language, ready for connections, connected to client, button pressed, button pressed for test, countdown to test, test under way, test completed, pre-alarms, smoke alarms, carbon monoxide alarms, heat alarms, multi-criteria alarms, hushed after alarm, post-alarm, problems, night light state, reset, shutdown begin, shutdown, safely light, battery very low, battery critical, power confirmation, and more. By way of example and not by way of limitation, FIG. 13 illustrates visual vocabulary for visual effects that may be used by hazard detector 104 and FIG. 14 illustrates an animation/color matrix of visual effects that may be used by hazard detector 104.

As mentioned above and specifically described with respect to the physical process representations of FIGS. 7-11, audio effects may accompany the visual effects or may be generated instead of visual effects in order to provide an alert, e.g., the alerts discussed herein.

Audible Low-Battery Warning

Figure 15:
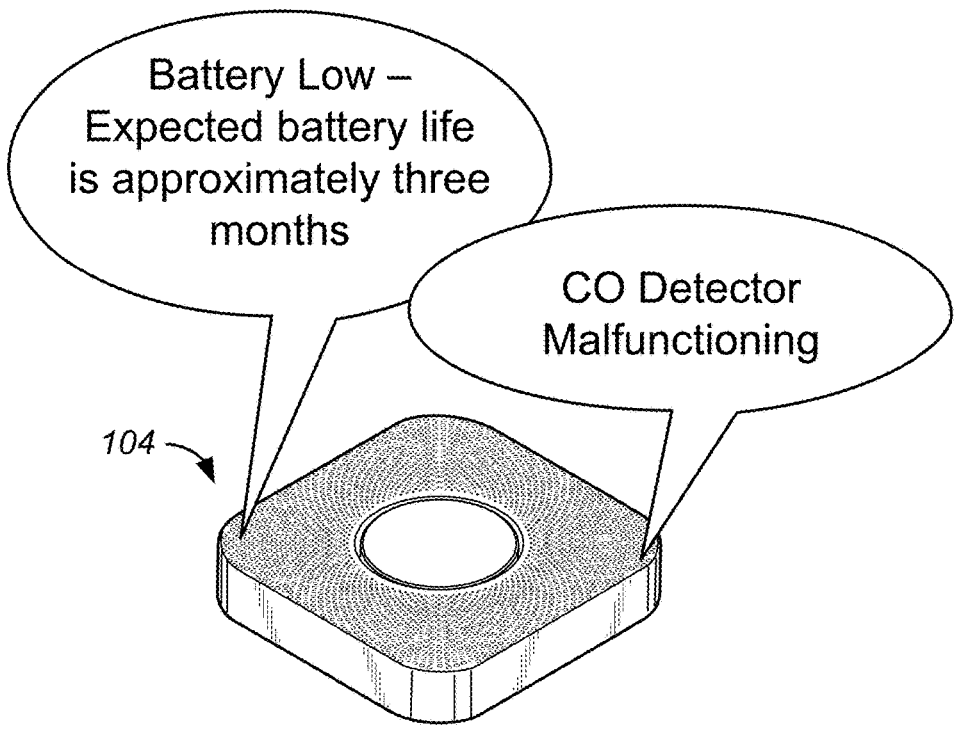
FIG. 15 illustrates an audible low-battery warning, according to an embodiment.

FIG. 15 illustrates an audible low-battery warning, according to embodiments. As illustrated hazard detector 104 outputs an audible massage that says, "Low Battery". The hazard detector 104 can be configured to provide this warning well in advance of the battery actually dying. As illustrated, the audible warning given by the hazard detector 104 indicates that the battery will die in approximately three months. It should be appreciated that hazard detector 104 can be configured to give the low-battery warning before or after three months from when the battery is likely to die. Further, according to embodiments, hazard detector 104 provides periodic reminders until the battery is replaced. For example, hazard detector 104 may provide a weekly or monthly warning. In some embodiments, as illustrated in FIG. 15, hazard detector 104 also provides an audible warning when the CO detector is malfunctioning. It should also be appreciated that it may provide an audible warning when the smoke detector or any other sensor malfunctions. As illustrated in FIG. 10 and described in corresponding sections of the specification, hazard detector 104 is configured to self-test its sensors, such as the smoke detector and the CO detector. In some examples, hazard detector uses its motion sensing capabilities to determine when the home is unoccupied and to conduct the self-testing at those times. As discussed above, if the self-testing reveals that one or more sensors is malfunctioning, hazard detector 104 will audibly notify the occupants.

Alarm Conditions

Serious Hazardous and Pre-Hazardous Conditions

According to some embodiments, alarm condition detection and notification services are provided to detect and warn users of alarm conditions in an environment, such as a home. More particularly, hazard detector 104 detects alarm conditions based on information obtained from its sensors, and it provides corresponding alarms to users. According to embodiments, alarm conditions are divided into two categories: pre-hazardous conditions and serious hazard conditions. Serious hazard conditions are situations where sensor data indicates that conditions in an environment are dangerous to the health and safety of individuals in the environment, and/or alarms are required under applicable National Fire Protection Association ("NFPA") or Underwriters' Laboratories ("UL") standards. Pre-hazardous conditions are situations where the sensor data may not support a serious hazard condition, but is enough to suggest that a pre-hazardous condition may exist in the environment (e.g., the condition may be outside the "normal" conditions recorded at that particular location) such that it is worth notifying users so they can investigate the condition and assess whether remedial measures are warranted to prevent the pre-hazardous condition from escalating to a serious hazard condition.

According to embodiments, the alarm condition detection and notification services are applied to detect elevated levels of potentially dangerous substances (e.g., CO, smoke, heat, etc.) in the smart-home environment 100. In some embodiments, hazard detector 104 determines whether and which alarm condition exists based on whether conditions in the environment have reached one or more thresholds.

According to some embodiments, the thresholds used to determine whether alarm conditions exist represent trends over time in the amount of substances in the environment. These types of thresholds are sometimes referred to herein as "threshold trends". In the following discussion and throughout the present disclosure, it is to be appreciated that any particular numerical levels set forth herein are for illustrative purposes only and are not to be understood as absolute levels in any particular units or measurement systems. Such illustrative units, sometimes provided within quotation marks herein, are to be understood as being hypothetical units for the sake of illustration only. Proper NFPA and UL guidelines and standards should be followed, as would be readily apparent to a person skilled in the art. It is preferable and advisable not to adjust actual emergency alarm thresholds, but rather to adjust thresholds for pre-hazardous conditions (sometimes called "pre-alarm" thresholds herein), as now described.

An example threshold trend is that the amount of a substance (e.g., CO, smoke, etc.) in the environment has increased by at least a 20% over a two-week period. Thus, if the amount of the substance in the environment increases by only 19% over a two-week period, then no alarm condition is determined to exist. Similarly, if the amount of the substance in the environment increases by 21%, but it takes more than two weeks for this increase to occur, then no alarm condition is determined to exist. However, if the amount of the substance in the environment increases by 21% over the two-week period, then an alarm condition is determined to exist. A particular example of a threshold trend is if smoke obscuration in the environment is above "0.5" for thirty seconds, then an alarm condition for smoke is determined to exist. Another particular example of a threshold trend is if the CO-concentration level in the environment has exceeded "50" for two days, then an alarm condition for CO is determined to exist. Yet another particular example of a threshold trend is if heat has exceeded "90" for 5 minutes, then an alarm condition for heat is determined to exist.

According to other embodiments, the thresholds used to determine whether alarm conditions exist represent amounts of one or more substances in the environment, regardless of time. In other words, these thresholds are based on a "snapshot" measurement of substances in the environment. These types of thresholds are sometimes referred to herein as "threshold values". A particular example of a threshold value is when CO reaches "70" instantaneously, then an alarm condition for CO is determined to exist. Another particular example of a threshold is when smoke obscuration reaches "3.0" instantaneously, then an alarm condition for smoke is determined to exist. Yet another particular example of a threshold trend is if temperature reaches "90" instantaneously, then an alarm condition for heat is determined to exist.

According to embodiments, the thresholds used by hazard detector 104 to determine whether alarm conditions exist may be stored in memory on hazard detector 104 itself or remotely by a server, such as the central server and cloud-computer system 164. As described in more detail below, table 2500 of FIG. 17 provides example thresholds used by hazard detector 104 to determine whether alarm conditions exist. According to some embodiments, the example thresholds provided in table 2500 are thresholds for pre-hazardous conditions. In other embodiments, the example thresholds provided in table 2500 are thresholds for serious hazard conditions.

As mentioned, hazard detector 104 may provide an alarm to users upon determining that an alarm condition exists in an environment. In a smoke-related example, hazard detector 104 provides an alarm for smoke, indicating an alarm condition for smoke exists in the environment. In one example, hazard detector 104 determines that an alarm condition exists when, based on data obtained from its sensors, it observes that conditions in the environment have reached or exceeded one or more predetermined thresholds, including one or more of a smoke threshold, a humidity threshold, a CO threshold, and a temperature threshold. In a particular example, hazard detector 104 determines that an alarm condition for smoke exists when the smoke level in the environment exceeds a threshold trend for smoke (e.g., "0.5" obscuration for thirty consecutive seconds). In another smoke-related example, hazard detector 104 determines that an alarm condition for smoke exists when the smoke level in the environment exceeds a threshold trend for smoke and the humidity level of the environment is decreasing. In other examples, hazard detector 104 determines that alarm conditions exist when the CO level of the environment exceeds a threshold value for CO (e.g., CO>"70" instantaneously), or when the temperature of the environment exceeds a threshold trend for temperature (e.g., temperature of environment increases by "+10" in last three minutes).

Traditional smoke detectors are not good at distinguishing steam and smoke. However, by using the above-mentioned thresholds for humidity, CO, and/or heat, hazard detector 104 is better able to distinguish between steam and smoke. For example, in the event hazard detector 104's smoke sensor observes increasing "smoke" levels in an environment, hazard detector 104 won't conclude that an alarm condition involving smoke exists, if hazard detector 104's humidity sensor detects that the humidity in the environment is staying the same or increasing. Instead, hazard detector 104 will conclude that the "smoke" is actually steam because humidity would decrease if fire were the source of the detected "smoke". Similarly, in the event hazard detector 104's smoke sensor observes increasing "smoke" levels, but its CO sensor indicates that CO in the environment is staying the same or decreasing, hazard detector won't conclude that an alarm condition involving smoke exists. Instead, hazard detector 104 will conclude that the "smoke" is actually steam because CO would increase if fire were the source of the detected "smoke".

In a CO-related example, hazard detector 104 provides an alarm indicating an alarm condition for CO exists in the environment. In this example, hazard detector 104 determines that an alarm condition for CO exists when, based on data from its sensors, it observes that conditions in the environment have reached or exceeded one or more predetermined thresholds used to determine whether an alarm condition for CO exists. In one example, hazard detector 104 determines that an alarm condition for CO exists and provides a corresponding alarm when its CO sensor observes CO levels above a threshold trend for CO (e.g., CO concentration exceeds "50" for thirty consecutive seconds, or CO concentration exceeds "300" after a three-minute period, etc.). It should be appreciated that a quadratic function can be used to model the threshold trend for CO. In an example quadratic function, time is the independent variable and CO level is the dependent variable. If, at a particular time, the CO level of the environment exceeds the CO level provided by the quadratic function for that particular time, then hazard detector 104 determines that an alarm condition for CO exists.

In a heat-related example, hazard detector 104 provides a pre-alarm indicating a pre-hazardous condition for heat exists in the environment. In this example, hazard detector 104 determines that a pre-alarm condition for heat exists when, based on data from its sensors, it observes that conditions in the environment have reached or exceeded one or more predetermined thresholds used to determine whether a pre-hazardous condition for heat exists. In one example, hazard detector 104 determines that pre-hazardous condition for heat exists and provides a corresponding pre-alarm when its heat sensor observes heat levels above a threshold value for heat (e.g., temperature exceeds "90"). In another example, hazard detector 104 determines that pre-hazardous condition for heat exists and provides a corresponding pre-alarm when its heat sensor observes temperature levels above a threshold trend for heat (e.g., temperature increased by at least "12" over the last minute). In yet another example, hazard detector 104 determines that a pre-hazardous condition for heat exists and provides a corresponding pre-alarm when its heat sensor observes temperature levels above a threshold value and above a threshold trend for heat (e.g., temperature exceeds "90" and the temperature increased by at least "12" over the last minute). It should be appreciated that a linear function (e.g. piecewise linear function) can be used to model the threshold trend for heat. In an example linear function, time is the independent variable and temperature is the dependent variable. If, at a particular time, the temperature of the environment exceeds the temperature provided by the linear function for that particular time, then hazard detector 104 determines that a pre-hazardous condition for heat exists.

Under some circumstances, users may "hush" hazard detector 104 to cause it to stop "pre-alarming" and to continue monitoring the environment (see FIGS. 23, 24 and the corresponding discussion below). While hazard detector 104 is hushed, users can investigate whether the indicated pre-hazardous condition indeed exists and take any necessary remedial measures. However, if the pre-hazardous condition persists, hazard detector 104 may provide one or more further pre-alarm(s) indicating that the pre-hazardous condition still exists. Further, hazard detector 104 can provide a "regular" or serious hazard alarm indicating a serious hazard condition exists if the pre-hazardous condition escalates to a serious hazard condition. In some embodiments, the thresholds that hazard detector 104 uses when determining whether a serious hazard condition exists are set to or at least based on UL standards. Hushing one alarm may, but typically does not, affect other operations of hazard detector 104 such as further monitoring, annunciation of other alarms, broadcasting alarm status to other devices of the smart-home environment, and/or requests routed through a smart thermostat to alter operation of home systems such as HVAC heaters and fans, to try to stop a source of a hazard or determine a cause of a hazard.

According to embodiments, pre-alarms indicating pre-hazardous conditions provide details about the pre-hazardous condition. For example, hazard detector 104 and/or the central server and cloud-computer system 164 may send a message to the computer 166 of user stating specifics about the condition. In one particular example, the message states, "The CO level in your home has increased twenty-percent in the last two weeks. You might consider having an expert inspect your home to determine the cause." Also for example, hazard detector 104 and/or other smart devices in the home may make similar audible announcements or display similar written messages (e.g. via a user interface or projection onto a wall or ceiling).

Pre-Alarm Settings Automatically Set Based on Location

According to embodiments, thresholds (e.g., smoke thresholds, CO thresholds, heat thresholds) used by hazard detector 104 to determine whether an alarm condition, such as a pre-hazardous condition or a serious hazard condition, exists are adjusted or set based at least in part on where the hazard detector 104 is located. For example, the thresholds used by a hazard detector 104 located in a kitchen to detect alarm conditions in the kitchen may be different than the thresholds used to by a hazard detector 104 located in a bedroom to detect alarm conditions in the bedroom. Thresholds used by the hazard detector 104 located in the kitchen account for smoke levels common to kitchens, thereby making the hazard detector 104 less sensitive to smoke resulting from normal cooking activities that occur in kitchens, thus less likely to false alarm. Reducing false alarms is one notable advantage provided by adjusting or setting thresholds based on where hazard detector 104 is located. Reducing false alarms reduces the likelihood of users disconnecting, unplugging, or otherwise disabling hazard detectors due to the inconvenience and annoyance of false alarms. Accordingly, by adjusting or setting thresholds to reduce false alarms, hazard detector 104 may save the lives of those who would otherwise disable their hazard detectors.

Figure 16:
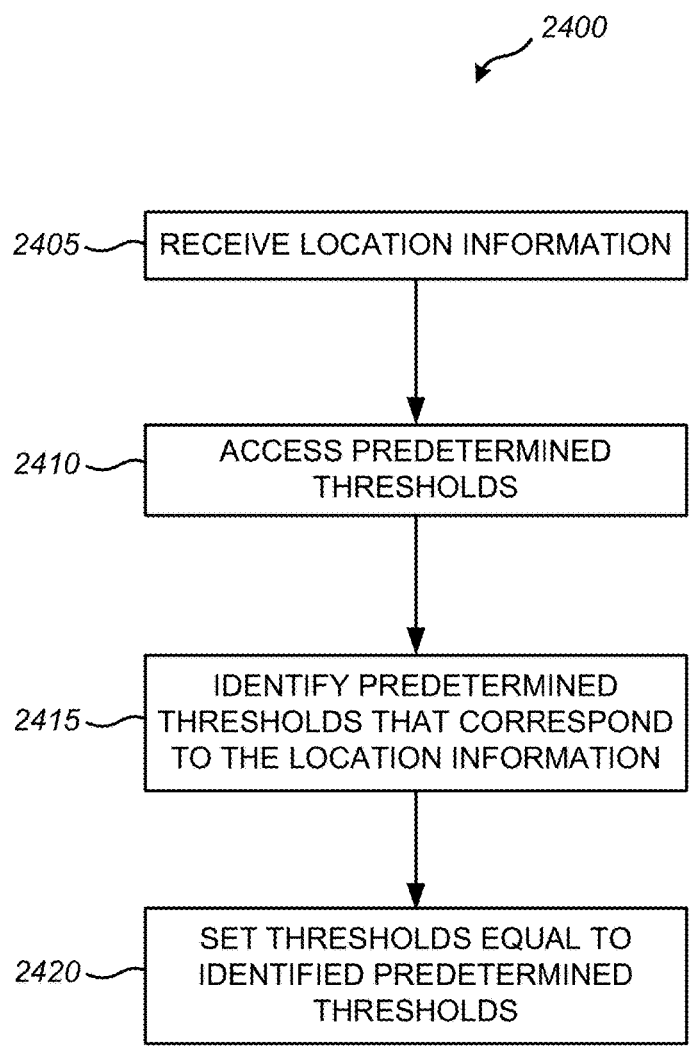
FIG. 16 illustrates a method for setting pre-alarm thresholds for a hazard detector based at least in part on where the hazard detector is located, according to an embodiment.

Turing to FIG. 16, a flow diagram is provided of an exemplary method 2400 of setting one or more thresholds used by a hazard detector (e.g., hazard detector 104) to determine whether a pre-alarm condition exists, according to an embodiment. According to embodiments, the thresholds are set based on the hazard detector 104's location within a home. As indicated at step 2405, the method 2400 generally begins with hazard detector 104 receiving location information. In the illustrated example, hazard detector 104 receives location information from a user. For example, a user provides hazard detector 104 with user input that indicates the location of hazard detector 104 within the home or structure. According to embodiments, the user input indicates the name or type of the room or area (e.g., bedroom, kitchen, etc.) where hazard detector 104 is located.

For example, in step 2405 a user may operate application 1414 (see FIGS. 7-11) running on mobile computing device 1416 and providing a user interface that allows a user to input a location for hazard detector 104. To do so, the user selects a room types (e.g., Living Room, Master Bedroom, etc.), optionally from a list. More particularly, the user may perform a slide gesture on a list object causing the list of room types included on the list object to scroll up or down and place one of the room types in a select field. The user may select a done button to submit the user input, thus indicating the location of the hazard detector within the home. The mobile computing device 1416 would then transmit the user input to hazard detector 104. In some embodiments, the mobile computing device 1416 transmits the user input directly to hazard detector 104 via a personal area network (PAN), short-range wireless communication (e.g., BLUETOOTH, NFC), a local area network (LAN), etc. In other embodiments, the mobile computing device 1416 transmits the input over the Internet to the server 164, which updates the user's online management account to include the location information for the particular hazard detector 104. It should be appreciated that these embodiments of step 2405 are merely examples and that location information may be inputted to hazard detector 104 according to any means know to those have ordinary skill in the art. Further, it should be appreciated the location information could be stored locally by hazard detector 104 and/or remotely on a user's online management account.

As indicated at step 2410, the method 2400 further involves accessing predetermined thresholds that correspond to the location of hazard detector 104. According to embodiments, data is provided that includes predetermined thresholds that hazard detector 104 uses to set its thresholds, which it uses to determine whether pre-alarm conditions for smoke, CO, and heat exist in the location where it is installed. The predetermined thresholds vary based on location. For example, thresholds for determining that a pre-alarm condition for smoke exists in the living room may be less than the thresholds for determining that a pre-alarm condition for smoke exists in the kitchen. Thus, the hazard detector in the kitchen would be less sensitive to smoke and is therefore less likely to activate a false pre-alarm.

Exemplary predetermined, pre-alarm thresholds are provided in data table 2500 of FIG. 17. As illustrated, data table 2500 includes columns 2510, 2515, 2520, and 2525. The "Room Type" column 2510 lists various locations within a home, including living room, bedroom, garage, laundry room, and kitchen. It should be appreciated that these locations are provided for illustrative purposes and that other locations may be provided in addition to or in place of the illustrated locations. The "Pre-alarm Condition for Smoke Thresholds" column 2515 lists predetermined thresholds for determining whether a pre-alarm condition for smoke exists, the "Pre-alarm Condition for CO Thresholds" column 2520 lists predetermined thresholds for determining whether a pre-alarm condition for CO exists, and the "Pre-alarm Condition for Heat Thresholds" column 2525 lists predetermined thresholds for determining whether a pre-alarm condition for heat exists.

As indicated by the data in column 2515 of table 2500, the predetermined threshold for determining whether a pre-alarm condition for smoke exists in a living room is "Obscuration>="0.5" continuously for 30 s". Thus, a hazard detector 104 that receives user input indicating that it is located in a "living room" sets its thresholds for detecting a pre-alarm condition for smoke to "Obscuration>="0.5" continuously for 30 s". Further, according to the example data provided in columns 2520 and 2525, a hazard detector 104 that is located in the living room will set its thresholds for detecting a pre-alarm condition for CO to "CO>="100" instantaneously after 5 min of monitoring", and will set its thresholds for detecting a pre-alarm condition for heat to "Temp>="90" AND TCPM*>="12"".

On the other hand, as also indicated by the data in column 2515 of table 2500, the predetermined thresholds for determining whether a pre-alarm condition for smoke exists in the kitchen are "Obscuration>="2.5" continuously for 1 min AND Humidity<humidity from 3 mins ago". Thus, a hazard detector 104 that receives user input indicating that it is located in a "kitchen" will set its thresholds for detecting a pre-alarm condition for smoke to "Obscuration>="2.5" continuously for 1 min AND Humidity<humidity from 3 mins ago". As such, a hazard detector located in a kitchen will be less sensitive to smoke than a hazard detector located in a living room. In particular, a hazard detector in a living room will determine that a pre-alarm condition for smoke exists when it detects smoke obscuration above "0.5" for thirty seconds, whereas a hazard detector in a kitchen will not determine that a pre-alarm condition for smoke exists until it detects smoke obscuration above "2.5" for one minute and that humidity has decreased in the last three minutes. Accordingly, a hazard detector in a kitchen is less likely to generate a false pre-alarm when a small amount of smoke is emitted from the oven, stovetop, microwave, etc. Further, a hazard detector located in a kitchen is less likely to mistake steam from boiling water as smoke, since its thresholds for determining a pre-alarm condition for smoke require that humidity in the room decrease.

According to embodiments, data having predetermined thresholds and corresponding locations, such as illustrated in FIG. 17, is stored locally on hazard detector 104. For example, the data may be a lookup table stored in memory on the hazard detector 104. Thus, to access predetermined thresholds, according to step 2410, hazard detector 104 accesses the lookup table stored in local memory. In other embodiments, predetermined thresholds may be stored on a remote server, such as the central server or cloud-computing system 164. According to these embodiments, a hazard detector 104 obtains the predetermined pre-alarm threshold by receiving the predetermined pre-alarm threshold from a server via a network communication. For example, hazard detector 104 may transmit a query message that includes the room type inputted by the user, via a network connection, to a server (e.g., server 164). Upon receiving the query message, the server accesses data (e.g., data table 2500) having room types and corresponding predetermined pre-alarm thresholds to identify the predetermined pre-alarm thresholds that correspond to the room type. The server includes the identified predetermined pre-alarm thresholds in a response message and sends that message back to the hazard detector. The hazard detector 104 receives, via the network connection from the server, a response message that includes the predetermined pre-alarm threshold that corresponds to the room type.

Upon accessing data having predetermined thresholds and corresponding locations according to step 2410, method 2400 proceeds to step 2415 for identifying in the accessed data the predetermined thresholds that correspond to the location information. According to an embodiment, with reference to table 2500 of FIG. 17, this step involves identifying the thresholds listed in columns 2515, 2520, and 2525 that correspond with the inputted room type of column 2510. In one particular example with reference to table 2500, if the user input indicates that hazard detector 104 is located in a laundry room, then the corresponding thresholds of column 2515 for determining a pre-alarm condition for smoke are "Obscuration>=1.5 continuously for 1 min OR Temp>+10 in last min", the corresponding thresholds of column 2520 for determining a pre-alarm condition for CO are "CO>=200 instantaneously after 5 min of monitoring", and the corresponding thresholds of column 2525 for determining a pre-alarm condition for heat are "Temp>=110 AND TCPM*>=15". It should be appreciated that the predetermined thresholds of table 2500 are merely examples for illustrative purposes.

Referring again to FIG. 16, method 2400 proceeds to step 2420 for setting the hazard detector's thresholds equal to the identified predetermined thresholds that correspond to the location of hazard detector 104. According to embodiments, hazard detector 104 sets the respective thresholds it uses to detect pre-alarm conditions for smoke, CO, and heat equal to the corresponding predetermined thresholds identified according to step 2415.

Adjusting Pre-Alarms Based on User Preferences, History, and Other Environmental Variations, e.g., for CO Detector Installed in Garage According to embodiments, hazard detector 104 is configured to automatically create a dynamically adjustable pre-alarm based on historical CO data to detect a pre-alarm condition involving CO in a garage, even if hazard detector 104 is not located in the garage. CO detectors are typically not recommended for garages because of the high frequency of false alarms due to the high levels of CO produced by cars. However, it would be beneficial to provide CO detection for garages. For example, the smart-home environment can learn what CO levels are typical for a garage and thus infer when atypical CO events occur. For example, in the event a user slips and falls after starting their car, an alarm to another user that indicates an alarm condition involving CO is occurring in the garage may save that user's life.

To provide said CO-detection for garages, hazard detector 104 records a historical log of CO data that it has detected. This log may be stored locally on hazard detector itself, or it may be stored at server 164, and the data therein may be analyzed to provide a variety of inferences about how CO levels vary in a particular garage. For example, a processor of hazard detector 104 or of server 164 can apply algorithms to the logged CO data to determine whether the data indicates that one or more automobiles are regularly started nearby. The algorithms may detect occasional CO spikes that quickly dissipate and, based on the amount by which the CO level increases and the amount of time it takes for the detected CO to dissipate, hazard detector 104 or server 164 may infer that the spike was caused by a car that was started and then driven away. Appropriate, multiple thresholds may be developed for hazard detectors 104 that are in or near intermittent CO sources, such as kitchens (with CO released from gas stoves, and/or from cooking), basements (combustion based heat sources), garages (motor vehicles, lawn mowers and other combustion based motors); methods for developing and implementing such multiple thresholds are discussed below in connection with FIGS. 20D and 20E.

If, after making an inference that a car is regularly started and driven away, hazard detector 104 observes an incident where the CO spikes but does not dissipate in a manner that is consistent with previous CO spikes, then hazard detector 104 may determine that a pre-hazard condition for CO exists. Because it takes advantage of historical data, this determination can be reached with confidence even if the increased CO levels are not high enough to present a serious hazard, or even a pre-hazardous condition under usual circumstances. For example, CO thresholds for pre-hazardous and serious hazard conditions may require a high CO concentration level for a one-hour period before alarming, or a moderately high CO level for one month before alarming.

Adjusting Pre-Alarm Thresholds and Volume if Someone is Sleeping

Tragically, people sometimes die in house fires because they are sleeping and do not hear an alarm in time to evacuate to take remedial measures to put out the fire. Accordingly, hazard detector 104 is capable of adjusting the thresholds it uses for determining whether a pre-alarm condition exists so that it "pre-alarms" sooner and more frequently. Further, hazard detector 104 is capable of increasing the volume of its alarm when it determines that an individual is sleeping in the home.

According to embodiments, to determine when an occupant is sleeping in a particular room, hazard detector 104 leverages sensors of smart devices located in the mesh network of the smart-home environment in combination with rules-based inference engines or artificial intelligence provided at the central server or cloud-computing system 164. According to embodiments, the smart device in the smart-home environment 100 that happens to be closest to an occupant when that occupant falls asleep may transmit a message indicating that the occupant has stopped moving and appears to be sleeping. The message will be transmitted through the mesh network to the hazard detectors 104, which will then automatically increase their alarm volumes and reduce the thresholds used to determine whether pre-hazardous conditions exist in the home. Thus, in the event of a potentially dangerous condition, the hazard detectors 104 may provide an alarm sooner and louder than usual, thereby making it more likely that the occupant will already be awake by the time the conditions worsen enough to warrant an alarm indicating a serious hazard condition (e.g., an alarm based on UL standards).

Simple Alarm Flow; Announcement that "Hazard is Clearing"

Figure 18A:
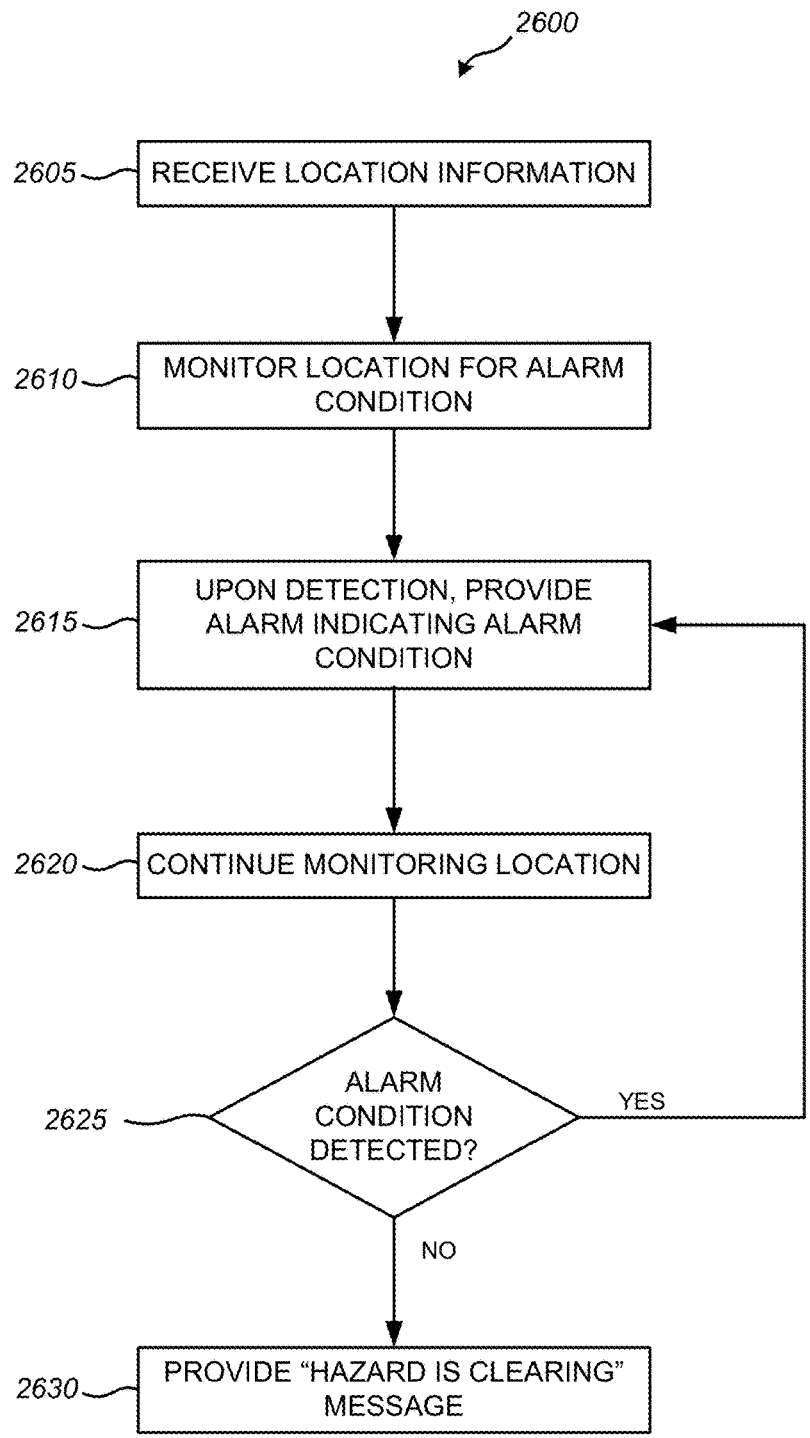
FIG. 18A illustrates a method for providing a "normalcy" message when an alarm condition has cleared from a location, according to embodiments.

FIG. 18A illustrates a method 2600 for providing an alarm message when an alarm condition is detected in a location and providing a "hazard is clearing" message as the alarm condition clears from the location, according to embodiments. Oftentimes, after receiving an alarm indicating that an alarm condition has been detected in their home, users evacuate the home and/or take remedial measures to clear the alarm condition. For example, upon hearing a smoke alarm, users may search the home to find the source of the smoke and take remedial measures to stop the smoke, such as by turning off a smoking oven or stove. However, known hazard detectors do not notify users when the condition has been addressed such that the hazard is at least beginning to clear. This is particularly true for CO alarms. In response to a CO alarm, users may open windows to clear CO from the home, but, because humans cannot sense CO, they cannot determine if the CO condition is clearing. Accordingly, hazard detector 104, such as by implementing method 2600, continues monitoring after it provides an alarm and, if it detects that the condition is clearing, it communicates to users a "hazard is clearing" message that informs users that the condition is clearing.

The method 2600 generally begins at step 2605 where hazard detector 104 receives location information. This step is similar to step 2405 of method 2400 and step 1320 of method 1300. As described herein with reference to those methods, in step 2605 a user provides hazard detector 104 with user input that indicates the location of hazard detector 104 within the home or structure. According to embodiments, the user input indicates the name or type of the room or area where hazard detector 104 is located. The room names or types inputted by users include, for example, Master Bedroom, Kids Bedroom, Guest Bedroom, Kitchen, Laundry Room, Garage, Living Room, Den, Office, etc. In step 2610, method 2600 monitors the location for an alarm condition, such as the alarm conditions for smoke, CO, and heat described above.

As indicated at step 2615, upon detecting an alarm condition, hazard detector 104 provides an alarm message notifying users of the detected condition. It should be appreciated that the alarm message may be communicated to users via multiple channels, such as broadcast by speaker, changes to emitted light color, intensity and/or dynamics, and/or distribution by electronic message (e.g., SMS, e-mail, alert in a smartphone or tablet app). Further, according to embodiments, the alarm message includes a description of the detected condition and a location where the condition was detected. For example, hazard detector 104 uses its speaker 950 to output a voice announcement that includes a description of the condition and a location where the condition has been detected. In other examples, hazard detector 104 causes a corresponding electronic message (e.g., e-mail, SMS) to be sent to computers 166 of users associated with the home. According to embodiments, hazard detector 104 determines the location based on the room name or type provided by the user, as previously described with reference to step 2605. The hazard detector includes this room name or room type in alarm messages to indicate where a condition has been detected. Further, according to examples, hazard detector 104 is at least capable of detecting the alarm conditions described above with reference to FIGS. 16 and 17, including for example alarm conditions for smoke, CO, and heat.

In a particular example, upon detecting an alarm condition for smoke in a kitchen, hazard detector 104 provides the alarm "Smoke detected in kitchen". Hazard detector 104 can announce the "Smoke detected in kitchen" alarm via its speaker 950 and/or it can send the "Smoke detected in kitchen" via electronic messages to computers 166. Other example, announcements include, "Smoke detected in living room", "Smoke detected in Master Bedroom", "Smoke detected in kid's bedroom", "Smoke detected in guest bedroom", etc.

After detecting the alarm condition and communicating to users a corresponding alarm message, hazard detector 104 continues to monitor the location where it is installed, as indicated at step 2620. At step 2625, if the alarm condition continues to be detected or if a new alarm condition is detected, hazard detector 104 may provide an alarm message indicating the continuing and/or newly detected condition, as indicated at step 2625. In particular, if the previously detected condition persists, hazard detector 104 continues to provide the same alarm message. However, according to embodiments, if the condition has escalated or improved, hazard detector 104 alters the alarm message to reflect the changed condition.

If the condition has escalated from a pre-hazardous condition to a serious hazard condition, hazard detector 104 indicates this escalation in its alarm message. For example, rather than announcing "Smoke detected in living room", hazard detector alarms according to UL standards for smoke, and includes an announcement that the condition is serious. For example, this serious hazardous alarm may be "BEEP, BEEP, BEEP—Smoke detected in living room—BEEP BEEP BEEP!" On the other hand, if the condition has improved and gone from a serious hazard condition to a pre-hazardous condition, hazard detector 104 indicates this improvement in its alarm message. For example, rather than announcing alarming according to UL standards and including "BEEPS" in the message, the hazard detector 104 may simply announce "Smoke detected in living room". According to embodiments, hazard detector 104 may explicitly indicate that the condition has improved or worsened. For example, the alarm message could say, "Condition has escalated to a serious hazard condition" or "Condition has improved, but a pre-hazardous condition still exists".

Still referring to step 2625, if the detected alarm condition has cleared such that no alarm condition is detected, hazard detector 104 may communicates to users a "hazard is clearing" message, as indicated at step 2630. In embodiments, the "hazard is clearing" message does not specify or guarantee that normalcy with respect to the detected condition has been restored. For example, if the detector condition were smoke, then the "hazard is clearing" message is limited to smoke in the kitchen and it may be audible communicated to users as, "The previously detected smoke in the kitchen is clearing." Referring to the example alarm condition for smoke in a kitchen mentioned above, if upon continued monitoring of the kitchen, hazard detector 104 determines that the alarm condition is clearing, then hazard detector 104 may communicate a corresponding message. For example, hazard detector 104 may provide the message, "Smoke in the kitchen is clearing". Hazard detector 104 can announce the "Smoke in the kitchen is clearing" message via its speaker 950 and/or via electronic messages to computers 166. Continuing with this example, if other hazard detectors 104 in the home had also detected and alarmed for alarm conditions, those hazard detectors 104 can provide their own "hazard is clearing" messages when alarm conditions in the locations have cleared. For example, upon alarm conditions clearing in its location, hazard detector 104 located in the living room can announce, "Hazard is clearing in the living room". Similarly, hazard detector 104 in the master bedroom announces, "Hazard is clearing in the master bedroom", and so forth. This way, as the hazard clears in the various rooms of the house, the user will receive messages, such as audible voice announcements from the hazard detectors themselves, and/or electronic messages sent to users' computers 166. These "hazard is clearing" alarms are particularly useful for alarm conditions involving CO, because humans cannot sense CO.

Alarm Implementation: Status Identifiers, Alarm Broadcasts, and Audible Alarms

Figure 18B:
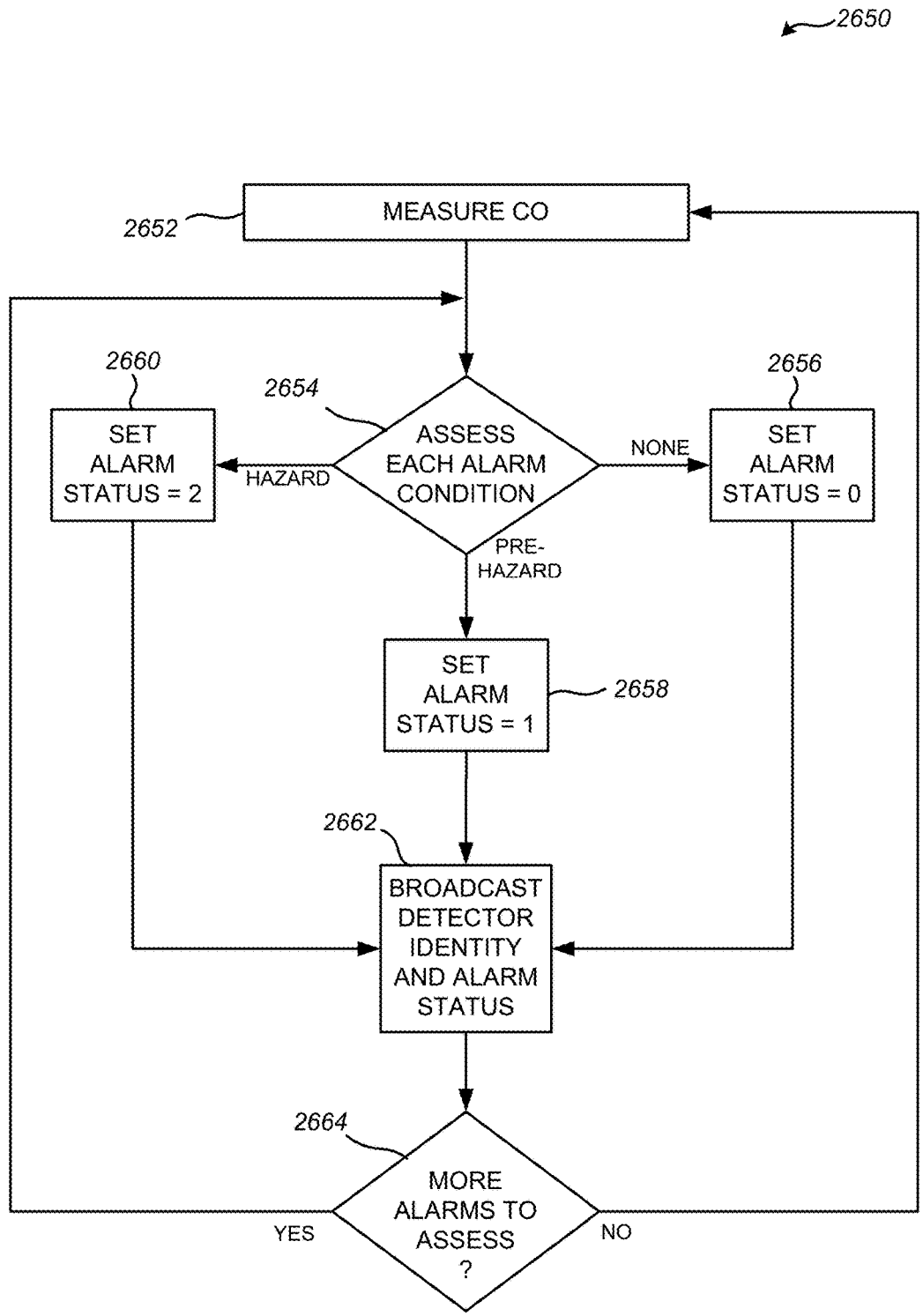
FIG. 18B illustrates a method of establishing alarm codes within smart devices of a smart-home environment, according to embodiments.

FIG. 18B illustrates a method 2650 for assigning and broadcasting alarm status identifiers in a smart device, according to embodiments. Method 2650 includes exemplary action and decision steps that utilize status identifiers to define alarm states; it should be apparent upon reading and understanding the disclosure herein that alarm states are not the only type of states that may be defined by status identifiers. Moreover, although method 2650 is presented in terms of alarms related to CO, it should be apparent that method 2650 may be adapted for use with detection of other smart-home environment characteristics such as hazardous substances, extreme temperatures, and/or other conditions or detectable substances that indicate a hazardous condition, such as smoke.

Method 2650 begins with a step 2652 of measuring CO in a location of a particular hazard detector 104. Step 2654 assesses each applicable alarm condition for the particular hazard detector 104; there may be one or more such limits that depend on the most recent CO measurement, CO history at the location of the hazard detector, current measurements of other smart-home environment characteristics and other factors. Each alarm condition typically has three possible alarm states: No hazard, a pre-hazardous condition, or a hazardous condition. The default condition is no hazard; possible criteria and thresholds for determining if a pre-hazardous or hazardous condition are disclosed elsewhere herein. If step 2654 determines that a CO measurement of an alarm condition does not meet either of an applicable pre-hazardous or hazardous threshold, an alarm status identifier for that alarm condition is set to zero in step 2656. If step 2654 determines that the CO measurement meets or exceeds an applicable pre-hazardous threshold but does not meet a hazardous threshold, the alarm status identifier for that alarm condition is set to one in step 2658. If step 2654 determines that the CO measurement meets or exceeds a hazardous threshold, the alarm status identifier for that alarm condition is set to two in step 2660. After the applicable step 2656, 2658 or 2660, step 2662 broadcasts the identity of the hazard detector 104 and the determined alarm status identifier to other smart devices. This allows other smart devices to repeat audible warnings about pre-hazardous or hazardous conditions in any location of the smart-home environment. A subsequent step 2664 checks to see if any further alarm conditions need to be assessed; if so, method 2650 returns to step 2654, otherwise method 2650 returns to step 2652, repeating indefinitely.

Turning on HVAC Fan to Clear Smoke and/or CO

Figure 19:
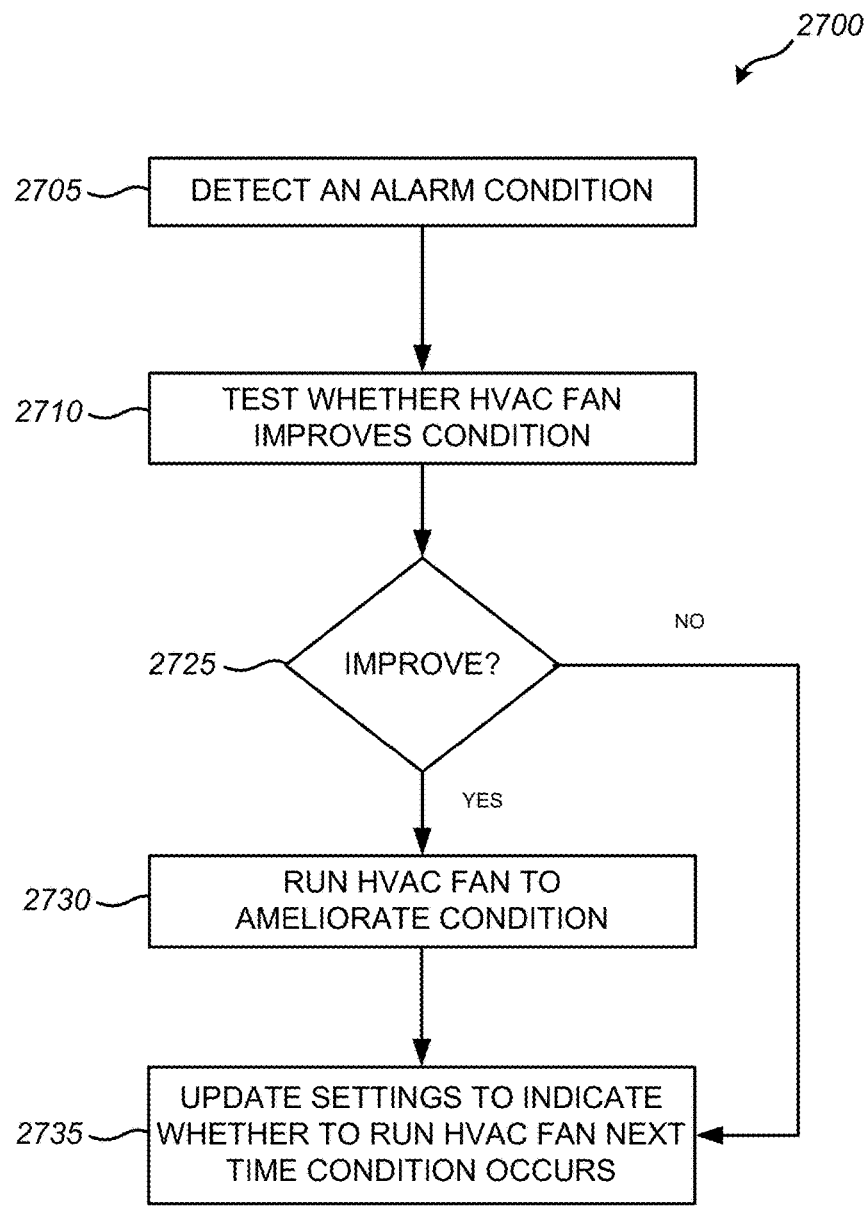
FIG. 19 illustrates a method of controlling an HVAC fan to at least partially ameliorate hazardous conditions, according to an embodiment.

According to an embodiment, in the event of an alarm condition involving smoke, CO, or heat in the home, an HVAC fan can be turned on to help remedy the alarm condition by at least partially removing the smoke, CO, or heat from the home, or at least moving air to the most severely affected home areas. FIG. 19 provides a method 2700 that can be implemented in a home having a smart thermostat 102 that communicates with a hazard detector 104 to control the HVAC fan to help remedy alarm conditions detected by the hazard detector, according to embodiments.

Method 2700 generally begins at step 2705, where an alarm condition in the home is detected. For example, one or more hazard detectors 104 in a home detect an alarm condition, such as a pre-hazardous or serious hazard condition involving smoke, CO, or heat. As indicated at step 2710, upon detecting an alarm condition, the smart thermostat and the hazard detector 104 coordinate to test whether the HVAC fan helps remedy the detected condition. For example, the smart thermostat 102 turns on the HVAC fan and the hazard detector 104 monitors the home environment to determine if the detected alarm condition begins to improve, at least in the area of the specific hazard detector 104. For example, if the alarm condition is a pre-hazardous condition for smoke or CO in the living room, the hazard detector 104 determines whether the smoke level decreases in the living room. Further, to make sure the HVAC is not just redistributing smoke throughout the home, the hazard detector 104 may communicate with other hazard detectors 104 in the home to make sure the smoke or CO level in other rooms is not increasing. It determines that the HVAC fan helps remedy the alarm condition, if the smoke level decreases throughout the house. However, if the smoke or CO is just redistributed to other rooms, then it determines that the HVAC does not improve the condition. Interconnected hazard detectors throughout the home make this possible. Similarly, for example, if the alarm condition is a pre-hazardous condition for CO in the living room, the hazard detector 104 determines whether turning on the HVAC fan causes the CO level to decrease in the living room. Distributing CO throughout the house could be potentially harmful, but could also help bring down a CO level in a severely affected room from a lethal level. Accordingly, the hazard detectors monitor the CO levels in other rooms to ensure that turning on the HVAC fan to reduce CO in the living room either does not increase CO levels in other rooms, or that any such increases are modest compared to reducing an extremely high CO level in one or more rooms.

As indicated at decision step 2725, if turning on the HVAC fan indeed helps remedy the alarm condition by at least partially removing smoke, CO, or heat from the home, then as indicated at step 2730 the thermostat 102 continues to run the HVAC fan. For example, the thermostat 102 runs the HVAC fan until the hazard detectors determine that the condition is ameliorated or until the condition is no longer continuing to improve (e.g., the smoke level is no longer decreasing). Further, as indicated at step 2735, the thermostat 102 updates the account settings, such as in the online management account discussed with reference to FIGS. 13 and 15, that turning on the fan when the alarm condition is detected helps remedy the alarm condition. Thus, according to an embodiment, the next time the alarm condition is detected, the HVAC fan is automatically turned on, without testing to determine whether the HVAC fan helps improve the condition.

Referring again to decision step 2725, if turning on the HVAC fan does not help remedy the alarm condition, then as indicated at step 2735, the thermostat 102 updates the account settings to indicate that turning on the fan does not help ameliorate the alarm condition. Thus, the next time the alarm condition is detected, the HVAC fan is not turned on.

Determining Cause of CO Condition

Oftentimes, in the event an alarm condition involving CO is occurring in a home, the source of the CO is a thermostat-controlled, combustion based heat source, such as a gas or heating oil burning HVAC system that, due to an improperly vented furnace or boiler, emits CO into the home as a byproduct of creating heat. However, thermostat-controlled heating sources are not always the source of the CO. For example, high CO levels in homes may also be caused by non-thermostat-controlled heating sources, such as fireplaces, wood stoves, kerosene heaters, etc. Further, high CO levels may be caused by non-heating HVAC sources, such as gas water heaters, gas stoves and ovens, generators and other fossil-fuel-powered (e.g., gasoline, kerosene, propane, natural gas, etc.) equipment.

Figure 20A:
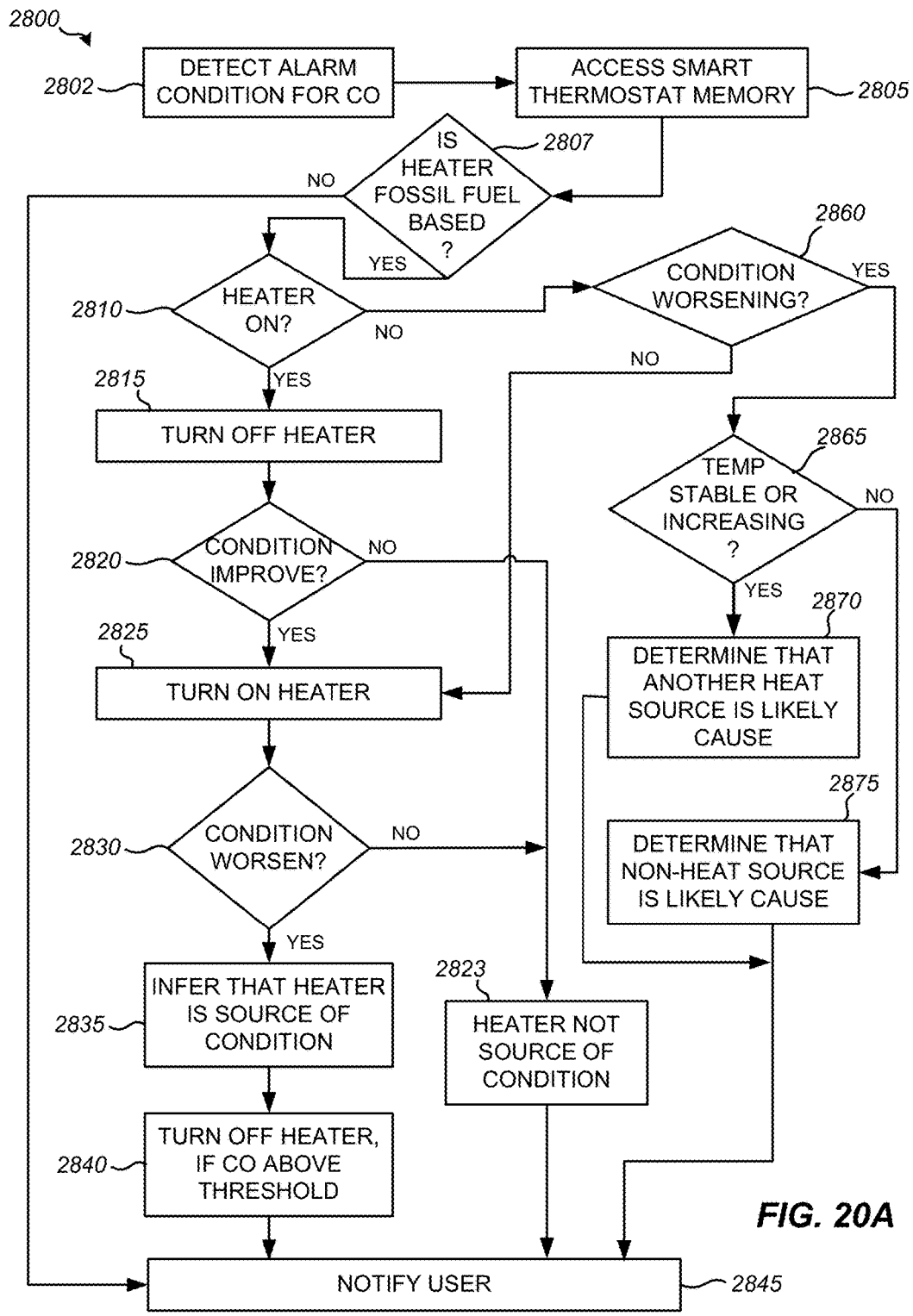
FIG. 20A illustrates a method of determining a cause of a high CO condition in a smart-home environment and, when appropriate, altering at least one aspect of the home environment to at least partially ameliorate the high CO condition, according to an embodiment.

FIG. 20A is a flowchart of a method 2800 for determining a source of CO in a home environment in which an alarm CO condition has been detected and, when appropriate, altering at least one aspect of the home environment to at least partially ameliorate the alarm CO condition, according to embodiments. Method 2800 may be performed, for example, by smart hazard detector 104 in cooperation with smart thermostat 102, which include CO measurement hardware and the ability to control a heater (e.g., HVAC system 103) respectively. However, it should be understood that determinations and inferences based on the CO measurements may be performed by other devices as well; for example, CO measurements may be transmitted to central and/or offsite computer systems, such as cloud-computing system 164 (FIG. 1) for analysis by such systems. A system that performs data analysis related to CO measurements may be referred to herein as the "analyzing system" with the understanding that such system may be any of the hazard detector 104, smart thermostat 102, cloud-computing system 164 or other computing system that can access the required data.

As indicated at step 2802, method 2800 generally begins with detecting an alarm condition for CO in the home. In the context of method 2800, "alarm condition" can mean either of a serious hazard "alarm" condition, or a "pre-alarm" condition, that is, method 2800 may be performed to determine a source of CO whether the condition detected is strictly defined as a "hazard" or it is merely out of the ordinary. Upon detecting the alarm condition, method 2800 accesses a memory of smart thermostat 102, as indicated at step 2805. In a first decision step 2807, information from the memory of smart thermostat 102 is used to determine whether a heater of an HVAC system being controlled by smart thermostat 102 uses a fossil fuel-based heat source. If step 2807 determines that the heater is not fossil-fuel based (e.g., it is instead an electric heater, heat pump or hydrogen burning heater) method 2800 skips directly to step 2845, described below. If step 2807 determines that the heater is fossil fuel-based, method 2800 proceeds instead to step 2810.

At decision step 2810, smart thermostat 102 determines whether the thermostat-controlled heater is running. As indicated at step 2815, if the thermostat-controlled heater is running, then the smart thermostat 102 turns off the heater. At indicated at step 2820, after the heater is turned off, hazard detector 104 monitors the home environment to assess whether the CO condition is improving (e.g. CO level decreasing). As indicated at step 2825, if the CO condition improved, the smart thermostat 102 does a "pattern matching" test by turning the heater back on and, as indicated at step 2830, the hazard detector assesses whether the CO condition is worsening now that the heater has been turned back on. As indicated at step 2835, if the condition worsened when the heater was turned on again, then an inference is made that the thermostat-controlled heater is the source of the CO condition in the home environment. As indicated at step 2840, if the CO condition is above a threshold level, the smart thermostat 102 turns off the heater. For example, smart thermostat 102 may turn off the heater if the CO condition is determined to be a serious hazard condition. As indicated at an optional step 2845, a user may be notified that the thermostat-controlled heater is likely the source of the CO condition. Step 2845 may or may not be performed in every instance of method 2800; for example, if the alarm condition detected in step 2805 is a CO excursion from a statistical baseline in which a CO level is elevated but is still far from dangerous levels.

Referring again to step 2810, if—after detecting the CO condition—it is determined that the thermostat-controlled heater is not on, the hazard detector 104 monitors the home environment to determine whether the CO condition is worsening. For example, the hazard detector 'watches' the CO level to 'see' if it is staying the same, getting better, or getting worse. As indicated at step 2860, if the condition is not worsening (i.e., staying the same or getting better), then the smart thermostat engages in the "pattern matching" described above with reference to steps 2825 to 2835, where it "looks" for a pattern where CO concentration increases when heater is on and decreases when heater is off. If it "sees" that pattern, then it infers that the heater is the source of the CO. However, as indicated step 2865, if the condition is worsening, even though the thermostat-controlled heater is off, the smart thermostat 102 monitors temperature of the home environment to determine if the temperature is stable or increasing. As indicated at step 2870, if the temperature is stable or increasing, even though the thermostat-controlled heater is off, then it may be inferred that another heat source (e.g., fireplace, wood stove) is heating the home and that that heat source is the cause of the CO condition. The user may then be notified that a non-thermostat-controlled heater, such as a fireplace, is the likely source of the CO, as indicated at optional step 2845. However, as indicated at step 2875, if the temperature is not stable or increasing (i.e., the temperature is decreasing), then it is inferred that a non-heat source (e.g., hot water heater, gas oven or stove, etc.) is the cause of the CO condition and the user may be notified accordingly, as indicated at optional step 2845.

According to embodiments, hazard detector 104, other smart devices of smart-home environment 100, cloud-computing system 164 or other systems that receive data from smart-home environment 100, can determine pre-hazardous alarm thresholds to avoid nuisance alarms and/or make inferences about routine CO excursions, including the source(s) of such excursions. In embodiments, these determinations and/or inferences may occur even in the event the home environment does not include a network-connected smart thermostat 102 that controls the home's climate control system. For example, hazard detector 104, other smart devices or cloud based systems can 'look' for patterns involving temperature in the home and CO level in the home, and can set appropriate CO pre-alarm threshold(s) accordingly. If CO increases when temperature increases and if CO decreases when temperature decreases, then a hazard detector 104 may infer that a heater of some kind inside the home is the source of the CO and notify a user regarding the same. Alternatively, if CO routinely increases at one or more times of day without a concurrent temperature increase, the analyzing system may not be able to determine a source, but may be able to establish higher pre-hazardous condition limits for those times of day. Or, if CO increases can be correlated with other household events (e.g., noise in the kitchen, indicating that cooking is taking place, or a sequence of garage door openings and/or closings) the analyzing system may be able to establish higher pre-hazardous condition limits that can be applied in association with such events (see FIG. 20E).

Similarly, in embodiments, a smart thermostat can, alone or coordinated with a smart hazard detector, operate any controllable aspect of an associated climate control or HVAC system in isolation, to determine a source of a hazard or to ameliorate a hazard that exists. For example, it may be known (e.g., at installation time of the smart thermostat) or can be determined (see FIG. 20A) that a climate control system includes a combustion based heat source. With this knowledge, the smart thermostat may be able to send independent signals to different components of the climate control system such as a system fan and the heat source. For example, it may be very useful to turn off the heat source (to shut down a CO source) while leaving a system fan running (to help clear CO from the home, or at least reduce the CO from lethal levels in one particular area). It may also be possible, or it may be the only available option, to send a single signal that causes the climate control system to sequentially turn off the heat source first, and later shut off a system fan.

Figure 20B:
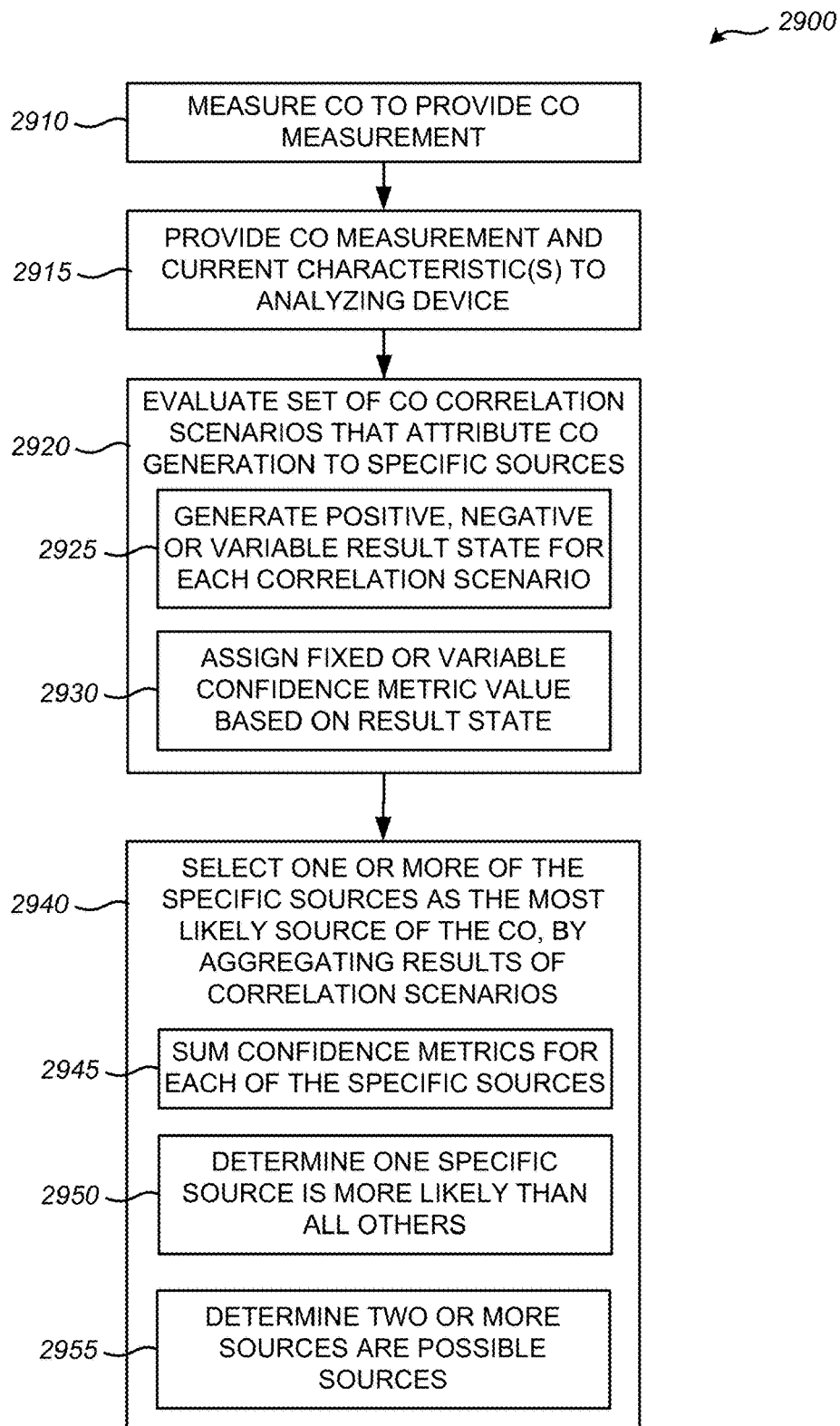
FIG. 20B is a flowchart illustrating a method 2900 for determining one or more sources of CO in a smart-home environment, according to an embodiment.

FIG. 20B is a flowchart illustrating a method 2900 for determining one or more sources of CO in a smart-home environment. In a first step 2910, a smart device of the smart-home environment measures a level of CO to generate a CO measurement. It should be understood that a CO "measurement" as referred to here may be a single point, or a trend of such measurements (e.g., wherein at least the two or more most recent measurements increase in succession over a defined set of previous measurements). An example of step 2910 is one of hazard detectors 104 generating a CO measurement. Other smart devices of the smart-home environment generate current characteristics of the smart-home environment; these characteristics may be measurements (e.g., temperature, smoke, other CO measurements, sounds, light, detected motion and the like), settings (e.g., temperature settings, control states of HVAC equipment and the like) or inferences (such as whether users or occupants of the smart-home environment are "home," "away," "sleeping" and the like, as described elsewhere herein). In step 2915, the CO measurement and the current characteristics are provided to an analyzing device. The analyzing device may itself be the hazard detector 104 that measured the CO, another smart device of the smart-home system, a computer associated with the smart-home environment (e.g. a computer 166 in the form of a computer, a smartphone, a tablet or the like) or it may be a cloud based computer system, such as cloud-computing system 164, FIG. 1.

In step 2920, the analyzing device evaluates a set of correlation scenarios, each of which attempts to attribute CO to a specific source. Each correlation scenario, when evaluated, yields a result state that may yield a positive or negative result state in an optional substep 2925, (e.g., "yes" the CO is coming from the specific source or "no" it is not); or a variable result in an optional substep 2930 that indicates a conclusion that the specific source "might be" where the CO is coming from, with a degree of confidence associated with the result. In embodiments, the result of evaluating each correlation scenario generates a confidence metric that the CO is from the specific source. When the evaluation generates a positive or negative result state, a fixed value may be assigned to the result state, while if the evaluation generates a variable result, a variable value may be assigned as the confidence metric. This allows inferences to be built up by aggregating a series of results that would be of low overall confidence value individually, but add to form a high confidence value when all of the results point to the same conclusion. It is noted for completeness that confidence metrics may be arbitrarily assigned as estimated percentage confidence of a particular result, but that the percentages so assigned may not add up to 100%.

In step 2940, the analyzing device selects one or more of the specific sources as the most likely CO source, by aggregating results of the correlation scenarios. For example, in a first optional substep 2945, the analyzing device may sum confidence metrics for each of the specific sources that were evaluated in correlation scenarios. Step 2940 may also, in an optional substep 2950, determine that one of the specific sources is more likely than all of the others. For example, a confidence window may be established, and the results of step 2940 may be based on whether one, two or more of the specific sources have confidence metrics within the confidence window of one another. To illustrate, if several scenarios are evaluated and one specific source has a confidence metric sum of 56% while no other source has a confidence metric sum greater than 10%, method 2900 may "conclude" that the specific source with the 56% confidence metric sum is the CO source, and may make announcements and/or action decisions (such as operating HVAC controls, etc. as discussed in connection with FIG. 20A and elsewhere) based on this "conclusion." Alternatively, in another optional substep 2955, step 2940 may determine two or more specific sources have confidence metric sums within a predetermined tolerance of the highest such sum, and may determine that those sources that are both possible sources of the CO. To illustrate, if the confidence window is established as 10%, and three specific causes evaluated in step 2920 generate confidence metric sums of 40%, 35% and 18%, method 2900 may conclude that the first two confidence metric sums indicate two specific sources, either of which could be the CO source, while the third specific source could not.

FIG. 20C shows a table 2980 illustrating possible correlation scenarios for identifying CO sources. Each row of table 2980 shows a correlation scenario including a CO measurement whose source may be identified, other smart-home characteristic(s) that may help identify the source, a source identified as correlating with the CO measurement and the smart-home characteristic(s), and a possible confidence metric that could be assigned to the identification. Table 2980 is exemplary only, and merely provides some examples of correlation scenarios that could be developed. Many other causes could be correlated to CO measurements and smart-home characteristics; the confidence metrics are also exemplary and would be adjusted for a given smart-home environment based on information acquired from that particular environment. A table similar to table 2980 could be set up, maintained by and made available to one or more analyzing devices in a smart-home environment such that the scenarios therein could be evaluated. The evaluation of correlation scenarios could be continuous or set up to occur on demand based on location associated with a CO measurement, or based on a CO measurement exceeding a typically low threshold that indicates a small excursion above a typical level.

Inferences about CO sources can also be made based on user status information, that may be provided by the user, or inferred. For example, any sharp increase in CO when the smart-home environment is in an "away" or "vacation" state may be treated as indicating at least a serious malfunction in a heating system or other combustion based system, or possibly a fire. Responses to such sharp increases when occupants are believed to be "away" may trigger earlier and sharper warnings both within the smart-home environment in case, unknown to the smart-home environment someone is at home, and is unaware of the CO source. Alerts may also be made earlier to systems that are or may be physically outside the smart-home environment. For example, alerts may be sent to computers 166 that are mobile devices, or to cloud-computing system 164, which may interface with alarm companies, law enforcement and/or firefighting organizations. Similarly, when an occupant is believed to be at home but sleeping, alerts may be generated at lower CO levels and/or directed to an area in which the occupant is believed to be.

Successive observations can be utilized to refine and increase confidence in correlation scenarios, and thus to increase the confidence metric assignable to such scenarios. Such successive observations may validate some or all the circumstances of each correlation; for example, a phenomenon that initially appears to occur every day may not continue to do so, yet may be discernible as occurring on weekdays but not weekends, or on some other recognizable subset of days. Such subsets may be recognizable as, for example, every other day, every third day, once or twice a week, weekend days, the first and third Mondays of each month, every weekday except during summer, and the like. Correlation scenarios can be refined over time to best match the sensed characteristics of each smart-home environment, and the confidence metrics assigned in connection with evaluating the correlation scenarios can be increased (or decreased) according to the degree to which such characteristics always match, or do not match, specific instances. Any of the devices of the smart-home network itself, and/or external resources such as computer 166 or cloud-computing system 164, may examine past data to find and refine correlations. Possible results of such examination include adjustments to the confidence metrics associated with one or more correlation scenarios, new entries to table 2980, and/or splitting existing correlation scenarios into two or more correlation scenarios that better track different combinations of CO measurements and smart-home characteristics.

Some smart thermostats provide extreme temperature safeguards in order to keep pipes from freezing at very low outside temperatures, or prevent pet deaths at very high outside temperatures. Such thermostats may have, for example, low (or high) temperature safety thresholds that if crossed, cause the thermostat to attempt to activate heating at low temperature, or cooling at high temperature. Embodiments herein may honor the extreme temperature safeguards even when doing so overrules CO related detection and climate control system operational conditions described herein. For example, a smart thermostat may first operate under a rule that turns off an HVAC heat source because of dangerous CO levels, and may continue to detect high CO levels, but may then detect a low temperature below its low temperature safety threshold. In such cases, it may reactivate the heat source, under the assumption that no persons are being affected by the CO levels (e.g., there is nobody home) but if not heated to at least the low temperature safety threshold, pipes would freeze and burst. In such cases, and in all cases where high levels of CO are detected while no persons appear to be present in the home, the smart thermostat and/or other smart devices of the smart-home environment may provide audible and/or flashing light warning messages as soon as motion is detected at any of the smart devices.

Figure 20D:
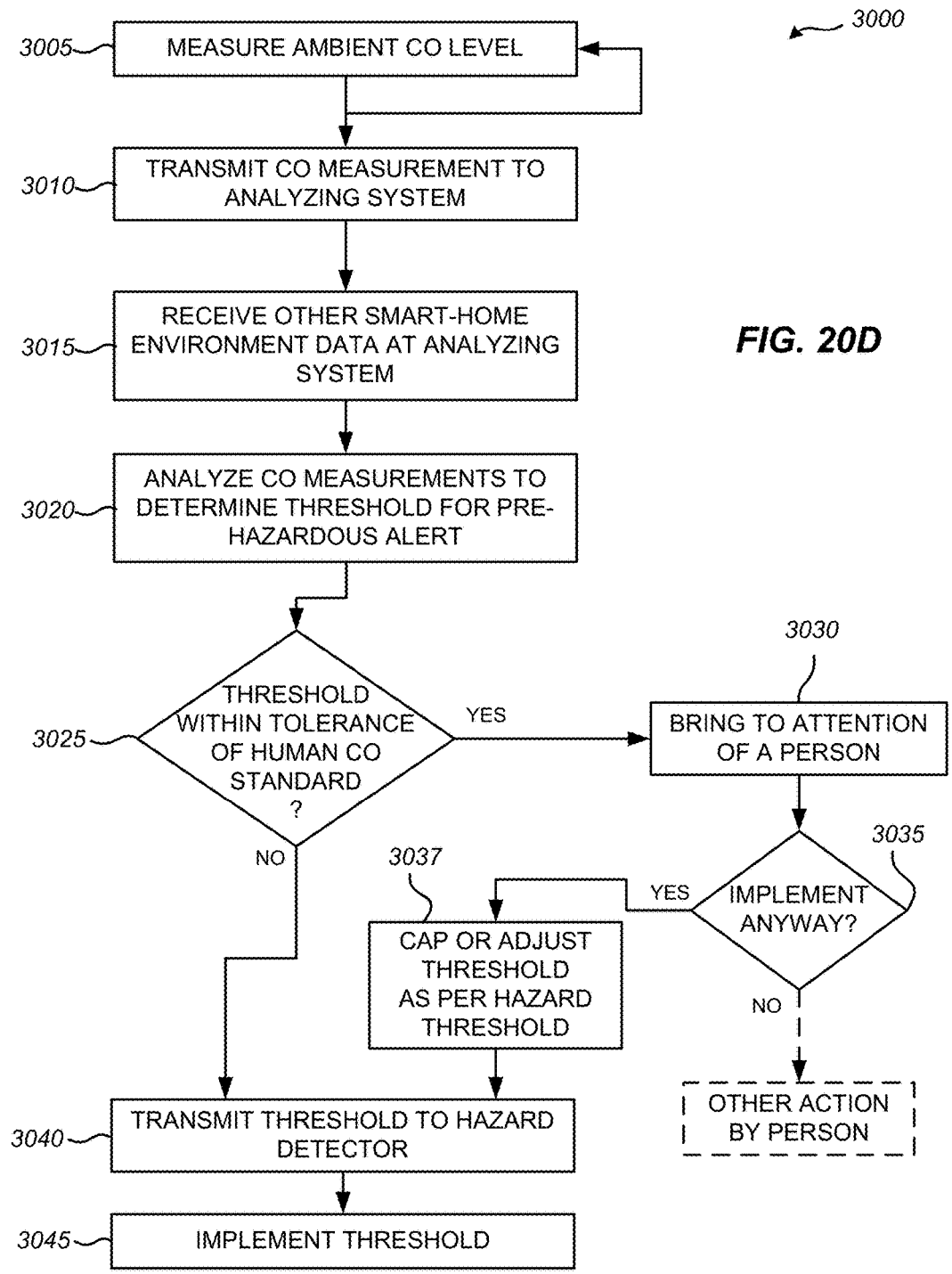
FIG. 20D illustrates a method of setting a pre-hazardous CO alarm threshold for a smart-home environment, according to an embodiment.

FIG. 20D is a flowchart of a method 3000 of determining CO baseline conditions and setting alarm thresholds in a smart-home environment. In embodiments, method 3000 is typically used to set an alarm threshold for pre-hazardous CO conditions at a particular location in a particular smart-home environment, so that pre-hazardous condition alarms represent abnormal CO increases for that particular location and environment. However, the threshold is generally set much lower than a dangerous CO level, so that causes can be determined and/or a CO increase can be brought to a user's attention well before safety becomes an issue. It is also possible to set multiple thresholds for pre-hazardous CO alerts, as discussed further below in connection with FIG. 20E.

Method 3000 begins with step 3005 measuring an ambient CO level. An example of step 3005 is hazard detector 104 measuring CO level at its location. Hazard detector 104 typically continues to measure CO level such that method 3000 shows step 3005 continuously repeating, in addition to the further steps of the method. In an optional step 3010, the CO measurement, the identity or location of the hazard detector 104 that measured the CO, and time of day that the CO was measured, are transmitted to an analyzing system. Step 3010 need not be performed when hazard detector 104 is the analyzing system. Examples of step 3010 are hazard detector 3010 transmitting CO data to a smart thermostat 102, computer 166 or cloud-computing system 164 (for example, by way of wireless router 160, FIG. 1). Step 3010 optionally also includes transmitting a time of day of the CO measurement transmitted; the time of day information is not required in all embodiments and/or may be inferred by the analyzing system (e.g., a time of day that the measured data is received by the analyzing system may be considered as the time of day of the measurement). In another optional step 3015, method 3000 receives other smart-home environment data at the analyzing system. The other smart-home environment data could be anything measurable by smart devices, such as temperature, light, sound, smoke, motion, operational states, alarm states and the like. Any such data that is available in the smart-home environment may be possible to correlate directly or indirectly to CO measurements.

Step 3020 analyzes the CO measurements to determine a threshold for a pre-hazardous condition. Step 3020 is typically performed after a significant number of measurements exist, such as 30 or more measurements in a population. In one embodiment, the population represents all operating conditions, e.g., the CO measurements are not screened or segregated by time of day or in connection with other measurable events or circumstances. In other embodiments, the CO measurements are screened or analyzed as subsets according to time of day or other circumstances (see FIG. 20E). The analysis can be performed in a variety of ways, for example, the analyzing system may perform a mean and standard deviation analysis on the population of CO measurements, and assign a pre-hazardous condition threshold corresponding to mean plus two, three, four or more standard deviations. Alternatively, for a large population of CO measurements (e.g., more than 100 or 1000 measurements), the analyzing system may assign the threshold slightly above the highest CO measurement of the population. Those skilled in the statistical arts will appreciate that many forms of analyzing CO measurement populations to come up with alarm limits that represent CO excursions that are statistically significant, are possible.

An optional step 3025 compares the threshold to one or more other human CO exposure standards for validation. If the determined threshold exceeds and/or is within a predetermined tolerance of such standards, the calculated threshold may be optionally brought to a person's attention in step 3030. Step 3030 may bring the high determined threshold to a person's attention by highlighting it in a table of alert conditions, through an app alert, by generating a log message that is periodically reviewed, or by sending an email or text message to the person. The predetermined tolerance may be, for example, if the threshold is greater than 75% of an applicable UL standard, or one of the location-specific thresholds noted in column 2520, FIG. 17. The tolerance may also be considered in context of the type of exposure standard; for example thresholds that are near to long term exposure standards may be considered less important than threshold that are near to short term danger levels. The person to whose attention the threshold is brought may be a user or resident of the smart-home environment, or someone associated with a cloud-computing system that calculates the threshold. There are several reasons for bringing high calculated thresholds to someone's attention. A high threshold may signify that a particular smart-home environment has a chronic or poorly controlled CO source that needs to be understood; it may signify that the analysis that resulted in the high threshold was flawed and should be reviewed and corrected; and if implemented, an alerts based on a high threshold is possibly likely to be followed imminently by a hazardous condition alert, because the pre-hazardous condition alert is only slightly lower than the hazardous condition threshold. After review, the person who reviews the determined threshold may decide in step 3035 to implement the threshold anyway, or take some other action, such as order further measurements or investigate the smart-home environment for CO sources.

If the decision in step 3025 is that the threshold is not high enough to human exposure standards, or the result of a human decision in step 3035 is to implement the threshold anyway, the threshold determined in step 3020 may be capped or adjusted in step 3037 as compared to the applicable hazardous condition threshold (e.g., the pre-hazardous alert may be set equal to the hazard threshold, or automatically reduced by a factor such as 10% or 20% relative to the hazard threshold). The threshold is then transmitted back to the hazard detector 104 that took the original measurements in a step 3040, in cases where the analyzing system was not the hazard detector itself. In step 3045, the threshold is implemented as a pre-hazardous condition alert threshold in the hazard detector 104.

Method 3000, FIG. 20D, calculates and implements a single CO threshold. When a single threshold is deemed adequate for all situations, times of day and the like, method 3000 is adequate. However, in embodiments, multiple CO thresholds are desirable so that individual ones of the thresholds can be raised or lowered in accordance with unique circumstances. Multiple thresholds therefore allow low thresholds of known, well controlled locations, times or other circumstances, and higher thresholds for locations, times or other circumstances that are characterized by predictable CO excursions that would trigger nuisance alarms at the lower threshold.

Figure 20E:
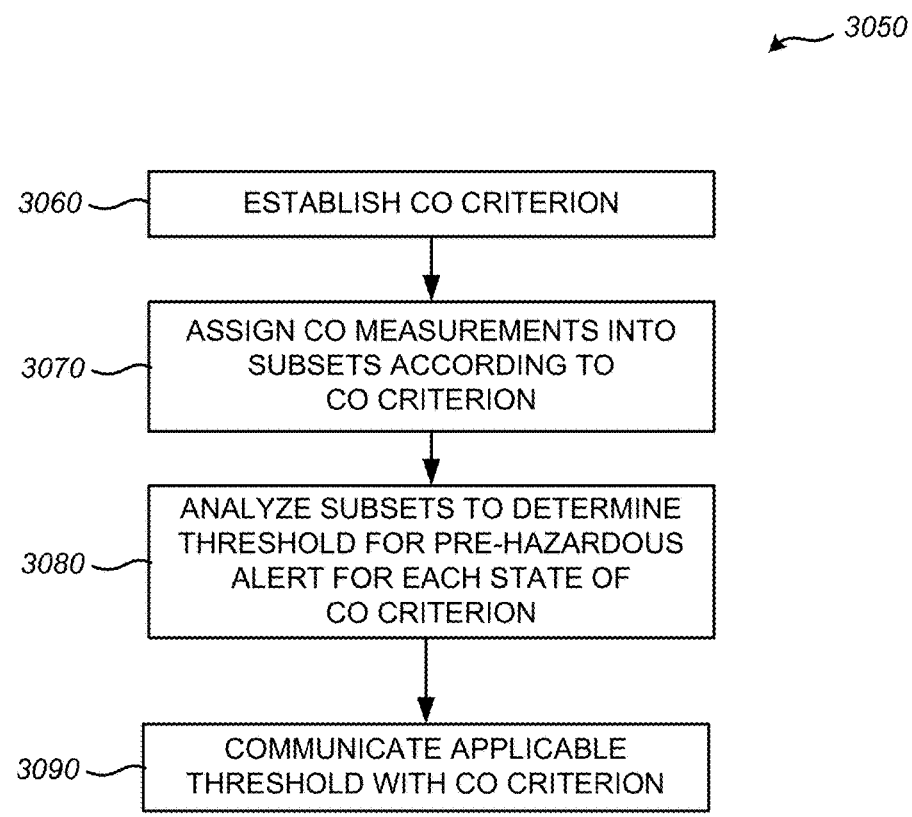
FIG. 20E illustrates a method of setting multiple pre-hazardous CO alarm thresholds for a smart-home environment, according to an embodiment.

FIG. 20E is a flowchart of a method 3050 of setting multiple pre-hazardous CO alarm thresholds for a smart-home environment. Method 3050 is substitutable for step 3020 of method 3000, FIG. 20D, in that it is performed by an analyzing system of the smart-home environment (e.g., one of the smart devices thereof, an app of an associated computing device such as computer 166, or cloud-computing system 164). Method 3050 will typically also be followed by steps 3025 and beyond of method 3000, such as validating the multiple CO thresholds against human CO standards and transmitting the thresholds back to a detector that will implement them.

Method 3050 begins with a step 3060 of establishing a CO criterion to distinguish two (or more) subsets of CO data. The CO criterion should be something that is available to the smart-home network on a continuous basis, such as time of day or a metric that can be evaluated with data generated by the smart-home network, such as a setting, a status code or correlation in time to a smart-home characteristic measured by one or more smart devices. For example, a simple CO criterion might be defined to distinguish CO measurements during a time block of 7:00 a.m. to 9:00 a.m. on weekdays, vs. all other times. Alternatively, more complex CO criteria may be established, such as any time within one-half hour of a certain door sensor (e.g., garage door or door from garage to house) being activated, any time within one hour of any motion being detected in a kitchen, or whether occupants are determined to be "at home" or "away" as described below. The CO criterion may be supplied by a user or administrator of the system, or it may be generated by an analyzing system of the smart-home network through correlation trials.

Once the CO criterion is established, method 3050 assigns existing CO measurement data (obtained by the analyzing system in steps 3005-3015, FIG. 20D) into subsets according to the CO criterion, in step 3070. In step 3080, each subset is analyzed to determine an appropriate threshold for a pre-hazardous alert. Evaluation of these subsets proceeds as described in step 3020, FIG. 20D, except that the evaluation is performed for each subset of the CO measurement data, producing a corresponding threshold for each of the subsets. When the multiple thresholds according to the subsets are communicated, the applicable CO criterion for each threshold is also communicated, in step 3090.

Once the multiple pre-hazardous CO thresholds are implemented, a hazard detector 104 may constantly evaluate and utilize the CO criterion to determine which of the thresholds it should use to compare against a current CO level. Alternatively, the hazard detector 104 may not necessarily evaluate the CO criterion unless current CO exceeds a first threshold, whereupon it will evaluate the CO criterion to determine whether current conditions call for a different threshold to be used.

Exemplary Computer Environments, Including Special Purpose Computers

Figure 21:
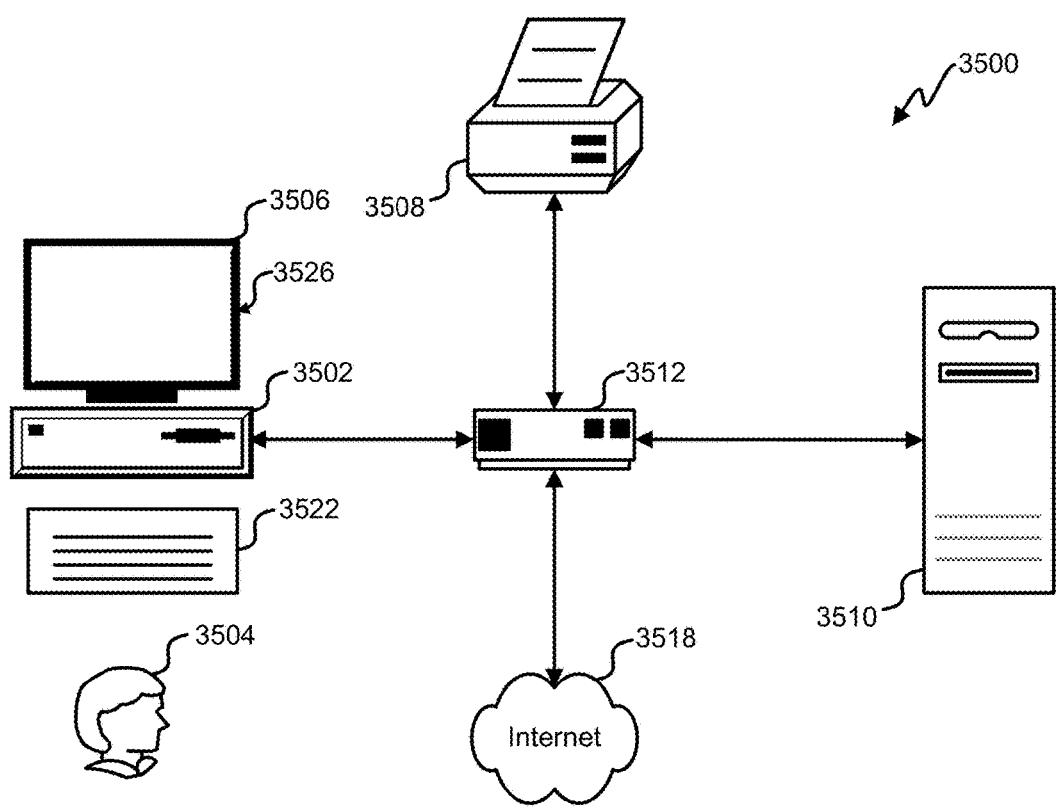
FIG. 21 illustrates an exemplary environment with which embodiments may be implemented with a computer system that can be used by a user to remotely control, for example, one or more of the sensor-equipped smart-home devices, according to one or more embodiments.

Referring next to FIG. 21, an exemplary environment with which embodiments may be implemented is shown with a computer system 3500 that can be used by a user 3504 to remotely control, for example, one or more of the sensor-equipped smart-home devices according to one or more of the embodiments. Computer system 3500 can alternatively be used for carrying out one or more of the server-based processing paradigms described hereinabove or as a processing device in a larger distributed virtualized computing scheme for carrying out the described processing paradigms, or for any of a variety of other purposes consistent with the present teachings. Computer system 3500 can include a computer 3502, keyboard 3522, a network router 3512, a printer 3508, and a monitor 3506. Monitor 3506, processor 3502 and keyboard 3522 may be considered part of a computer system 3526, which can be a laptop computer, desktop computer, handheld computer, mainframe computer, etc. Monitor 3506 can be a CRT, flat screen, etc.

A user 3504 can input commands into computer 3502 using various input devices, such as a mouse, keyboard 3522, a track ball, a touch screen, etc. If computer system 3500 includes a mainframe, user 3504 may access the computer 3502 using, for example, a terminal or terminal interface. Additionally, computer system 3526 may be connected to a printer 3508 and a server 3510 using a network router 3512, which may connect to the Internet 3518 or a WAN.

Server 3510 may, for example, store additional software programs and data. In one embodiment, software implementing the systems and methods described herein can be stored on a storage medium in server 3510. Thus, the software can be run from the storage medium in server 3510. In another embodiment, software implementing the systems and methods described herein can be stored on a storage medium in computer 3502. Thus, the software can be run from the storage medium in computer 3502. Therefore, in this embodiment, the software can be used whether or not computer 3502 is connected to network router 3512. Printer 3508 may be connected directly to computer 3502, in which case, computer system 3526 can print whether or not it is connected to network router 3512.

Figure 22:
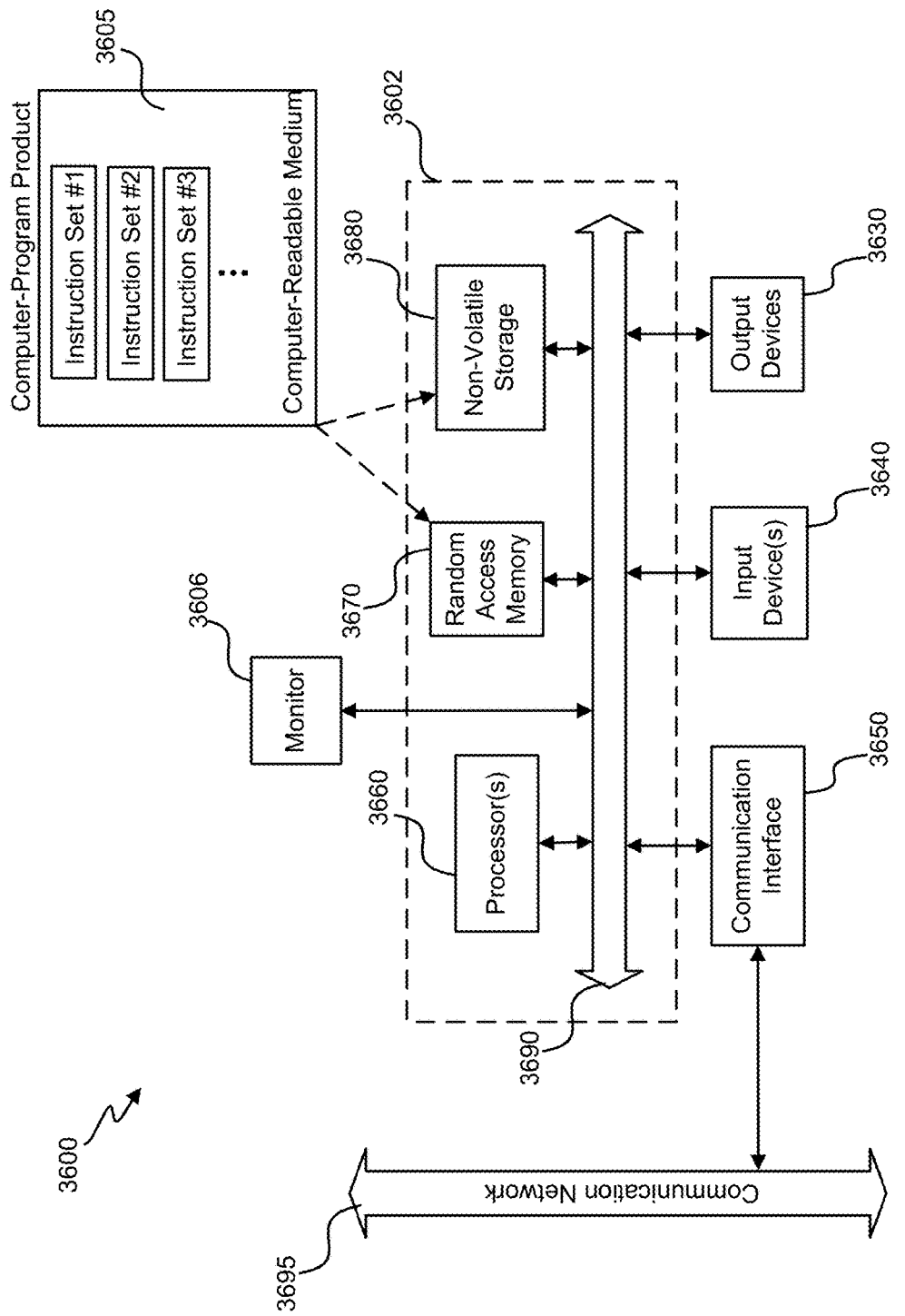
FIG. 22 schematically illustrates an embodiment in the form of a special-purpose computer system.

FIG. 22 schematically illustrates an embodiment in the form of a special-purpose computer system 3600. For example, one or more intelligent components, one or more processing engines 206 and/or components thereof may reside in special-purpose computer system 3600. The above methods may be implemented by computer-program products that direct a computer system to perform the actions of the above-described methods and components. Each such computer-program product may comprise sets of instructions (codes) embodied on a non-transitory, computer-readable medium that directs the processor of a computer system to perform corresponding actions. The instructions may be configured to run in sequential order, or in parallel (such as under different processing threads), or in a combination thereof. After loading the computer-program products on a general purpose computer system 3626, it is transformed into the special-purpose computer system 3600.

Special-purpose computer system 3600 comprises one or more of a computer 3602, a monitor 3606 coupled to computer 3602, one or more additional user output devices 3630 (optional) coupled to computer 3602, one or more user input devices 3640 (e.g., keyboard, mouse, track ball, touch screen) coupled to computer 3602, an optional communications interface 3650 coupled to computer 3602, and/or a computer-program product 3605 stored in a tangible computer-readable memory in computer 3602. Computer-program product 3605 directs system 3600 to perform the above-described methods. Computer 3602 may include one or more processors 3660 that communicate with a number of peripheral devices via a bus subsystem 3690. These peripheral devices may include user output device(s) 3630, user input device(s) 3640, communications interface 3650, and a storage subsystem, such as random access memory (RAM) 3670 and non-volatile storage 3680 (e.g., a disk drive, an optical drive, and/or non-transitory, solid state memory such as Flash, one-time programmable, or read-only memory), which are forms of tangible computer-readable memory.

Computer-program product 3605 may be stored in non-volatile storage 3680 or another computer-readable medium accessible to computer 3602 and loaded into memory 3670. Each processor 3660 may comprise a microprocessor, such as a microprocessor from Intel® or Advanced Micro Devices, Inc.®, or the like. To support computer-program product 3605, the computer 3602 runs an operating system that handles the communications of product 3605 with the above-noted components, as well as the communications between the above-noted components in support of the computer-program product 3605. Exemplary operating systems include Windows® or the like from Microsoft Corporation, Solaris® from Sun Microsystems, LINUX, UNIX, and the like.

User input devices 3640 include all possible types of devices and mechanisms to input information to computer system 3602. These may include a keyboard, a keypad, a mouse, a scanner, a digital drawing pad, a touch screen incorporated into a display, audio input devices such as voice recognition systems, microphones, and other types of input devices. In various embodiments, user input devices 3640 are typically embodied as a computer mouse, a trackball, a track pad, a joystick, wireless remote, a drawing tablet, a voice command system. User input devices 3640 typically allow a user to select objects, icons, text and the like that appear on the monitor 3606 via a command such as a click of a button or the like. User output devices 3630 include all possible types of devices and mechanisms to output information from computer 3602. These may include a display (e.g., monitor 3606), printers, and/or non-visual displays such as audio output devices, etc.

Communications interface 3650 provides an interface to other communication networks and devices and may serve as an interface to receive data from and transmit data to other systems, WANs and/or the Internet 3518. Embodiments of communications interface 3650 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 3650 may be coupled to a computer network, to a FireWire® bus, or the like. In other embodiments, communications interface 3650 may be physically integrated on the motherboard of computer 1602, and/or may be a software program, or the like.

RAM 3670 and non-volatile storage 3680 are examples of tangible computer-readable media configured to store data such as computer-program product embodiments of the present invention, including executable computer code, human-readable code, or the like. Other types of tangible and/or non-transitory computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 3670 and non-volatile storage 3680 may be configured to store the basic programming and data constructs that provide the functionality of various embodiments of the present invention, as described above.

Software instruction sets that provide the functionality of the present invention may be stored in RAM 3670 and non-volatile storage 3680. These instruction sets or code may be executed by the processor(s) 3660. RAM 3670 and non-volatile storage 3680 may also provide a repository to store data and data structures used in accordance with the present invention. RAM 3670 and non-volatile storage 3680 may include a number of memories including a main random access memory (RAM) to store instructions and data during program execution and a read-only memory (ROM) in which fixed instructions are stored. RAM 3670 and non-volatile storage 3680 may include a file storage subsystem providing persistent (non-volatile) storage of program and/or data files. RAM 3670 and non-volatile storage 3680 may also include removable storage systems, such as removable flash memory.

Bus subsystem 3690 provides a mechanism to allow the various components and subsystems of computer 3602 to communicate with each other as intended. Although bus subsystem 3690 is shown schematically as a single bus, alternative embodiments of the bus subsystem may utilize multiple busses or communication paths within the computer 3602.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, transitory, non-transitory, and/or other storage medium and is not to be limited to any particular type, number or configuration of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

A hazard detector according to an embodiment of the present invention may include a smoke, carbon monoxide (CO) and heat alarm for residential applications, similar to other hazard detectors discussion herein (e.g., smart hazard detectors 104 and 400, as shown in FIGS. 1 and 4, respectively). This hazard detector may utilize batteries (e.g., six lithium AA batteries or the batteries of battery pack 450, as shown in FIG. 4A). Alternatively, a hazard detector may be hard-wired, e.g., hard-wired via a 120V home power line, and/or may include a backup battery, e.g., any of the batteries discussed herein.

A hazard detector may advantageously integrate seven sensors: a photoelectric smoke sensor, a heat sensor, a carbon monoxide sensor that may last approximately 7 years, an ultrasonic sensor (e.g., first and second ultrasonic sensors 972 and 974, as shown in FIG. 5A), an occupancy sensor (e.g., a PIR sensor), an ambient light sensor and a humidity sensor. The use of these different sensors, in addition to advanced algorithms (e.g., as referenced in relation to FIGS. 1-5B) may allow the hazard detector to use multi-criteria detection to provide numerous features and functionality in addition to the features required by applicable regulatory agencies for basic alarm/detection functionality. Data from the temperature, humidity, occupancy and ambient light sensors may also be shared with other network connected devices (e.g., any of the devices shown in FIG. 1).

A number of different features related to alarms and hazard detector functionality verification of a hazard detector are now described.

For the purpose of detecting smoke, carbon monoxide and heat and generating corresponding emergency alarms, the hazard detector may include a photoelectric smoke sensor, a carbon monoxide sensor that may follow the time response required by Underwriters' Laboratories ("UL"), and a heat sensor whose sensitivity may be "135". The hazard detector may provide voice alarms with hazard location and call-to-action information. For example, to alert users that a danger or hazard has been sensed by the hazard detector, the hazard detector may generate voice alarms that include speech to announced what type of danger has been sensed (e.g., Smoke, CO, and/or Heat), where the danged has been sensed (e.g., in the living room, the bedroom, or a specific bedroom), and how the user should respond to the sensed danger (e.g., get out of a specific room or a residence). The voice alarms may also include the sound patterns required by applicable hazard detector regulations. For example, if smoke is sensed in the hallway, the hazard detector may generate the following voice alarm: "Honk, honk. EMERGENCY! There is smoke in the Hallway. Get out now." "Honk," as used herein, may refer to a shrill, loud, piercing audio sound or any other sound traditionally associated with a "honk" sound. As another example, if carbon monoxide is sensed in the hallway, the hazard detector may generate the following voice alarm: "Honk, honk. EMERGENCY! There is carbon monoxide in the hallway. Move to fresh air immediately." During an alarm, lights (e.g., LED lights) of the hazard detector may flash red or another color. In order to provide the hazard detector's location during an alarm, the hazard detector may be associated with a room of a residence or other building during the hazard detector setup process (e.g., using method 1300, FIG. 6).

The hazard detector may be installed in multiple locations in a single home or other building. Some or all of these hazard detectors can be interconnected wirelessly. As such, when a first hazard detector located in a hallway senses smoke and generates an alarm, other hazard detectors interconnected with the first hazard detector may wirelessly receive a command to generate the same voice alarms. The wireless interconnection between hazard detectors may occur over 6LoWPAN or other low-power communication protocols, and may not require a Wi-Fi connection or use of a mobile device application or app (e.g., application 1414, as shown in FIGS. 7-10) to establish the wireless interconnection. Even when multiple hazard detectors in a home generate the same voice alarm, a user may be able to quickly identify the first hazard detector—the hazard detector that first sensed the hazard and generated a corresponding alarm—because the name of the first hazard detector's location (e.g., the bedroom or the kitchen) may be included in the voice alarm.

Users may temporarily silence or "hush" certain alarms of the hazard detector by waving at the hazard detector, as described below. However, the hazard detector alarm may only be temporarily silenced and only if the sensed hazard levels are within a range in which applicable regulatory agencies allow hazard detector alarms to be silenced. "Waving," as used above, refers to a user's movement of his or her hand and/or other body part back and forth and/or up and down. The hazard detector may determine when waving is occurring using methods described in the following related U.S. patent application: U.S. Prov. Ser. No. 61/847,960 filed Jul. 18, 2013 (Ref. No. NES0307-PROV). Waving may be more convenient for users than climbing on a ladder or using a broom to reach the hazard detector and manually depress a silencing button thereon. As an example, during an alarm and/or a Heads Up pre-alarm (as described below), the hazard detector may determine that someone is within the sensing range of the occupancy sensor of the initiating hazard detector. Thereafter, when waving is detected by that hazard detector, it may generate a speech stating that the alarm will be silenced or hushed temporarily. The hazard detector may be configured such that only adult-sized users can silence or hush a voice alarm; this feature may be operable to exclude children and pets from being able to silence an alarm. For example, sensitivity of motion sensors of the hazard detector may be set such that only adult-sized users (including adult users in a wheelchair) can be sensed for the purpose of detecting waving to silence or hush an alarm. The hazard detector may also include, for example, a hush/test button that can be depressed to hush or silence an alarm.

In addition to the voice alarms described above, the hazard detector may provide additional early notifications, referred to herein as pre-alarming or heads-up notifications, of an evolving situation, or progressively more dangerous hazard levels. That is, heads-up notifications provide a warning to the user that a pre-hazardous condition has been detected in which there are elevated readings corresponding to the type of hazard being detected, but those readings do not yet rise to levels corresponding to an actual alarm condition. Generally, a pre-alarm or heads-up condition is one that merits more immediacy of concern than those underlying typical, persistent-yet-pleasant modulated glow levels of communication that are provided by smart thermostats and smart hazard detectors herein. A pre-alarm or heads-up condition may be accompanied by an immediate audible message. However, heads-up notifications may provide a friendlier voice alarm—in terms of content and tone—to alert users when smoke and/or CO are rising toward, but have not reached, hazardous levels. For example, the friendlier voice may be more calm, use less urgent language and may not be accompanied by sound patterns typically associated with emergency situations (e.g., a doorbell chime instead of a siren). As such, heads-up notifications may avoid alarming users to a degree that is not commensurate with the urgency of a given detected hazard level, while still alerting the user to a situation that may require attention. For example, if the hazard detector senses low levels of smoke, the hazard detector may generate the following speech "Heads up. There is smoke in the kitchen. The horn may sound." During a heads-up voice alarm, lights (e.g., LED lights) of the hazard detector may flash yellow. Heads-up notifications may be disabled via a mobile application (e.g., application 1414, as shown in FIGS. 7-10), by the hazard detector's online management account (e.g., the online management account discussed in relation to FIG. 6), and/or at the hazard detector's user interface.

Gating Gesture Hush

Figure 23:
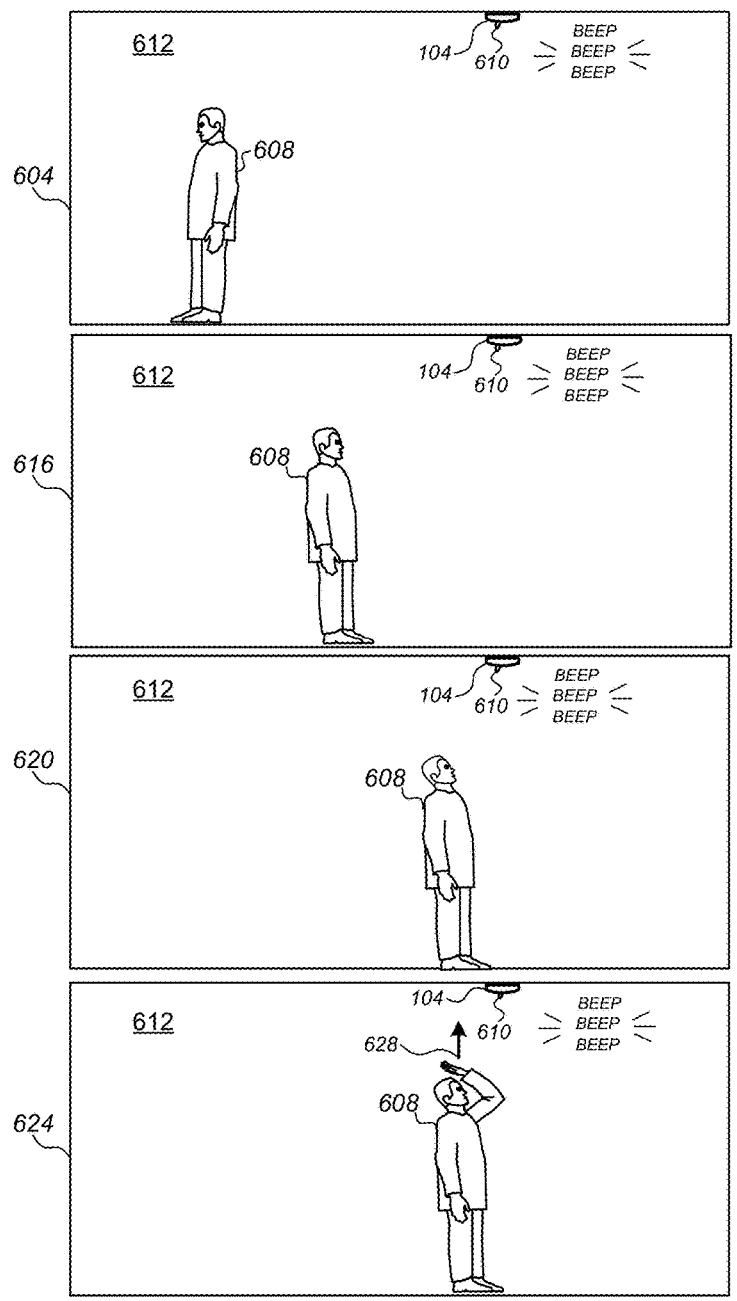
FIG. 23 illustrates interaction of a user with a smart hazard detector to deactivate or "hush" an alarm, according to an embodiment.
Figure 24:
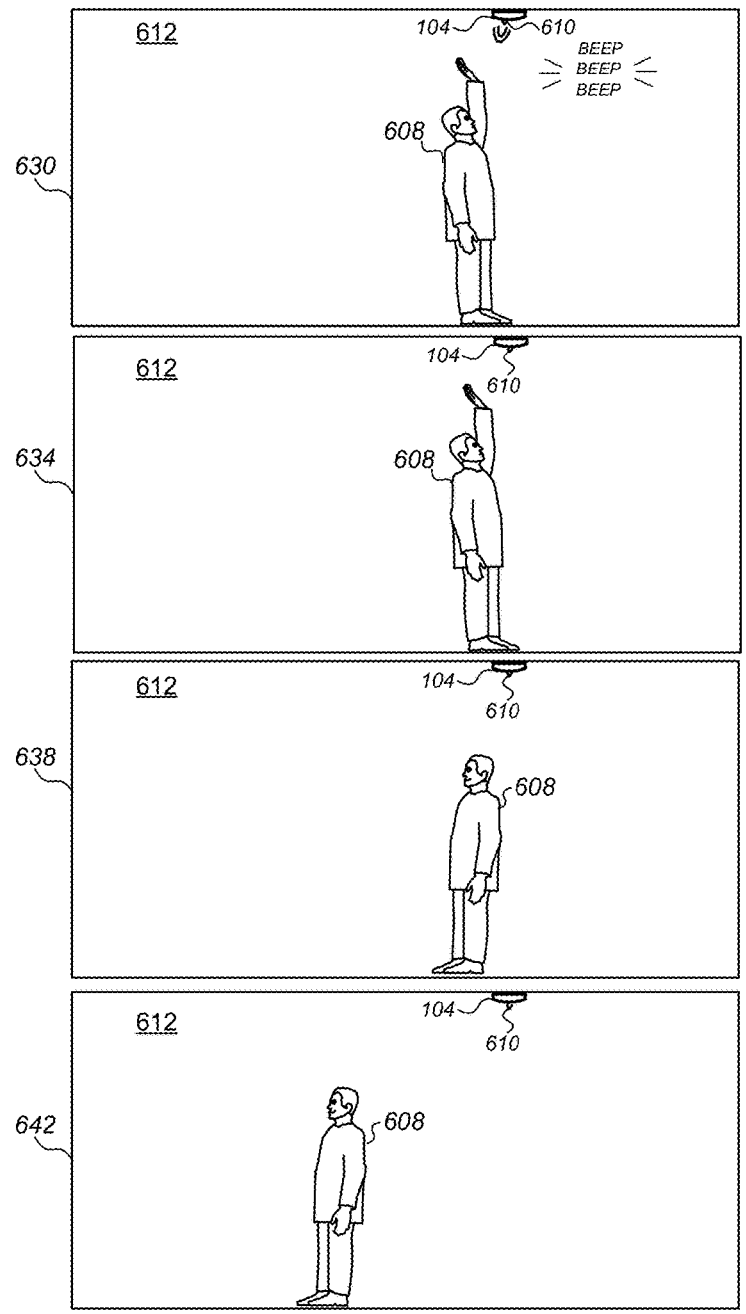
FIG. 24 illustrates interaction of a user with a smart hazard detector to deactivate or "hush" an alarm, according to an embodiment.

Referring now to FIGS. 23 and 24, interaction of a user 608 with a smart hazard detector 104 by providing exemplary "silence gestures" to deactivate or "hush" an alarm will be described. In the event hazard detector 104 is sounding an alarm, a user can walk to a position proximate the hazard detector 104 and provide a silence gesture to cause the hazard detector to stop alarming. The signal or input that is received by smart hazard detector 104 or other smart devices herein may be referred to as "gesture input." As shown in FIG. 23 at step 604, an occupant is standing in room 612 while an alarm in smoke or hazard detector 104 is active and making a "BEEP" sound. A light 610, such as an LED, is provided on an outer portion of the smart hazard detector 104, such that the occupant 608 can see the light 610 when it is turned on. The operation of the light 610 will be described with reference to FIG. 24. Suffice to say for FIG. 23, the light is turned off in steps 604 through 624. As shown at step 616, the occupant 608 has walked to a position closer to the smart hazard detector 104, which is mounted out of reach on the ceiling of the room. As shown at step 620, the occupant 608 walked to a position even closer to the smart hazard detector 104, such that the occupant 608 is almost directly under the smart hazard detector 104. As shown at arrow 628 of step 624, the occupant 608, while standing almost directly under the smart hazard detector 104, is beginning to extend an arm upward, toward the smart hazard detector 104.

Referring now to step 630 of FIG. 24, the arm of the occupant 608 is extended upward, toward the smart hazard detector 104, while the occupant is standing almost directly under the smart hazard detector 104. After an alarm sounds and the pulse rate increases, the ultrasonic sensor the smart hazard detector 104 "looks" for a trigger to the "silence gesture" period, which is the amount of time the "silence gesture" must be maintained to deactivate the alarm. According to some embodiments, the trigger is a distance change from a baseline, and to deactivate the alarm the distance change must be maintained for the entire "silence gesture" period (e.g., three seconds). For example, if the baseline is a distance between the sensor and the floor of the room, then the sensor is looking for an object to come in between it and the floor, thereby changing the distance measured by the sensor. In some embodiments, the distance change must be significant enough to ensure that someone is close and likely intends to silence the alarm. For example, if the distance to the floor is ten feet, then the requisite distance change could be eight feet or eighty percent of the original distance. As such, the object would be required to be within two feet of the sensor to trigger the "silence gesture" period, and to deactivate the alarm, the object must remain there for the duration of the period. The requisite distance change can be configured based on the height of the ceiling and based on the height of the occupants, among other things.

Referring still to step 630, the light 610 is turned on when the occupant 608 successfully triggers the "silence gesture" period, thereby signaling to the occupant 608 to remain in the position for the requisite period, such as three seconds. Here, the hand of the occupant 608 triggered the "silence gesture" period. A tolerance is built in such that if the occupant 608 slightly moves and loses but quickly regains the signal, the "silence gesture" period will continue without having to start over. As shown in step 634, the occupant kept the hand in within the requisite distance of the sensor for the duration of the "silence gesture" period and, thus the alarm has been deactivated, the "BEEP" has stopped, and the light 610 has turned off. As shown at steps 638 and 642, the occupant 608 can walk away from the smart hazard detector 104 and resume normal activity.

It should be appreciated that, in the event the smart hazard detector 104 is of a design that receives reliable power from the wiring of the home (rather than being battery powered), a CCD chip could be used to detect gesture input such as the "silence gesture". However, such an arrangement may be less suitable than ultrasonic sensors (e.g., ultrasonic sensors 972 and 974, FIG. 5A) for battery-powered hazard detectors 104 because the CCD chips and associated processing can consume a relatively large amount of power and may quickly drain the battery. Other possible alternatives to ultrasonic sensors 972 and 974 include passive IR sensors, thermopile (e.g., thermo-cameras), laser-distance measuring, laser and camera combinations wherein, for example, a camera looks for a laser dot instead of time of arrival (Doppler shift), and full on camera and image processing systems.

According to some embodiments, to enhance the reliability and effectiveness of gesture input, the ultrasonic sensor 972 and/or 974 could work in concert with a PIR sensor to make the sensing even better. For example, when an occupant attempts to silence by placing a hand in a field of view of the PIR sensor, the PIR sensor may sense this, and thereby trigger the "silence gesture" or "hushed" period. The ultrasonic sensor 972 and/or 974 could also work in concert with the thermopile (e.g., thermo-camera), where both distance change and heat are used to detect the "silence gesture." For example, the thermo-camera detects when human hand is nearby and triggers the "silence gesture" period. Further, ultrasonic sensors 972 and/or 974 may work in concert with an ambient light sensor. For example, when a user places a hand in s field of view of an ambient light sensor and blocks light thereon, then the ambient light sensor knows that the occupant is nearby and thus triggers the "silence gesture" period.

It should be appreciated that, according to embodiments, similar gesture input can be recognized by other smart devices in the home, such as the smart thermostat, the smart wall switches, etc. For example, there can be gestures for increasing or decreasing temperature controls, for turning on and off lights, HVAC, etc.

It should be appreciated that, according to embodiments, an occupancy sensor "gates" the silence gesture by only permitting a silence gesture to occur if the room is occupied. In other words, hazard detector 104 may not "listen" for a silence gesture unless it determines that the room is occupied. By disabling its silence gesture feature when the room is unoccupied, hazard detector ensures that the silence gesture feature does not malfunction during an alarm event and improperly deactivate an alarm.

Smart Thermostat

Figure 25A:
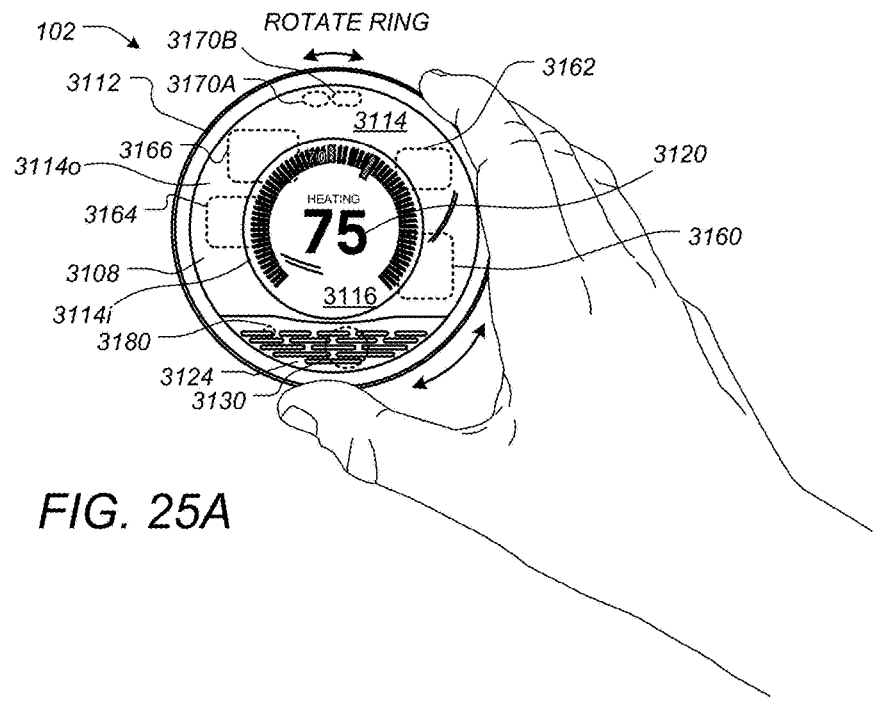
FIGS. 25A and 25B schematically illustrate, in front and perspective views respectively, an intelligent, multi-sensing, network connected thermostat, according to an embodiment.
Figure 25B:
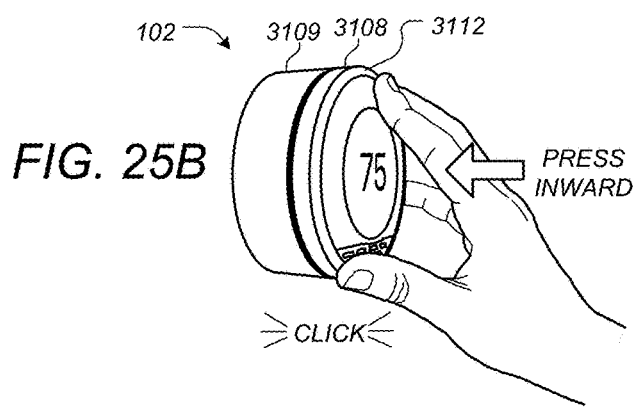

Turning now to FIGS. 25A-B, illustrations of a smart thermostat 102 are provided, according to some embodiments. Unlike many prior art thermostats, smart thermostat 102 may provide a sleek, simple, uncluttered and elegant design that does not detract from home decoration, and indeed can serve as a visually pleasing centerpiece for the immediate location in which it is installed. Moreover, user interaction with smart thermostat 102 is facilitated and greatly enhanced over known conventional thermostats by the design of smart thermostat 102. The smart thermostat 102 includes control circuitry and is electrically connected to an HVAC system, such as is shown with unit 103 in FIG. 1. Smart thermostat 102 is wall mounted, is circular in shape, and has an outer rotatable ring 3112 for receiving user input. Smart thermostat 102 is circular in shape in that it appears as a generally disk-like circular object when mounted on the wall.

The outer rotatable ring 3112 allows the user to make adjustments, such as selecting a new target temperature. For example, by rotating the outer ring 3112 clockwise, the target temperature can be increased, and by rotating the outer ring 3112 counter-clockwise, the target temperature can be decreased. The smart thermostat 102 may be configured to receive a plurality of types of inputs by virtue of the rotatable ring 3112, such as a scrolling input and a selection input. For example, a rotation of the ring may allow a user to scroll through an array of selection options, and inwards pressure exerted on the ring (inward click) may allow a user to select one of the options (e.g., corresponding to a particular scroll position).

The front face of the smart thermostat 102 comprises a clear cover 3114 that according to some embodiments is polycarbonate, and a metallic portion 3124 that may advantageously have a number of slots formed therein, as shown. Metallic portion 3124 as incorporated in smart thermostat 102 does not detract from home or commercial decor, and indeed can serve as a visually pleasing centerpiece for the immediate location in which it is located.

Although being formed from a single lens-like piece of material such as polycarbonate, the cover 3114 has two different regions or portions including an outer portion 3114*o* and a central portion 3114*i*. According to some embodiments, the cover 3114 is painted or smoked around the outer portion 3114*o*, but leaves the central portion 3114*i* visibly clear so as to facilitate viewing of an electronic display 3116 disposed thereunderneath. According to some embodiments, central display 3116 is a backlit color liquid crystal display (LCD). An example of information displayed on the electronic display 3116 is illustrated in FIG. 25A, and includes central numerals 3120 that are representative of a current setpoint temperature.

Particular presentations displayed on the electronic display 3116 may depend on detected user input. For example, one of a plurality of variables (e.g., current setpoint temperature versus learning status) or variable values (e.g., "65" versus "75") may be displayed. The one being displayed may depend on a user's rotation of the outer rotatable ring 3112. Thus, for example, when the device is configured to display a current setpoint temperature, the value being displayed may gradually increase as the user rotates the ring in a clockwise direction. The sign of the change in the displayed temperature may depend on whether the user is rotating the ring in a clockwise or counterclockwise direction. The speed at which the displayed temperature is changing may depend (e.g., in a linear manner) on the speed at which the user is rotating the ring.

The metallic portion 3124 is designed to conceal sensors from view promoting a visually pleasing quality of the thermostat yet permitting them to receive their respective signals. Openings in the metallic portion 3124 along the forward-facing surface of the housing allow signals to pass through that would otherwise not pass through the cover 3114. For example, glass, polycarbonate or other similar materials used for cover 3114 are capable of transmitting visible light but are highly attenuating to infrared energy having longer wavelengths in the range of 10 microns, which is the radiation band of operation for many passive infrared (PIR) occupancy sensors. Notably, included in the smart thermostat 102, according to some preferred implementations, is an ambient light sensor (not shown) and an active proximity sensor (not shown) positioned near the top of the thermostat just behind the cover 3114. Unlike PIR sensors, the ambient light sensor and active proximity sensor are configured to detect electromagnetic energy in the visible and shorter-infrared spectrum bands having wavelengths less than 1 micron, for which the glass or polycarbonate materials of the cover 3114 are not highly attenuating. In some implementations, the metallic portion 3124 includes openings in accordance with one or more implementations that allow the longer-wavelength infrared radiation to pass through the openings towards a passive infrared (PIR) motion sensor 3130 as illustrated. Because the metallic portion 3124 is mounted over the radiation receiving surface of PIR motion sensor 3130, PIR motion sensor 3130 continues to receive the longer wavelength infrared radiation through the openings and detect occupancy in an enclosure.

Additional implementations of the metallic portion 3124 also facilitate additional sensors to detect other environmental conditions. The metallic portion may at least partly conceal and/or protect one or more such sensors. In some implementations, the metallic portion 3124 helps a temperature sensor situated inside of the thermostat's housing measure the ambient temperature of air. Openings in the metallic portion 3124 promote air flow towards a temperature sensor located below the metallic portion 3124 thus conveying outside temperatures to the interior of the housing. In further implementations, the metallic portion 3124 may be thermally coupled to a temperature sensor promoting a transfer of heat from outside the housing.

An LED indicator 3180 can be used for communicating one or more status codes or error codes by virtue of red color, green color, various combinations of red and green, various different blinking rates, and so forth, which can be useful for troubleshooting purposes.

Motion sensing as well as other techniques can be used in the detection and/or prediction of occupancy, as it is described further in the commonly assigned U.S. Ser. No. 12/881,430, supra. According to some embodiments, occupancy information is used in generating an effective and efficient scheduled program. Advantageously, an active proximity sensor 3170A is provided to detect an approaching user by infrared light reflection, and an ambient light sensor 3170B is provided to sense visible light. The proximity sensor 3170A can be used to detect proximity in the range of about one meter so that the smart thermostat 102 can initiate "waking up" when the user is approaching the thermostat and prior to the user touching the thermostat. Such use of proximity sensing is useful for enhancing the user experience by being "ready" for interaction as soon as, or very soon after the user is ready to interact with the thermostat. Further, the wake-up-on-proximity functionality also allows for energy savings within the thermostat by "sleeping" when no user interaction is taking place our about to take place. The ambient light sensor 3170B can be used for a variety of intelligence-gathering purposes, such as for facilitating confirmation of occupancy when sharp rising or falling edges are detected (because it is likely that there are occupants who are turning the lights on and off), and such as for detecting long term (e.g., 24-hour) patterns of ambient light intensity for confirming and/or automatically establishing the time of day.

According to some embodiments, for the combined purposes of inspiring user confidence and further promoting visual and functional elegance, the smart thermostat 102 is controlled by only two types of user input, the first being a rotation of the outer ring 3112 as shown in FIG. 10A (referenced hereafter as a "rotate ring" or "ring rotation" input), and the second being an inward push on an outer cap 3108 (see FIG. 25B) relative to an outer shell 3109 until an audible and/or tactile "click" occurs (referenced hereafter as an "inward click" or simply "click" input). For the embodiment of FIGS. 25A and 25B, the outer cap 3108 is an assembly that includes all of the outer ring 3112, cover 3114, electronic display 3116, and metallic portion 3124. When pressed inwardly by the user, the outer cap 3108 travels inwardly by a small amount, such as 0.5 mm, against an interior metallic dome switch (not shown), and then springably travels back outwardly by that same amount when the inward pressure is released, providing a satisfying tactile "click" sensation to the user's hand, along with a corresponding gentle audible clicking sound. Thus, for the embodiment of FIGS. 25A and 25B, an inward click can be achieved by direct pressing on the outer ring 3112 itself, or by indirect pressing of the outer ring by virtue of providing inward pressure on the cover 3114, metallic portion 3124, or by various combinations thereof. For other embodiments, the smart thermostat 102 can be mechanically configured such that only the outer ring 3112 travels inwardly for the inward click input, while the cover 3114 and metallic portion 3124 remain motionless. It is to be appreciated that a variety of different selections and combinations of the particular mechanical elements that will travel inwardly to achieve the "inward click" input are within the scope of the present teachings, whether it be the outer ring 3112 itself, some part of the cover 3114, or some combination thereof. However, it has been found particularly advantageous to provide the user with an ability to quickly go back and forth between registering "ring rotations" and "inward clicks" with a single hand and with minimal amount of time and effort involved, and so the ability to provide an inward click directly by pressing the outer ring 3112 has been found particularly advantageous, since the user's fingers do not need to be lifted out of contact with the device, or slid along its surface, in order to go between ring rotations and inward clicks. Moreover, by virtue of the strategic placement of the electronic display 3116 centrally inside the rotatable ring 3112, a further advantage is provided in that the user can naturally focus their attention on the electronic display throughout the input process, right in the middle of where their hand is performing its functions. The combination of intuitive outer ring rotation, especially as applied to (but not limited to) the changing of a thermostat's setpoint temperature, conveniently folded together with the satisfying physical sensation of inward clicking, together with accommodating natural focus on the electronic display in the central midst of their fingers' activity, adds significantly to an intuitive, seamless, and downright fun user experience. Further descriptions of advantageous mechanical user-interfaces and related designs, which are employed according to some embodiments, can be found in U.S. Ser. No. 13/033,573, supra, U.S. Ser. No. 29/386,021, supra, and U.S. Ser. No. 13/199,108.

According to some embodiments, the smart thermostat 102 includes a processing system 3160, memory 3162, display driver 3164 and a wireless communications system 3166. The processing system 3160 may be disposed within a housing of smart thermostat 102, coupled to one or more temperature sensors of smart thermostat 102 and/or coupled to rotatable ring 3112. The processing system 3160 may be configured to dynamically identify user input via rotatable ring 3112, dynamically identifying a variable value (e.g., a setpoint temperature value), and/or dynamically identify an HVAC-control-related property. The processing system 3160 may be configured and programmed to provide an interactive thermostat menuing system on display area 3116 responsive to an inward pressing of rotatable ring 3112 and/or to provide user navigation within the interactive thermostat menuing system based on rotation of rotatable ring 3112 and inward pressing of rotatable ring 3112. The processing system 3160 may be adapted to cause the display driver 3164 and display area 3116 to display information to the user and/or to receive user input via the rotatable ring 3112. Memory 3162 may include volatile (e.g., RAM)

and/or nonvolatile memory (e.g., ROM and/or Flash memory) for storing information such as current and previous user-indicated settings, what type of heating system is associated with an HVAC system being controlled, and the like.

For example, an active variable (e.g., variable-value selection, setpoint selection, zip-code selection) may be determined based on a default state, smart logic or previously received user input. A relationship between the variable and user input may be identified. The relationship may be, e.g., linear or non-linear, continuous or discrete, and/or saturating or non-saturating. Such relationships may be pre-defined and stored within the thermostat. User input may be detected. Analysis of the user input may include, e.g., identifying: a type of user input (tapping versus rotation), a degree of input (e.g., a degree of rotation); a final input position (e.g., a final angular position of the rotatable ring); an input location (e.g., a position of a tapping); and/or a speed of input (e.g., a speed of rotation). Using the relationship, the processing system 3160 may then determine a display indicator, such as a digital numerical value representative of an identified value of a variable (e.g., a setpoint temperature). The display indicator may be displayed on display area 3116. For example, a digital numerical value representative of a setpoint temperature to be displayed may be determined based on a prior setpoint value and a saturating and continuous relationship between rotation input and the temperature. The displayed value may be, e.g., numeric, textual or graphical.

The processing system 3160 may further set a variable value in accordance with a user selection. For example, a particular type of user input (e.g., inwards pressure exertion) may be detected. A value of a selected variable may be determined based on, e.g., a prior ring rotation, displayed variable value, etc. The variable may then be set to this value.

The processing system 3160, according to some embodiments, is capable of carrying out the governance of the operation of smart thermostat 102 including the user interface features described herein. The processing system 3160 is further programmed and configured to carry out other operations as described further hereinbelow and/or in other ones of the commonly assigned incorporated applications. For example, processing system 3160 is further programmed and configured to maintain and update a thermodynamic model for the enclosure in which the HVAC system is installed, such as described in U.S. Ser. No. 12/881,463. According to some embodiments, the wireless communications system 3166 is used to communicate with devices such as personal computers and/or other thermostats or HVAC system components, which can be peer-to-peer communications, communications through one or more servers located on a private network, and/or communications through a cloud-based service.

Hazard Detector Integration with Thermostat—Thermostat Displays Hazard Detector—Detected Alerts According to embodiments, the presentations on electronic display 3116 may reflect information provided to smart thermostat 102 from other smart devices (e.g., any of devices 104, 106, 108, 110, 112, 114, and/or 116, and others) in the smart-home environment 100. For example, upon detecting notable events, conditions, etc. in the home, other smart devices transmit information corresponding to the detected notable events, conditions, etc. to smart thermostats 102, which display corresponding messages on electronic displays 3116.

As described with reference to FIG. 1, the smart devices in the smart-home environment 100 are capable of data communications and information sharing with each other and with the central server or cloud-computing system 164. The data communications can be carried out using any of a variety of custom or standard wireless protocols (Wi-Fi, ZigBee, 6LoWPAN, etc.) and/or any of a variety of custom or standard wired protocols (CAT6 Ethernet, HomePlug, etc.) As described, all or some of the smart devices can serve as wireless or wired repeaters and combine to create a mesh network in the smart-home environment 100. In the event one of the smart devices detects a notable condition or event, it can send a corresponding message over the mesh network, and the other smart devices repeat the message, thereby causing the message to travel from smart device to smart device throughout the smart-home environment 100 as well as over the Internet 162 to the central server or cloud-computing system 164.

As illustrated in FIGS. 32A-C, upon detecting an alarm condition, hazard detector 104 sends a corresponding message that gets repeated through the mesh network to the one or more smart thermostats 102 located in the smart-home environment 100. Hazard detector 104 may detect a pre-hazardous or serious hazard condition that involves smoke, CO, and/or heat in a location of the home. In the event hazard detector 104 detects a pre-hazardous condition for smoke in the bedroom, it sends a corresponding message through the mesh network to one or more smart thermostats 102, which display a corresponding message. As illustrated in FIG. 32A, the electronic display 3116 of smart thermostat 102 displays a message 3205 saying, "There's smoke in the bedroom." In the event the smoke condition worsens and hazard detector 104 detects a serious hazard condition involving smoke in the bedroom, hazard detector sends a corresponding message through the mesh network to one or more smart thermostats 102, which display a corresponding message. As illustrated in FIG. 32B, the electronic display 3116 of smart thermostat 102 displays a message 3210 alerting users of the serious hazard condition by saying, "SMOKE in the bedroom GET OUT NOW".

Further, in the event hazard detector 104 determines that a previously detected alarm condition has cleared from a location, it sends a corresponding message through the mesh network to one or more smart thermostats 102, which display a corresponding message. For example, if after detecting a pre-hazardous or serious hazard condition involving smoke in the bedroom, hazard detector 104 later determines that the smoke has cleared from the bedroom, it sends a corresponding message. As illustrated in FIG. 32C, the electronic display 3116 of smart thermostat 102 displays a message 3215 saying, "Smoke in the bedroom has cleared."

As mentioned above, it should be appreciated that any of the smart devices in the smart-home environment 100 can send messages to smart thermostats 102 for display. In one example, upon a motion detector determining that a window in home has been breached, it or other smart devices in the home can send a corresponding message through the mesh network to smart thermostats 102, which, as illustrated in FIG. 32D, can display a message 3220 that says, "The window in the kids' bedroom has been jimmied".

In another example, smart doorbell 106 sends a message regarding a person at the door through the mesh network to smart thermostats 102. According to embodiments, technologies and sensors at the smart doorbell 106 may identify the person based on facial recognition or based on other characteristics such as "a signature" unique to the manner in which a particular person walks or otherwise moves when approaching the door. For example over time, based on input received from the smart doorbell 106, a central server or the smart doorbell 106 itself can build up an address book of profile data about people who approach the door. The address book may comprise some identifying biometric data for each person. For example, the address book can be built over time using low-resolution data such as ultrasonic, passive IR, etc. to create a unique signature for individuals. This becomes almost like a fingerprint regarding how that person approaches the house. In some instances, when a "familiar" person approaches the door, the smart doorbell 116 "asks" the person if he is "John Doe", to which the person can verbally or physically respond. Further, in addition to or instead of identification based on these unique "signatures", individuals may enable their mobile devices to communicate with the smart doorbell 116, such as via Bluetooth, NFC, or other wireless protocols. Also, for example, individual may "swipe" their smart phones in front of the smart doorbell's RFID scanner.

Upon identifying the individual standing near or approach a door, smart doorbell 106 may send a corresponding message through the mesh network to one or more smart thermostats 102 in the smart-home environment 100. For example, the message may indicate that a person is at or approaching the front door and the message may optionally include the person's name and/or an image of the person. Responsive to receiving such a message, smart thermostats 102 display corresponding information on electronic displays 3116. As illustrated in FIG. 32E, electronic display 3116 of smart thermostat 102 displays a message 3205 that says, "John Doe is at the door".

Determining User Location and Displaying Corresponding Messages

According to embodiments, user location(s) can be determined, corresponding messages can be displayed on smart devices associated with the smart-home environment 100, and inferences about CO sources and actions to be taken based on elevated CO levels can be adjusted according to the user location(s). For example, smart devices within the home and/or the central server or cloud-computing system 164 obtain location data, such as GPS data, from computers 166 of users, some of whom may have registered their computers 166 with the smart home, smart devices therein, and/or central server or cloud-computing system 164 as being associated with the smart-home environment 100. In some instances the central server or cloud-computing system 164 receives occupant-location data directly from the mobile devices, whereas in others the data is received or inferred from an intermediary, such as one of the smart devices in the home.

In instances where occupant-location data is received directly from the mobile device, the central server or cloud-computing system 164 can determine if the occupant is "at home" or "away", as explained below. When an occupant is at home, the central server or cloud-computing system 164 may be able to determine the occupant's actual room-location (e.g., bedroom, kitchen, garage, etc.). To do so, for example, the central server or cloud-computing system 164 cross-references the occupant-location (e.g., GPS coordinates) with a map of the home.

In instances where occupant-location data is received from a smart device located within the home, the central server or cloud-computing system 164 can infer that the occupant is inside the home. Further, the room-location of the occupants can be determined. For example, the smart wall switches 108, the smart wall plugs 110, the smart doorbells 106, and other smart devices in the smart-home environment 100 detect the presence of the computer 166 of the user and transmit corresponding data to the central server or cloud-computing system 164. Such detection of mobile devices can be accomplished using WiFi, Bluetooth, NFC, etc. It should also be appreciated that passive RFID tags can be used to determine the room-location of occupants (and pets). For example, an RFID may be associated with one or more of the occupants (and pets) of the house, such as by including the tags in wallets, bracelets, wristbands, mobile devices, collars, etc. The smart devices in the various rooms detect the RFID tags, and send that information to the central server or cloud-computing system 164. It should be appreciated that, because they are typically mounted in unobstructed locations, high on walls of often-occupied rooms, smart hazard detectors 104 are particularly well suited for RFID sensors.

Figure 26:
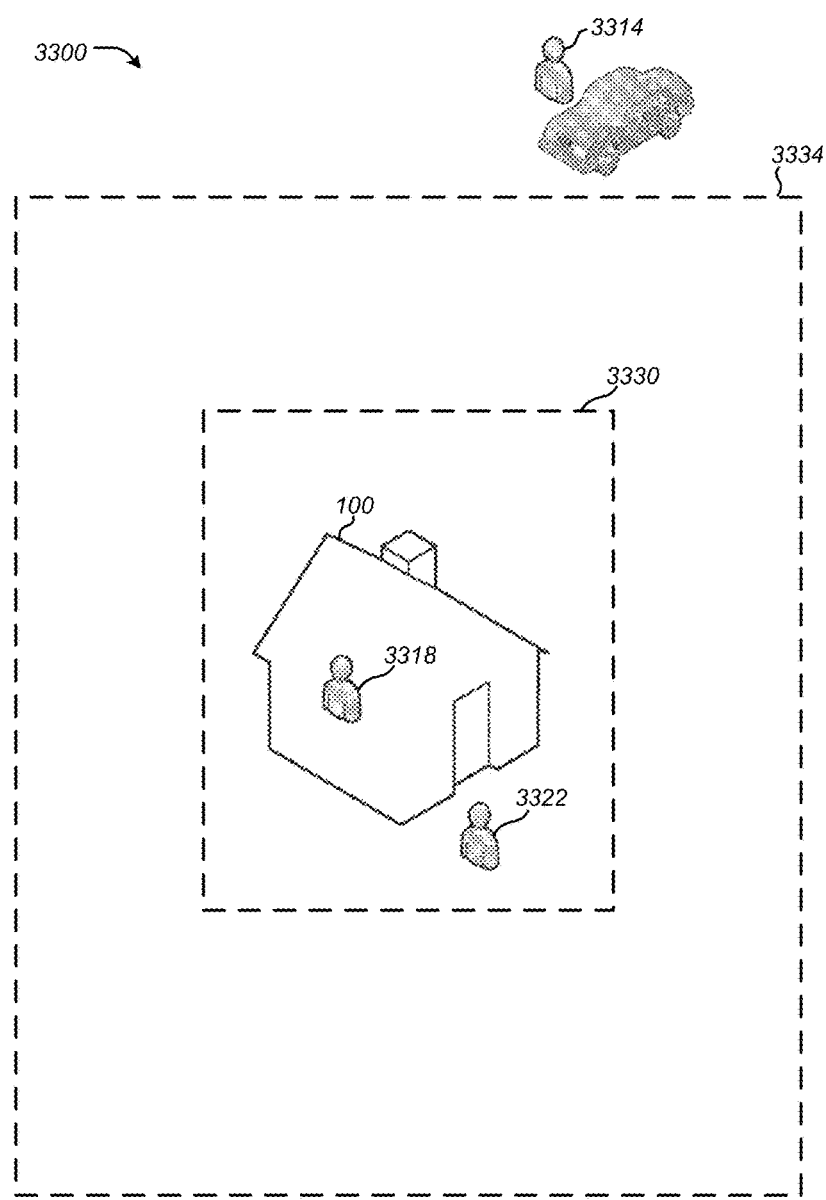
FIG. 26 is a schematic diagram illustrating geo-fencing, according to an embodiment.

In the example illustrated with reference to FIG. 26, the users include Wife 3314, Husband 3318 and Child 3322, all of whom have registered their computers 166 with the central server or cloud-computing system 164 (FIG. 1) as being associated with the smart-home environment 100. Further, two geo-location boundaries or "geo-fences" 3330, 3334 are registered as being associated with the smart-home environment 100. In some embodiments, the users, who are occupants of the home, define and register the geo-fences, while in other embodiments the central server or cloud-computing system 164 auto-generates the geo-fences for the home.

Inner geo-fence 3330 defines the perimeter of living area of the home. The area within the inner-geo fence includes not only the home but also the land immediately surrounding the house, including any closely associated structures, such as garages or sheds ("the curtilage"). Outer geo-fence 3334 defines an outer perimeter, which is sometimes miles from the home. The outer geo-fence 3334 is adjustable and extends well beyond the curtilage. For example, the perimeter defined by the outer geo-fence 3334 may have a radius of two to three miles in some embodiments, while in other embodiments the radius is larger or smaller.

According to embodiments, the central server or cloud-computing system 164 infers that an occupant is "at home" when inside the inner geo-fence 3330 and that the occupant is "away" when outside of the inner geo-fence 3330. Further, the central server or cloud-computing system 164 infers an occupant is going home when the occupant moves (e.g., travels by car) from outside to inside the outer geo-fence 3334. As such, the central server or cloud-computing system 164 uses the inner geo-fence 3330 to determine when occupants leave the home, and it uses the outer geo-fence 1334 to determine when occupants are heading home.

Several exemplary smart-home objectives will now be described. In one example, when an inference is made that a user is heading home, a corresponding message may be displayed on smart thermostats 102. For example, upon inferring that Wife 3314 is heading home, a corresponding message can be send to smart thermostat 102 causing smart thermostat to display on electronic display 3116 a message that says, "Wife is heading home". Likewise, when an inference is made that Wife 3314 is leaving home, a corresponding message can be displayed. When Wife 3314 arrives home an moves to a position near a door of the home, a corresponding message can be sent to smart thermostat 102 causing smart thermostat to display a message that says, "Wife is at the door". This inference can be made when Wife 3314 moves to a position close to or within inner geo-fence 3330 or to a position close enough that a computer 166 of Wife 3314 communicates with smart doorbell 106. Also for example, upon detecting that Child 3322 has moved into a different room of the home, a corresponding message can be sent to smart thermostat 102 causing smart thermostat to display a message that says, "Child is now in the kids bedroom". Room transitions, as discussed above, can be detected by smart devices in the home according to a number of techniques, including the smart devices communicating with the mobile device of the person making the transitions though the home. Further, as discussed above, GPS data can be used to detected occupant movement within the home.

When locations of occupants (including guests) within smart-home environment 100 can be determined with high confidence, significant enhancements to inferring causes and/or mitigating high CO levels may be possible. For example, presence of one or more occupants in certain rooms may make causes of high CO levels more plausible, due for example to cooking activity, smoking, or use of a legacy (e.g., not "smart") device such as a wood stove for heating. Such a scenario, if recurring, would most likely be recognizable within existing CO and home characteristic data as a likely cause for a high CO level. Also, known presence of one or more occupants may be used to elevate the importance of clearing a room of CO when dangerously high levels are detected, especially when the occupant appears unresponsive. For example, when a specific occupant's location is verifiable with high accuracy because of a mobile device or RFID tag that the person is known to always have with him/her, and that location has a high CO level, and there is no sign of activity from the occupant, very high priority can be placed on either trying to eliminate the source of the CO or to do everything possible to ventilate the location.

Smart Keypad

In some embodiments a network-connected smart keypad is provided in the smart-home environment 100. According to embodiments, an important underlying functionality of the smart keypad is to control the functionality of security features of the smart-home environment 100. It should be appreciated that the smart keypad is enhanced with a variety of multi-sensing capabilities that, while indeed enhancing home safety and security in many ways, can provide additional functionalities relating to controlling the other smart devices in the home, HVAC control, home energy conservation, intra-home communications, entertainment, etc.

According to embodiments, smart keypad includes powering circuitry, including a rechargeable battery, for extracting power as needed from the 120V "hot" line voltage wire. The rechargeable battery can either be used as a conventional back-up source or as a reservoir to supply excess DC power if needed for short periods.

According to some embodiments, like other smart-home devices described herein, the smart keypad is split into two parts: a head unit and a backplate. This bifurcation can increase the success and commercial longevity of the smart keypads by making them a modular platform consisting of two basic components. According to some embodiments, the backplate is a permanent interface box (sometimes referred to herein as "docking station") that serves as a physical connection into the wall and to the 120V line voltage wires or other wiring of the smart-home environment 100, and that contains AC-to-DC powering circuitry. When installed, the docking station may resemble a conventional one-gang or two-gang wall box, except no dangerous high-voltage wires are exposed to the user. According to some embodiments, docking station also includes a cellular wireless interface.

According to some embodiments, the head unit (sometimes referred to herein as "replacement module") actually contains all of the sensors, processors, user interfaces, the rechargeable battery, and so forth. Users can plug and unplug the unit in and out of the docking station. Many different commercial and functional possibilities for provisioning, maintenance, and upgrade are possible. For example, after years of using any particular head unit, a user will be able to buy a new version of the head unit and simply plug it into the docking station. There are also many different versions for the head unit, such as an extremely low-cost version that is nothing but a user interface, and then a progression of increasingly-capable version, up to and including extremely fancy head unit with small OLED televisions and high-fidelity mini-speakers. Thus, it should be appreciated that the various versions of the head units of the smart keypads and other smart devices can all be interchangeable, with any of them working when placed into any docking station. This can advantageously encourage sharing and re-deployment of old head units—for example, when an important high-capability head unit (for the kitchen or living room, for example) can replaced by a great new version of the head unit, then the old head unit can be re-deployed in a bedroom or a basement, etc. When first plugged into a docking station, the head unit can ask the user (by 2D LCD display, 2D/3D holographic projection, voice interaction, etc.) a few simple questions such as, "Where am I" and the user can select "bedroom" or "living room" and so forth. In other examples, the head unit can provide instructions, such as "Press button once if I am in the kitchen, press twice if I am in the den, etc."

According to some embodiments, the smart keypad contains a main processor, storage, display and user interface, audio speaker, microphone, power converter, GPS receiver, RFID locater, and general physical module receiver. The smart keypad further contains wireless and wired networking. In view of the ample power availability, a variety of communications capabilities can be provided, including Wi-Fi, ZigBee, 3G/4G wireless, CAT6 wired Ethernet, and even optical fiber from the curb. Furthermore, because the smart keypad can be connected to the home 120V system, a HomePlug or other powerline-communications capability can be provided. Accordingly, the smart keypad can be connected to and communicate with the other smart-home devices of the smart-home environment 100 and to the central server or cloud-computing system 164.

The smart keypad can include any of the components (e.g., temperature sensor, humidity sensor, occupancy sensor, ambient light sensor, communication equipment, processors, memory, etc.) that are included in any of the other smart-home devices (e.g., smart doorbells 106, smart thermostats 102, smart wall switches 108, smart wall plugs 110, etc.) described herein. In some embodiments, the smart keypad is hardwired with a battery backup. In some embodiments, the smart keypad is incorporated into the wall switch 108, whereas in other embodiments the smart keypad can be its own device.

The smart keypad also includes sensors such as temperature, humidity, occupancy, ambient light, fire, smoke, carbon monoxide, active proximity, passive infrared motion, ultrasound, CCD/video camera, etc. As mentioned above, a rechargeable battery is also included (or equivalently capable onboard power storage medium). For example, the battery can be a rechargeable Lithium-Ion battery. In operation, the smart keypad charges the battery during time intervals in which the hardware power usage is less than what power stealing can optimally provide, and that will discharge to provide the needed extra electrical power during time intervals in which the hardware power usage is greater than what power stealing can optimally provide.

The user interface of the smart keypad can include one or more visual displays (LCD, TFT, OLED, etc.), touchscreen and/or button input capabilities, the audio speaker, and so forth. According to embodiments, an optional 2D image and/or 3D holographic image projector, can also be provided so that the effective dimension of the display is not just limited to the physical size of the smart keypad. The user interface can be user customized by the home occupants.

The smart keypad can be secured by a user-determined passcode. In some embodiments, the passcode can be a PIN comprising any number and combination of letters and/or numbers. In other embodiments, the passcode can be a phrase. In yet other embodiments, the passcode can be a gesture, which the smart keypad senses using ultrasonic sensors, PIR sensors, etc. In still other embodiments, the passcode is in the form of a unique connect-the-dot pattern, where the user interface displays a plurality of dots (e.g., a grid of dots) and the user moves his or her finger from dot to dot in a unique pattern. Any one of these forms of the passcode, including the gesture and the connect-the-dots pattern, can provide users with a quick and easy way to arm and disarm the alarm system of the home. For example when leaving the home, the user can walk up to the smart keypad and make the unique gesture or input the connect-the-dots pattern to arm the alarm. According to some embodiments, the smart keypad manages a user list, which includes a list of users and corresponding times they can control the keypad to arm/disarm the security system and to control other functions of the smart home. In some cases, the various users may identify themselves to the smart keypad using unique identification numbers and access codes, including the passcodes described above. Further, in some cases, the smart keypad may be capable of recognizing a user based on the user's "digital fingerprint", such as by wirelessly identifying the user's computer 166.

According to embodiments, the smart keypad includes a "light your path" feature, whereby the smart keypad activates a light when it senses that a user is approaching in darkness or near darkness. For example, in the event the user approaches the smart keypad in the middle of the night, the smart keypad may activate nearby lights in the home or a light incorporated in the smart keypad itself (e.g., LED) to provide a lighted pathway for the user. In one example, the smart keypad is incorporated in a wall light switch, and the smart keypad activates the light associated with the wall switch when a user is approaching the smart keypad. In some examples, upon detecting an approaching user when the security system is armed, the smart keypad or other devices of the home or the server 164 can send notification to the occupants' mobile devices or other electronic devices. Also, for example, the smart keypad can send a notification message to the occupants' mobile devices any time the alarm system is armed or disarmed by a user.

According to embodiments, the smart keypad is "smash and bash" resistant. For example, in the event the home's alarm system is armed and the smart keypad is smash (e.g., by an intruder attempting to disarm the alarm by bashing the keypad), the alarm remains armed. In some cases, upon being smashed, the smart keypad triggers the alarm and executes pre-configured actions, such as notifying police and/or other emergency personnel.

According to embodiments, the smart keypad or other devices in the home are capable of assigning user-defined gestures to actions or sets of actions. For example, the user may program the smart keypad with a "panic gesture" that causes the smart keypad, other devices in the smart home, or the server 164 to notify authorities, such as by calling or otherwise notifying medical, police, etc. Such a panic gesture may be, for example, the user quickly waving his or her hands in the air. The user may also program the smart keypad or other devices in the home with an audible panic command. For example, when the user yells "help", then medical, police, etc. may be called or otherwise notified. In other examples, the smart keypad can include a panic button that the user can press to call the police, medical, etc.

Displaying Messages on the Smart Keypad and Other Smart Devices

According to embodiments, the smart keypad or any of the other smart-home devices have the ability to display or project messages, such as via a display on the device itself or by projection. Messages may be displayable by the smart keypad, smart thermostat 102, or any of the other smart devices of the smart-home environment 100, according to embodiments. For example, when a person is at the front door, the smart keypads, smart thermostats and other smart devices may display or project a corresponding message, such as "Someone's at the door". This would be good for situations where the users have deactivated, or the smart home has automatically deactivated, the doorbell and/or other audible notifications because some or all of the occupants are sleeping. These messages would also be useful for hearing impaired occupants. Also for example, the smart keypads, smart thermostats and other smart devices may be configured to display or project safety and security warning messages, such as "Evacuate" due to possible intruder, fire, CO, etc. The message could be projected in large font on walls, floors, ceilings, etc. And the message could provide additional information. For example, the message could be "Intruder detected in den", "Fire detected in kitchen", etc.

According to embodiments, the smart keypad and the other smart devices are used as platforms for running home applications. For example, the smart keypad has the capability of downloading and/or executing applications that enable users to use the smart keypad to control their smart homes. For example, a user could install a "thermostat" app that can be accessed and controlled from any of the smart devices in the home, including the smart keypads, to control the home's HVAC. Thus, for example, a user interface could be provided on the smart keypad. The user could also install "security" and "safety" apps that communicate with hazard detector and security device of the home, and display messages. It should be appreciated that the number and type of apps that could be download and installed are endless.

Various modifications may be made without departing from the spirit and scope of the invention. Indeed, various user interfaces for operating hazard detectors, HVACs and other devices have been provided, yet these are meant to be illustrative and not limiting as to the scope of the overall invention. While methods and systems have been described for receiving hazard detection and hazard detector status information, it is contemplated that these methods may be applied to receive and/or communicate other information. It is to be further appreciated that the term hazard detector, as used hereinabove and hereinbelow, can include hazard detectors having direct wired connection with hazard response systems, and can further include hazard detectors that do not connect directly with the hazard response systems, but that provide alerts concerning detected potential hazard conditions.

Accordingly, the invention is not limited to the above-described embodiments, but instead is defined by the appended claims in light of their full scope of equivalents.

What is claimed is:

1. A method for determining one or more sources of carbon monoxide (CO) in a smart-home environment, the smart-home environment including a plurality of smart-home devices that have at least measurement and communication capabilities, the method comprising:
    linking each smart-home device of the plurality of smart-home devices with an online management account maintained by a cloud-computing system, wherein the cloud-computing system communicates with the plurality of smart-home devices via the Internet;
    registering a mobile device with the online management account maintained by the cloud-computing system, wherein the mobile device communicates with the cloud-computing system via the Internet;
    measuring a level of CO in the smart-home environment, by each smart-home device of the plurality of smart-home devices, to generate a plurality of CO measurements, wherein each smart-home device of the plurality of smart-home devices are located at different locations;
    providing the plurality of CO measurements and one or more current characteristics of the smart-home environment from one or more of the smart-home devices to an analyzing device;
    evaluating, by the analyzing device, based on the plurality of CO measurements and the one or more current characteristics of the smart-home environment, a set of CO correlation scenarios, wherein:
        each CO correlation scenario of the set of CO correlation scenarios indicates a corresponding specific CO source based on: smart device location, CO change trend, and the one or more current characteristics of the smart-home environment;
    selecting a specific CO source as the most likely source of the CO based on the evaluated set of CO correlation scenarios; and
    outputting a notification via the Internet to the mobile device that has been registered with the online management account with which the plurality of smart-home devices are linked, wherein the notification is indicative of the specific CO source as the most likely source of the CO.

2. The method of claim 1, wherein a result of evaluating each CO correlation scenario of the set of CO correlation scenarios is generation of a confidence metric that the plurality of CO measurements are due to a corresponding specific CO source, the method further comprises:
    generating a sum of confidence metrics that correspond to a same specific CO source.

3. The method of claim 2, wherein evaluating one or more of the CO correlation scenarios of the set of CO correlation scenarios comprises:
    generating a positive or negative result state for each of the one or more of the CO correlation scenarios of the set of CO correlation scenarios, and
    assigning a fixed value as the confidence metric responsive to generating the positive result state.

4. The method of claim 2, wherein evaluating one or more of the CO correlation scenarios of the set of CO correlation scenarios comprises generating a variable result for each of the one or more of the CO correlation scenarios, and assigning a variable value that is responsive to a degree of fit between the plurality of CO measurements and the one or more current characteristics, as the confidence metric.

5. The method of claim 2, wherein selecting one or more of the specific CO sources as the most likely source of the CO comprises comparing the sums of the confidence metrics for the corresponding CO sources and determining that one of the corresponding CO sources is more likely than all of the other sources.

6. The method of claim 2, wherein selecting one or more of the CO specific sources as the most likely source of the CO comprises determining that two or more of the corresponding sources are possible CO sources, responsive to the sums of the confidence metrics for each of the two or more corresponding CO sources being within a confidence window of one another.

7. The method of claim 1, wherein the analyzing device is a smart-home device of the plurality of smart-home devices that measures the CO, and others of the smart-home devices provide at least some of the current characteristics to the smart-home device that measures the CO.

8. The method of claim 1, wherein the analyzing device is a computer that receives the plurality of CO measurements and the current characteristics.

9. The method of claim 1, wherein:
    one of the CO correlation scenarios of the set of CO correlation scenarios includes CO measurements taken by one or more smart-home device of the plurality of smart-home devices in or adjacent to a garage;
    the one or more current characteristics include a time of day; and
    the specific CO source is automobile exhaust in the garage.

10. The method of claim 9, wherein the one or more current characteristics further include a day of the week.

11. The method of claim 9, wherein the one or more current characteristics further include an indication that a door associated with the garage has opened or closed.

12. The method of claim 1, wherein:
    one of the CO correlation scenarios of the set of CO correlation scenarios includes CO measurements taken by one or more smart-home device of the plurality of smart-home devices in or adjacent to a kitchen;
    the one or more current characteristics include detection of a temperature increase in the kitchen; and
    the specific CO source is operation of a gas stove in the kitchen.

13. The method of claim 12, wherein the one or more current characteristics further include detection of smoke in the kitchen.

14. The method of claim 12, wherein the CO measurements taken by one or more smart-home devices of the plurality of smart-home devices in or adjacent to a kitchen rise rapidly, while CO measurements taken by other smart-home devices of the plurality of smart-home devices do not change significantly.

15. The method of claim 1, wherein:
    one of the CO correlation scenarios of the set of CO correlation scenarios include CO measurements taken by one or more smart-home device of the plurality of smart-home devices in or adjacent to a location of a wood burning appliance;
    the one or more current characteristics include:
        detection of a temperature increase in the location of the one or more smart-home device of the plurality of smart-home devices, and
        information that an HVAC system is not operating as a heat source; and the specific CO source is wood burning in the wood burning appliance.

16. The method of claim 1, wherein:
one of the CO correlation scenarios of the set of CO correlation scenarios includes CO measurements taken by one or more smart-home device of the plurality of smart-home devices in or adjacent to a location of a water heater;
the one or more characteristics include detection of a humidity increase in or adjacent to a bathroom; and
the specific CO source is a CO leak from the water heater.

17. The method of claim 1, further comprising generating one of the CO correlation scenarios of the set of CO correlation scenarios by:
periodically generating CO measurements by a hazard detector of the smart-home devices;
storing the CO measurements;
periodically generating current characteristics of the smart-home environment that are not the CO measurements;
storing the current characteristics; and
generating the one of the CO correlation scenarios by evaluating a correlation possibility between the CO measurements and one or more of the current characteristics, by:
determining correlation of the CO measurements with the one or more of the current characteristics; and
discarding the correlation possibility responsive to no correlation being present between the CO measurements and the one or more of the current characteristics included in the correlation possibility; or
retaining the correlation possibility as the CO correlation scenario responsive to a correlation being present between the CO measurements and the one or more of the current characteristics included in the correlation possibility.

18. The method of claim 17, wherein storing the CO measurements comprises associating each of the CO measurements with a corresponding time identifier and location of the hazard detector, and storing the current characteristics comprises associating each of the current characteristics with a corresponding time identifier and a location of one of the smart-home devices that generated the current characteristic.

19. The method of claim 17, wherein:
one of the correlation possibilities is generated by randomly correlating the CO measurements with ones of the current characteristics.

20. A system for determining a source of carbon monoxide (CO) in a smart-home environment, the system comprising:
a plurality of smart-home devices located in different locations within the smart-home environment, wherein each smart-home device of the plurality of smart-home devices comprises: one or more sensors; a wireless communication interface; and one or more processors, each of the smart-home devices of the plurality of smart-home devices being configured to measure a level of CO;
a cloud-based computing system that links each smart-home device of the plurality of smart-home devices with an online management account and registers a mobile device with the online management account maintained by the cloud-based computing system, wherein the cloud-based computing system communicates with the plurality of smart-home devices and the mobile device via the Internet; and
a processing system, wherein the processing system is configured to:
receive a plurality of CO measurements and one or more current characteristics of the smart-home environment from one or more of the smart-home devices of the plurality of smart-home devices;
evaluate, based on the plurality of CO measurements and the one or more current characteristics of the smart-home environment, a set of CO correlation scenarios, wherein:
each CO correlation scenario of the set of CO correlation scenarios identifies a corresponding specific CO source based on: smart device location, CO change trend, and at least one of the current characteristics of the smart-home environment;
select a specific CO source as the most likely source of the CO, based on the evaluated set of CO correlation scenarios; and
cause a notification to be output via the Internet to the mobile device that has been registered with the online management account with which the plurality of smart-home devices are linked, wherein the notification is indicative of the specific CO source as the most likely source of the CO.

21. The system for determining the source of CO in the smart-home environment of claim 20, wherein the processing system being configured to evaluate each CO correlation scenario comprises the processing system being configured to:
generate a plurality of confidence metrics, each confidence metric of the plurality of confidence metrics corresponding to a specific CO correlation scenario of the set of CO correlation scenarios; and
aggregate confidence metrics of the plurality of confidence metrics that correspond to a same specific CO source.

22. The system for determining the source of CO in the smart-home environment of claim 21, wherein the processing system being configured to select the specific CO source as the most likely source of the CO comprises the processing system being configured to:
compare the aggregated confidence metrics; and
determine that the specific CO source is the most likely source of the CO based on the aggregated confidence metrics.

23. The system for determining the source of CO in the smart-home environment of claim 20, wherein the processing system is incorporated as part of a smart home device.

24. The system for determining the source of CO in the smart-home environment of claim 23, wherein the smart home device in which the processing system is incorporated is a carbon monoxide detector.

25. The system for determining the source of CO in the smart-home environment of claim 20, wherein the processing system is incorporated as part of the cloud-based computing system.

26. The system for determining the source of CO in the smart-home environment of claim 20, wherein the processing system is part of a distinct computerized system from the cloud-based computing system and the plurality of smart-home devices.

27. The system for determining the source of CO in the smart-home environment of claim 20, wherein a first CO correlation scenario of the set of CO correlation scenarios comprises:

at least some CO measurements of the plurality of CO measurements are taken in or adjacent to a garage;

the one or more current characteristics comprises a time of day; and the specific CO source is automobile exhaust in the garage.

28. The system for determining the source of CO in the smart-home environment of claim 27, wherein the one or more current characteristics comprises an indication that a garage door of the garage has opened or closed.

29. The system for determining the source of CO in the smart-home environment of claim 20, wherein a first CO correlation scenario of the set of CO correlation scenarios comprises:

at least some CO measurements of the plurality of CO measurements are taken in or adjacent to a kitchen;

the one or more current characteristics comprise detection of a temperature increase in the kitchen; and the specific CO source is operation of a gas stove in the kitchen.

30. The system for determining the source of CO in the smart-home environment of claim 20, wherein a first CO correlation scenario of the set of CO correlation scenarios comprises:

at least some CO measurements of the plurality of CO measurements being taken in or adjacent to a location of a water heater;

the one or more current characteristics comprise detection of a humidity increase in or adjacent to a bathroom; and the specific CO source is the water heater.

* * * * *

UNITED STATES PATENT AND TRADEMARK OFFICE
CERTIFICATE OF CORRECTION

PATENT NO. : 10,546,469 B2
APPLICATION NO. : 14/508777
DATED : January 28, 2020
INVENTOR(S) : Kevin Peterson et al.

Page 1 of 1

It is certified that error appears in the above-identified patent and that said Letters Patent is hereby corrected as shown below:

In the Claims

Claim 16, Column 83, Line 9:
Please insert --current-- before the word characteristics.

Signed and Sealed this
Seventh Day of July, 2020

Andrei Iancu
*Director of the United States Patent and Trademark Office*